United States Patent
Beach et al.

(12) 
(10) Patent No.: US 6,503,742 B1
(45) Date of Patent: Jan. 7, 2003

(54) UBIQUITIN LIGASES AND USES RELATED THERETO

(75) Inventors: David Beach, Huntington Bay, NY (US); Maureen G. Caligiuri, Huntington, NY (US); Bradley Nefsky, Highland Park, NJ (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 09/392,163

(22) Filed: Sep. 8, 1999

Related U.S. Application Data

(63) Continuation of application No. 08/539,205, filed on Oct. 4, 1995, now Pat. No. 6,001,619.

(51) Int. Cl.[7] ............................ C12N 15/52; C12N 9/00
(52) U.S. Cl. ................. 435/183; 435/320.1; 435/252.3; 435/325; 536/23.2
(58) Field of Search ............................... 536/23.1, 23.2; 435/183, 252.3, 325, 320.1

(56) References Cited

PUBLICATIONS

J.T. Mulligan et al. GenBank Accession No. L11119. Feb. 17, 1993.*

J.M. Huibregtse et al. "A Family of Proteins Structurally and Functionally Related to the E6–AP Ubiquitin–Protein Ligase", PNAS 92: 2563–2567. 3/1995.*

GenBank Accession No. R19498. Apr. 14, 1995.*

GenBank Accession No. T74302. Mar. 7, 1995.*

GenBank Accession No. R14620. Apr. 13, 1995.*

GenBank Accession No. R61402. May 24, 1995.*

* cited by examiner

*Primary Examiner*—Rebecca E. Prouty
(74) *Attorney, Agent, or Firm*—Ropes & Gray

(57) ABSTRACT

The present invention relates to the discovery in eukaryotic cells of a ubiquitin ligases. These proteins are referred to herein collectively as "pub" proteins for Protein UBiquitin ligase, and individually as h-pub1, h-pub2 and s-pub1 for the human pub1 and pub2 and *Schizosaccharomyces pombe* pub1 clones, respectively. Pub1 proteins apparently play a role in the ubiquitination of the mitotic activating tyrosine phosphatase cdc25, and thus they may regulate the progression of proliferation in eukaryotic cells by activating the cyclin dependent kinase complexes. In *S. pombe*, disruption of s-pub1 elevates the level of cdc25 protein in vivo increasing the activity of the tyrosine kinases, wee1 and mik1, required to arrest the cell-cycle. Loss of wee1 function in an *S. pombe* cell carrying a disruption in the s-pub1 gene results in a lethal premature entry into mitosis; such lethal phenotype can be rescued by the loss of cdc25 function. An ubiquitin thioester adduct of s-pub1 can be isolated from *S.pombe* and disruption of s-pub1 dramatically reduces ubiquitination of cdc25.

12 Claims, No Drawings

UBIQUITIN LIGASES AND USES RELATED THERETO

This application is a continuation and claims priority to U.S. Ser. No. 08/539,205, filed Oct. 4, 1995 now U.S. Pat. No. 6,001,619.

FUNDING

Work described herein was supported by National Institutes of Health Grant No. GM39620 and the Howard Hughes Medical Institute.

Work described herein was supported by National Institutes of Health Grant and the Howard Hughes Medical Institute. The United States Government has certain rights in the invention.

BACKGROUND OF THE INVENTION (a) Cell-cycle Regulatory Proteins

Cell-cycle events are thought to be regulated by a series of interdependent biochemical steps. In eukaryotic cells mitosis does not normally take place until the G1, S and G2 phases of the cell-cycle are completed. In all eukaryotic cells examined to date, the cell cycle appears to be regulated by the sequential activation of a series of the CDK's or Cyclin Dependent Kinases (reviewed in Morgan, (1995) *Nature* 374:131–134; King et al., (1994) *Cell* 79:563–571; Norbury and Nurse, (1992) *Annu. Rev. Biochem.* 61:441–470). Yeast cells contain a single CDK known as cdc2 in *S. pombe* (Beach et al., (1982) *Nature* 300:706–709; Booher and Beach, (1986) *Gene* 31:129–134; Hindley and Phear, (1984) *Gene* 21:129–134; Nurse and Bissett, (1981) *Nature* 292:558–560; Simanis and Nurse, (1986) *Cell* 45:261–268; and for review see Forsburg and Nurse, (1991b) *Annu. Rev. Cell Riol.* 7:227–256) and cdc28 in *S. cerevisae*. The similarities between the progression of proliferation in mammalian cells and yeast have suggested similar roles for cdc protein kinases across species. In support of this hypothesis, a human cdc2 gene has been found to be able to substitute for the activity of an *S. pombe* cdc2 gene in both its G1/S and G2/M roles (Lee et al., (1987) *Nature* 327:31). Likewise, the fact that the cdc2 homolog of *S. cerevisae* (cdc28) can be replaced by the human cdc2 also emphasizes the extent to which the basic cell-cycle machinery has been conserved in evolution.

The activation of cdc2 kinase activity occurs during the M phase and is controlled at multiple levels involving, among other events, the association with various cyclin subunits and the phosphorylation on threonine 167 by cdc2 activating kinase (CAK) (Booher and Beach, (1987) *EMBO J.* 6:3441–3447; Booher et al., (1989) *Cell* 58:485–497; Bueno et al., (1991) *Cell* 66:149–159; Bueno and Russell, (1993) *Mol. Cell Biol.* 13:2286–2297; Connolly and Beach, (1994) *Mol. Cell Biol.* 14:768–776; Fesquet et al., (1993) *EMBO J.* 12:3111–3121; Forsburg and Nurse, (1991a) *Nature* 351:245–247; Gould et al., (1991) *EMBO J.* 3297–3309; Hagan et al., (1988) *J. Cell Sci.* 91:587–595; Solomon et al., (1992) *Mol. Biol. Cell* 3:13–27; Solomon et al., (1993) *EMBO J.* 12:3133–3142). Another well-characterized mechanism of regulating the activity of cdc2 involves its inhibition by phosphorylation of a tyrosine and threonine residues (Tyr-15 and Thr-14) within its ATP binding site (Gould and Nurse, (1989) supra). The inhibitory phosphorylation of cdc2 is mediated at least impart by the wee1 and mik1 tyrosine kinases (Russel et al., (1987) *Cell* 49:559–567; Lundgren et al., (1991) *Cell* 64:1111–1122; Featherstone et al., (1991) *Nature* 349:808–811; and Parker et al., (1992) *PNAS* 89:2917–2921). These kinases act as mitotic inhibitors, over-expression of them causes cells to arrest in the G2 phase of the cell-cycle. By contrast, loss of function of wee1 causes a modest advancement of mitosis, whereas loss of both wee1 and mik1 function causes grossly premature mitosis, uncoupled from all checkpoints that normally restrain cell division (Lundgren et al., (1991) *Cell* 64:1111–1122).

As the cell is about to reach the end of G2, dephosphorylation of the cdc2-inactivating Thr-14 and Tyr-15 residues occurs leading to activation of the cdc2 complex as a kinase. With the exception of budding yeast and the early embryonic cell divisions of some organisms, the dephosphorylation of tyrosine 15 is a key regulatory step of cdc2 activation (Morla et al., (1989) *Cell* 58:193–203; Heald et al., (1993) *Cell* 74:463–474; and for reviews see King et al., (1994) *Cell* 79:563–571; and Morgan (1995) *Nature* 374:131–134). A stimulatory phosphatase, known as cdc25, is responsible for Tyr-15 and Thr-14 dephosphorylation and serves as a rate-limiting mitotic activator. (Dunphy et al., (1991) *Cell* 67:189–196; Lee et al., (1992) *Mol Biol Cell* 3:73–84; Millar et al., (1991) *EMBO J* 10:4301–4309; and Russell et al., (1986) *Cell* 45:145–153). Cdc25 has been shown to be required for entry into mitosis in a number of different organisms (King et al., 1994). Evidence indicates that both the cdc25 phosphatase and the cdc2-specific tyrosine kinases are detectably active during interphase, suggesting that there is an ongoing competition between these two activities prior to mitosis (Kumagai et al., (1992) *Cell* 70:139–151; Smythe et al., (1992) *Cell* 68:787–797; and Solomon et al., (1990) *Cell* 63:1013–1024. This situation implies that the initial decision to enter mitosis involves a modulation of the equilibrium of the phosphorylation state of cdc2 which is likely controlled by variation of the rate of tyrosine dephosphorylation of cdc2 and/or a decrease in the rate of its tyrosine phosphorylation.

In *S. pombe*, the level of cdc25 oscillates in a cell cycle dependent fashion (Ducommum et al., (1990) *Biochem. Biophys. Res. Comm.* 167:301–309; Moreno et al., (1990) *Nature* 344:549–552). Cdc25 accumulates through the cell cycle until mitosis when its level rapidly decreases. The pattern of cdc25 accumulation during the cell cycle is reminiscent of mitotic cyclins which are degraded by the ubiquitin system (Glotzer et al., (1991) *Nature* 349:132–138; Seufert et al., (1995) *Nature* 373:78–81).

(b) Ubiquitination Pathways

The ubiquitin-mediated proteolysis system is the major pathway for the selective, controlled degradation of intracellular proteins in eukaryotic cells. Ubiquitin modification of a variety of protein targets within the cell appears to be important in a number of basic cellular functions such as regulation of gene expression, regulation of the cell-cycle, modification of cell surface receptors, biogenesis of ribosomes, and DNA repair. One major function of the ubiquitin-mediated system is to control the half-lives of cellular proteins. The half-life of different proteins can range from a few minutes to several days, and can vary considerably depending on the cell-type, nutritional and environmental conditions, as well as the stage of the cell-cycle.

Targeted proteins undergoing selective degradation, presumably through the actions of a ubiquitin-dependent proteosome, are covalently tagged with ubiquitin through the formation of an isopeptide bond between the C-terminal glycyl residue of ubiquitin and a specific lysyl residue in the substrate protein. This process is catalyzed by a ubiquitin-activating enzyme (E1) and a ubiquitin-conjugating enzyme (E2), and in some instances may also require auxiliary substrate recognition proteins (E3s). Following the linkage of the first ubiquitin chain, additional molecules of ubiquitin may be attached to lysine side chains of the previously conjugated moiety to form branched multi-ubiquitin chains.

The conjugation of ubiquitin to protein substrates is a multi-step process. In an initial ATP requiring step, a thioester is formed between the C-terminus of ubiquitin and an internal cysteine residue of an E1 enzyme. Activated ubiquitin is then transferred to a specific cysteine on one of several E2 enzymes. Finally, these E2 enzymes donate ubiquitin to protein substrates. Substrates are recognized either directly by ubiquitin-conjugated enzymes or by associated substrate recognition proteins, the E3 proteins, also known as ubiquitin ligases.

Many proteins that control cell-cycle progression are short-lived. For example, regulation of oncoproteins and anti-oncoproteins clearly plays an important role in determining steady-state levels of protein expression, and alterations in protein degradation are as likely as changes in transcription and/or translation to cause either the proliferative arrest of cells, or alternatively, the transformation of cells.

SUMMARY OF THE INVENTION

The present invention relates to the discovery in eukaryotic cells of novel family of proteins whose apparent function includes a ubiquitin ligase activity. In particular, one feature of members of this family of proteins includes a catalytic domain containing a region homologous to the putative catalytic domain of the human protein ubiquitin ligase E6-AP. The subject proteins are referred to herein collectively as "pub proteins" or "pub ligases" for Protein UBiquitin ligase. As described herein, this family of proteins include at least two paralogous classes of mammalian homologs, "pub1" and "pub2". We have cloned at least one human pub1 gene (h-pub1), e.g., a human pub1 protein having an apparent molecular weight of 84.5 kDa, as well as a *Schizosaccharomyces pombe* pub1 gene (s-pub1) having an apparent molecular weight of 85 kDa. Additionally, we have cloned a human pub2 gene (h-pub2) characterized by an apparent molecular weight of 96.2 kd. The pub proteins have an apparent function in the ubiquitination of, among other cellular proteins, the mitotic activating tyrosine phosphatase cdc25. Accordingly, the subject proteins may be involved in regulating the progression of proliferation in eukaryotic cells by effectively controling the activity of the cdk complexes by modulating the availablity of cdc25.

Moreover, as described in further detail below, the subject pub1 proteins contain a sequence motif (CaLB) which is highly homologous to a consensus sequence which has been implicated in $Ca^{+2}$-dependent binding to phospholipid membranes in several proteins such as phospholipase A2, PKC and rasGAP.

In *S. pombe,* disruption of s-pub1 elevates the level of cdc25 protein in vivo increasing the activity of the tyrosine kinases, wee1 and mik1, required to arrest the cell cycle. Loss of wee1 function in an *S. pombe* cell carrying a disruption in the s-pub1 gene results in a lethal premature entry into mitosis; such lethal phenotype can be rescued by the loss of cdc25 function. An ubiquitin thioester adduct of s-pub1 can be isolated from *S. pombe* and disruption of s-pub1 dramatically reduces ubiquitination of cdc25. These results indicate that s-pub1 may directly ubiquitinate cdc25 in vivo.

One aspect of the invention features a substantially pure preparation of an h-pub1 polypeptide, e.g., full length or fragments thereof, the full-length form of the h-pub1 protein having an approximate molecular weight in the range of 75–95 kD, preferably about 80–90 kD. In a preferred embodiment: the polypeptide has an amino acid sequence at least 70% homologous to an amino acid sequence represented in SEQ. ID No. 2; the polypeptide has an amino acid sequence at least 80% homologous to an amino acid sequence represented in SEQ. ID No. 2; the polypeptide has an amino acid sequence at least 90% homologous to an amino acid sequence represented in SEQ. ID No. 2; the polypeptide has an amino acid sequence identical to an amino acid sequence represented in SEQ. ID No. 2. In preferred embodiments the fragment comprises at least, for example, 25, 50 or 75 contiguous amino acid residues of SEQ. ID No. 2. For instance, certain embodiments of the subject h-pub1 protein will include a catalytic domain having a ubiquitin ligase activity, and (optionally) all or only a portion of other sequences of the full-length h-pub1, e.g. a calcium-binding domain (CalB motif) and/or an ATP-binding site.

Another aspect of the invention features a substantially pure preparation of an h-pub2 polypeptide, e.g., full length or fragments thereof, the full-length form of the h-pub2 protein having an approximate molecular weight in the range of 85–105 kD, preferably about 90–100 kD. In a preferred embodiment: the polypeptide has an amino acid sequence at least 70% homologous to an amino acid sequence represented in SEQ ID No. 6; the polypeptide has an amino acid sequence at least 80% homologous to an amino acid sequence represented in SEQ ID No. 6; the polypeptide has an amino acid sequence at least 90% homologous to an amino acid sequence represented in SEQ ID No. 6; the polypeptide has an amino acid sequence identical to an amino acid sequence represented in SEQ ID No. 6. In preferred embodiments the fragment comprises at least, for example, 25, 50 or 75 contiguous amino acid residues of SEQ ID No. 6. For instance, certain embodiments of the subject h-pub2 protein will include a catalytic domain having a ubiquitin ligase activity.

Still another aspect of the invention features a substantially pure preparation of an s-pub1 polypeptide, including fragments of the full-length portion, the full-length form of the p85 protein having an approximate molecular weight in the range of 80–90 kD, preferably about 85 kD. In a preferred embodiment: the polypeptide has an amino acid sequence at least 70% homologous to an amino acid sequence represented in SEQ ID No. 4; the polypeptide has an amino acid sequence at least 80% homologous to an amino acid sequence represented in SEQ ID No. 4; the polypeptide has an amino acid sequence at least 90% homologous to an amino acid sequence represented in SEQ ID No. 4; the polypeptide has an amino acid sequence identical to an amino acid sequence represented in SEQ ID No. 4. In preferred embodiments: the fragment comprises at least 25, 50 or 75 contiguous amino acid residues of SEQ ID No. 4. As above, preferred embodiments of the subject s-pub1 protein include a catalytic domain and (optionally) a Calb motif and/or ATP-binding site. However, it will be understood that, for certain uses, only the non-catalytic domains/motifs may be desired.

Polypeptides referred to herein as pub polypeptides, in addition to h-pub1, h-pub2 or s-pub1 further refers to other mammalian paralogs, or other mammalian orthologs.

In general, the biological activity of a pub polypeptide can be characterized as including the ability to transfer an ubiquitin molecule from the relevant ubiquitin conjugating enzyme (UBC) to a residue of a target through a pub ubiquitin thioester intermediate. Moreover, a "pub biological activity" also refers to an ability to specifically antagonize the biochemical action of a wild-type pub protein, e.g., a pub protein represented by SEQ ID Nos. 2, 4 or 6. In other words, dominant negative mutants of pub are included within the scope of pub biological activity. Such mutants are exemplified by mutation of the active site cysteine to an alanine or other catalytically inactivating mutant. The biological activity of the pub1 proteins may also include the ability to translocate to specific phospholipid membranes in the presence of calcium and/or to bind a nucleotidyl phosphate such as ATP.

The above notwithstanding, the biological activity of a pub polypeptide may be characterized by one or more of the following attributes: an ability to regulate the cell-cycle of an eukaryotic cell; an ability to modulate proliferation/cell growth of an eukaryotic cell; an ability to modulate entry of a mammalian or yeast cell into M phase; an ability to ubiquitinate a cell-cycle regulator, e.g. a tyrosine phosphatase involved in cell-cycle progression, e.g. a cdc25 phosphatase. Such activities may be manifested by the ability to control the steady state level of cdc25 phosphatase, and thus to control the degree of dephosphorylation of a CDK kinase, e.g. cdc2 or the like. The pub polypeptides of the present invention may also function to modulate differentiation of cells/tissue. The subject polypeptides of this invention may also be capable of modulating cell growth or proliferation by influencing the action of other cellular proteins. A pub polypeptide can be a specific agonist of the function of the wild-type form of the protein, or can be a specific antagonist.

Yet another aspect of the present invention concerns an immunogen comprising a pub polypeptide of the present invention, or a fragment thereof, in an immunogenic preparation, the immunogen being capable of eliciting an immune response specific for the pub polypeptide; e.g. a humoral response, e.g. an antibody response; e.g. a cellular response.

Another aspect of the present invention features recombinant h-pub1, h-pub2 or s-pub1 polypeptides, or fragments thereof, having amino acid sequences preferably identical or homologous to the amino acid sequence designated by SEQ ID No. 2, SEQ ID No. 4 or SEQ ID No. 6, respectively.

Another aspect of the present invention provides a substantially pure nucleic acid having a nucleotide sequence which encodes an h-pub1 polypeptide, or a fragment thereof, having an amino acid sequence at least 70% homologous to SEQ ID No. 2. In a more preferred embodiment: the nucleic acid encodes a protein having an amino acid sequence at least 80% homologous to SEQ ID No. 2. more preferably at least 90% homologous to SEQ ID No. 2, and most preferably at least 95% homologous to SEQ ID No. 2. The nucleic preferably encodes an h-pub1 protein which specifically transfers an ubiquitin molecule form the relevant UBC to a substrate protein, e.g., cdc25, or specifically antagonizes such ubiquitination.

Another aspect of the present invention provides a substantially pure nucleic acid having a nucleotide sequence which encodes an h-pub1 polypeptide, or a fragment thereof, having an amino acid sequence at least 70% homologous to SEQ ID No. 6. In a more preferred embodiment: the nucleic acid encodes a protein having an amino acid sequence at least 80% homologous to SEQ ID No. 6, more preferably at least 90% homologous to SEQ ID No. 6, and most preferably at least 95% homologous to SEQ ID No. 6. The nucleic preferably encodes an h-pub2 protein which specifically transfers an ubiquitin molecule form the relevant UBC to a substrate protein, e.g., cdc25, or specifically antagonizes such ubiquitination.

Yet another aspect of the present invention provides a substantially pure nucleic acid having a nucleotide sequence which encodes an s-pub1 polypeptide, or a fragment thereof, having an amino acid sequence at least 70% homologous to SEQ ID No. 4. In a more preferred embodiment: the nucleic acid encodes a protein having an amino acid sequence at least 80% homologous to SEQ ID No. 4, more preferably at least 90% homologous to SEQ ID No. 4, and most preferably at least 95% homologous to SEQ ID No. 4. The nucleic preferably encodes an s-pub1 protein which specifically transfers an ubiquitin molecule form the relevant UBC to a cell cycle regulator, e.g., mitotic activating tyrosine phosphatase, e.g., cdc25.

In another embodiment, the nucleic acid hybridizes under stringent conditions to a nucleic acid probe corresponding to at least 25 consecutive nucleotides of SEQ ID Nos. 1, 3 or 6; more preferably to at least 50 consecutive nucleotides of one or both of SEQ ID Nos. 1, 3 or 6; more preferably to at least 75 consecutive nucleotides of SEQ ID No. 1, 3 or 6.

Furthermore, in certain embodiments, the pub nucleic acid will comprise a transcriptional regulatory sequence, e.g. at least one of a transcriptional promoter or transcriptional enhancer sequence, operably linked to the pub gene sequence so as to render the recombinant pub gene sequence suitable for use as an expression vector.

The present invention also features transgenic non-human animals, e.g. mice, which either express a heterologous pub gene, e.g. derived from humans, or which mis-express their own pub gene, e.g. expression is disrupted. Such a transgenic animal can serve as an animal model for studying cellular disorders comprising mutated or mis-expressed pub alleles.

The present invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of SEQ ID Nos. 1, 3 or 6, or naturally occurring mutants thereof. In preferred embodiments, the probe/primer further comprises a label group attached thereto and able to be detected, e.g. the label group is selected from a group consisting of radioisotopes, fluorescent compounds, enzymes, and enzyme co-factors. Such probes can be used as a part of a diagnostic test kit for identifying transformed cells, such as for measuring a level of a nucleic acid encoding a pub polypeptide in a sample of cells isolated from a patient; e.g. for measuring the mRNA level in a cell or determining whether the genomic pub gene has been mutated or deleted.

Another aspect of the present invention provides a method of determining if a subject, e.g. a human patient, is at risk for a disorder characterized by unwanted cell proliferation, comprising detecting, in a tissue of the subject, the presence or absence of a genetic lesion characterized by at least one of (i) a mutation of a pub gene, e.g., encoding a pub1 protein represented by SEQ ID No. 2, a pub2 protein represented by SEQ ID No. 6, or a homolog thereof; (ii) the mis-expression of the h-pub1 gene. In preferred embodiments: detecting the genetic lesion comprises ascertaining the existence of at least one of a deletion of one or more nucleotides from said gene, an addition of one or more nucleotides to said gene, an substitution of one or more nucleotides of said gene, a gross chromosomal rearrangement of said gene, a gross alteration in the level of a messenger RNA transcript of said gene, the presence of a non-wild type splicing pattern of a messenger RNA transcript of said gene, or a non-wild type level of said protein. For example, detecting the genetic lesion can comprise (i) providing a probe/primer comprising an oligonucleotide containing a region of nucleotide sequence which hybridizes to a sense or antisense sequence of SEQ ID No. 1 or 5, or naturally occurring mutants thereof, or 5' or 3' flanking sequences naturally associated with the h-pub1 gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the h-pub1 gene and, optionally, of the flanking nucleic acid sequences; e.g. wherein detecting the lesion comprises utilizing the probe/primer in a polymerase chain reaction (PCR); e.g. wherein detecting the lesion comprises utilizing the probe/primer in a ligation chain reaction (LCR). In alternate embodiments, the level of said protein is detected in an immunoassay.

Moreover, the present invention provides a practical approach for the identification of candidate agents able to modulate, e.g., activate or inhibit, ubiquitin-mediated degradation of a cell-cycle regulatory protein in eukaryotic cells, especially yeast and mammalian cells. For instance, the assays permit identification of agents which modulate the ubiquitination of a cell cycle regulatory protein, e.g., a mitotic activating tyrosine phosphatase, e.g., cdc25 phosphatase.

One aspect of the present invention relates to a method for identifying an activator or an inhibitor of ubiquitin-mediated proteolysis of a cell-cycle regulatory protein by (i) providing a ubiquitin-conjugating system that includes the substrate protein, an E3-like complex (e.g., comprising a pub protein a ligase activity thereof), and ubiquitin under conditions which promote the ubiquitination of the target protein, and (ii) measuring the level of ubiquitination of the subject protein brought about by the system in the presence and absence of a candidate agent. For example, a decrease in the level of ubiquitin conjugation is indicative of an inhibitory activity for the candidate agent. The level of ubiquitination of the regulatory protein can be measured by determining the actual concentration of protein:ubiquitin conjugates formed; or inferred by detecting some other quality of the subject protein affected by ubiquitination, including the proteolytic degradation of the protein. In certain embodiments, the present assay comprises an in vivo ubiquitin-conjugating system, such as a cell able to conduct the regulatory protein through at least a portion of a ubiquitin-mediated proteolytic pathway. In other embodiments, the present assay comprises an in vitro ubiquitin-conjugating system comprising a reconstituted protein mixture in which at least the ability to transfer ubiquitin to the regulatory protein is constituted.

Still another approach relies on a competitive binding assay to detect potential modulatory agents. For example, the ability of all or a portion of the pub protein to bind to cdc25 (or another cellular substrate protein) or other components of the ubiquitin pathway (e.g. E2's) can be assessed in the presence and absence of a test agent. In similar fashion, the ability of a test agent to modulate the function of the CaLB motif of a pub1 protein can be assessed.

The present invention also provides a method for producing a hyper- or a hypo-proliferative cell, e.g., a cell which has an impaired cell-cycle checkpoint such as the premature progression of the cell through at least a portion of a cell-cycle. As an example, a hyper-proliferative cell, e.g., a transformed mammalian cell, can be produced by disrupting a pub gene or gene product. Such cells are useful for identifying agents that modulate proliferation such as mitotic inhibitors, e.g., agents which may inhibit at least one regulatory protein of the cell cycle in a manner which counter-balances the effect of the impairment.

The impaired checkpoint can be generated, for example, by molecular biological, genetic, and/or biochemical means. The checkpoint to be impaired can comprise a regulatory protein or proteins which control progression through the cell-cycle, such as those which control the G2/M transition. By way of example, the impaired checkpoint can comprise a pub protein which controls the ubiquitination of a cdc25 phosphatase, and thus the degree of dephosphorylation of a CDK protein kinase, such as cdc2.

In another embodiment, cells impaired in a mitotic checkpoint can also be created by using agents which disrupt the binding of a pub protein to at least one of its targets, e.g., a cdc25 phosphatase. Such a system can be used to modulate cell proliferation and/or growth. In one embodiment, the method comprises administering a pub mimetic, e.g. a peptidomimetic, which binds to a cdc25 phosphatase, and inhibits the interaction between that protein and a pub ligase.

Furthermore, humanized yeast cells can be generated so as to comprise heterologous cell-cycle proteins (i.e. cross-species expression). For example, an exogenous pub can be expressed in a Schizosaccharomyces cell, such as *Schizosaccharomyces pombe* carrying a null mutation of the pub gene. The exogenous pub can be, for example, the human pub homolog described herein. Humanized yeast cells can provide useful assays for screening modulators, e.g., activators or inhibitors, of proliferation in vivo.

Other features and advantages of the invention will be apparent from the following detailed description, and from the claims. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press, 1989); *DNA Cloning*, Volumes I and II (D. N. Glover ed., 1985); *Oligonucleotide Synthesis* (M. J. Gait ed., 1984); Mullis et al., U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al., eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

DETAILED DESCRIPTION OF THE INVENTION

The cyclin dependent kinases are subject to multiple levels of control. One well-characterized mechanism regulating the activity of cdks involves the phosphorylation of tyrosine, threonine, and serine residues; the phosphorylation level of which varies during the cell-cycle (Draetta et al. (1988) *Nature* 336:738–744; Dunphy et al. (1989) *Cell* 58:181–191; Morla et al. (1989) *Cell* 58:193–203; Gould et al. (1989) *Nature* 342:39–45; and Solomon et al. (1990) *Cell* 63:1013–1024). The phosphorylation of cdc2, for example, on Tyr-15 and Thr-14, two residues located in the putative ATP binding site of the kinase, negatively regulates kinase activity. This inhibitory phosphorylation of cdc2 is mediated at least impart by the wee1 and mik1 tyrosine kinases (Russel et al. (1987) *Cell* 49:559–567; Lundgren et al. (1991) *Cell* 64:1111–1122; Featherstone et al. (1991) *Nature* 349:808–811; and Parker et al. (1992) *PNAS* 89:2917–2921). These kinases act as mitotic inhibitors, over-expression of which causes cells to arrest in the G2 phase of the cell-cycle. By contrast, loss of function of wee1 causes a modest advancement of mitosis, whereas loss of both wee1 and mik1 function causes grossly premature mitosis, uncoupled from all checkpoints that normally restrain cell division (Lundgren et al. (1991) *Cell* 64:1111–1122).

Dephosphorylation of the cdk-inactivating Thr-14 and Tyr-15 residues occurs leading to activation of the cdk/cyclin complex as a kinase. A stimulatory phosphatase, known as cdc25, is responsible for Tyr-15 and Thr-14 dephosphorylation and serves as a rate-limiting mitotic activator. (Dunphy et al. (1991) *Cell* 67:189–196; Lee et al. (1992) *Mol Biol Cell* 3:73–84; Millar et al. (1991) *EMBO J* 10:4301–4309; and Russell et al. (1986) *Cell* 45:145–153). Recent evidence indicates that both the cdc25 phosphatase and the cdk-specific tyrosine kinases (wee1/mik1) are detectably active during the cell-cycle, suggesting that there is an ongoing competition between these two activities to fine tune cell-cycle progression (Kumagai et al. (1992) *Cell* 70:139–151; Smythe et al. (1992) *Cell* 68:787–797; and Solomon et al. (1990) *Cell* 63:1013–1024.

The role of the ubiquitin dependent proteolytic pathway in the regulation of cdc25 has been examined by us both in vivo and in vitro. We have observed that cdc25A can be ubiquitinated in vitro, which ubiquitination requires an active E1 enzyme. Furthermore, we have found that the level of cdc25 protein increases upon inactivation of a temperature sensitive E1 gene. In addition, poly-ubiquitinated cdc25 can be detected in cells overexpressing a histidine-tagged ubiquitin gene. Finally, inhibition of the 26S proteosome with the peptide aldehyde N-acetyl-Leu-Leu-norleucinal (LLnL) leads to the accumulation of the phosphorylated form of cdc25. Moreover, results from in vitro ubiquitination reactions support the notion that phosphorylation of cdc25 may be a necessary prerequisite for ubiquitination. This finding is likely to be physiologically relevant to the regulated degradation of cdc25, because it is the phosphorylated form of cdc25 which is active as a protein phosphatase.

The specificity of the ubiquitination reaction is thought to be conferred at least in part by the E3 protein. We therefore sought to clone the E3 ligase(s) which specifically target :cdc25 for ubiquitin-dependent degradation. The present invention makes available nucleic acids encoding gene products which play a role in the ubiquitinylation of cdc25, and perhaps other regulatory proteins. Accordingly, the subject gene products may effect growth of eukaryotic cells by functioning as a tumor suppressor which down regulates mitotic acitivation by cdc25. Given the prominence of the cdc25 regulatory pathways in various aspects of cell growth, and probably differentiation, a salient feature for each of the subject nucleic acids, polypeptides, antibodies, and derivatives thereof, includes both therapeutic and diagnostic uses. Moreover, drug screening assays are described herein which provide a systematic and practical approach for identifying candidate agents able to modulate, e.g., activate or inhibit, ubiquitin-mediated degradation of a cell-cycle regulatory protein, such as the mitotic activating tyrosine phosphatase cdc25, in the eukaryotic cells, e.g. mammalian, e.g., human cells.

In particular, as described in the appended examples, the present invention describes the cloning of novel proteins containing a region homologous to the putative catalytic domain of the human protein ubiquitin ligase E6-AP and other ubiquitin ligases. The proteins which are the subject of the present invention are referred to herein collectively as "pub" proteins for protein ubiquitin ligases. As described herein, these proteins include a yeast pub gene product and several human homologs. For example, we have cloned the genes for a human pub protein, referred to herein as "h-pub1", having an apparent molecular weight of 84.5 kDa (h-pub1), as well as a *Schizosaccharomyces pombe* homolog, "s-pub1", having an apparent molecular weight of 85 kDa. In addition, we have cloned other pub paralogs from human cDNA libraries, such as the 96.2 kd "h-pub2" polypeptide described below. The nucleic acid and amino acid sequences, respectively, for each of the exemplary pub proteins are provided in the appended sequence listing as follows: SEQ ID No. 1 and 2 for h-pub1, SEQ ID No. 3 and 4 for s-pub1, and SEQ ID No. 5 and 6 for h-pub2.

The pub proteins apparently play a role in the ubiquitination of regulatory proteins, such as the mitotic activating tyrosine phosphatase cdc25, and thus they may regulate the progression of proliferation in eukaryotic cells by regulating the activity of cdk complexes. All known protein ubiquitin ligases (E3s) contain a carboxyl terminal "hect" domain (for homologous to E6-AP carboxyl terminus). See Huibregtse et al. (1995) *PNAS* 92:2563–2567. The hect domain for s-pub1 corresponds to Tyr662-Glu766 of SEQ ID No. 4, while the hect domain of h-pub1 is provided by Ile639-Glu735 of SEQ ID No. 2, and the hect domain pf h-pub2 is represented in Ile727-Asp834 of SEQ ID No. 6. The active site cysteine resides in the hect domain (Cys734 for s-pub1, Cys703 for h-pub1, and Cys801 for h-pub2).

Both h-pub1 and h-pub2 share about 50 percent homology with the hect domain of s-pub1. The fussion yeast pub1 protein apparently has two additional motifs, an ATP binding motif (Gly84-Gly89) and a calcium lipid binding domain (Leu20-Asn67; termed here a "CaLB" motif) which is highly homologous to a consensus sequence implicated in: $Ca^{+2}$ dependent binding to phospholipid membranes in several proteins such as phospholipase A2, PKC and ras-GAP. Both the CaLB and ATP binding domains of s-pub1 are conserved in h-pub1 (see SEQ ID No. 2, Leu19-Ser59 for CaLB motif, and Gly77-Gly82 for ATP binding motif), but not apparently in h-pub2.

In *S. pombe*, disruption of s-pub1 elevates the level of cdc25 protein in vivo. Loss of wee1 function in an *S. pombe* cell carrying a disruption in the s-pub1 gene results in a lethal premature entry into mitosis; such lethal phenotype can be rescued by the loss of cdc25 function. An ubiquitin thioester adduct of s-pub1 can be isolated from *S. pombe* and disruption of s-pub1 dramatically reduces ubiquitination of cdc25. These results suggest that s-pub1 may directly ubiquitinate cdc25 in vivo. Human pub1 was found to complement the loss of the fission yeast gene and restore the cell size at mitosis to wild-type. This indicates that h-pub1 is a biologically active, functional homolog of yeast pub1.

For convenience, certain terms employed in the specification, examples, and appended claims are collected here.

The terms peptides, proteins and polypeptides are used interchangeably herein.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

As used herein, the term "gene" or "recombinant gene" refers to a nucleic acid comprising an open reading frame encoding a pub polypeptide of the present invention, including both exon and (optionally) intron sequences. A "recombinant gene" refers to nucleic acid encoding a pub polypeptide and comprising pub-encoding exon sequences, though it may optionally include intron sequences which are either derived from a chromosomal pub gene or from an unrelated chromosomal gene. An exemplary recombinant genes encoding the subject pub poypeptides is represented by any of SEQ ID Nos: 1, 3 or 5. The term "intron" refers to a DNA sequence present in a given pub gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a pub polypeptide of the present invention or where anti-sense expression occurs from the transferred gene, the expression of a naturally-occurring form of the pub protein is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant pub gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the pub protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of a urogenital origin, e.g. renal cells, or cells of a neural origin, e.g. neuronal cells. The term also covers so-called "leaky" promoters, which regulate expression of a selected DNA primarily in one tissue, but cause expression in other tissues as well.

As used herein, a "transgenic animal" is any animal, preferably a non-human mammal, a bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of a pub protein, e.g. either agonistic or antagonistic forms. However, transgenic animals in which the recombinant pub gene is silent are also contemplated, as for example, the FLP or CRE recombinase dependent constructs described below. The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding, for example, embryogenesis and tissue patterning. The term "chimeric animal" is used herein to refer to animals in which the recombinant gene is found, or in which the recombinant is expressed in some but not all cells of the animal. The term "tissue-specific chimeric animal" indicates that the recombinant pub gene is present and/or expressed in some tissues but not others.

As used herein, the term "transgene" means a nucleic acid sequence (encoding, e.g., a pub polypeptide), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a pub polypeptide" may thus refer to one or more genes within a particular individual. Moreover, certain differences in nucleotide sequences may exist between individual organisms, which are called alleles.

Such allelic differences may or may not result in differences in amino acid sequence of the encoded polypeptide yet still encode a protein with the same biological activity.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding the subject pub polypeptide with a second amino acid sequence defining a domain foreign to and not substantially homologous with any domain of the pub polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

The term "evolutionarily related to", with respect to nucleic acid sequences encoding pub, refers to nucleic acid sequences which have arisen naturally in an organism, including naturally occurring mutants. The term also refers to nucleic acid sequences which, while derived from a naturally occurring pub genes, have been altered by mutagenesis, as for example, combinatorial mutagenesis described below, yet still encode polypeptides which have at least one activity of a pub protein.

The term "isolated" as also used herein with respect to nucleic acids, such as DNA or RNA, refers to molecules separated from other DNAs, or RNAs, respectively, that are present in the natural source of the macromolecule. For example, isolated nucleic acids encoding the subject pub polypeptides preferably include no more than 10 kilobases (kb) of nucleic acid sequence which naturally immediately flanks particular pub gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As used herein, a "mitotic activating tyrosine phosphatase" refers to a phosphatase which is involved in one or more aspects of cell-cycle progression, e.g., progression from $G_0$ to $G_1$, $G_1$ to S phase and/or $G_2$ to M phase.

The term "E3-like complex" refers to a protein complex including a pub protein ubiquitin ligase and other associated proteins, which protein complex augments or otherwise facilitates the ubiquitination of a protein. In preferred embodiments, the E3-like complex includes a pub protein which is capable of ubiquitinating the mitotic tyrosine phosphatase cdc25.

As used herein "E3-like" or "pub-dependent ubiquitination" refers to the conjugation of ubiquitin to a protein by a mechanism which requires a pub ligase activity.

The term "substrate protein" or "target protein" refers to a protein, preferably a cellular protein, which can be ubiquitinated by a pub-dependent reaction pathway.

The term "whole lysate" refers to a cell lysate which has not been manipulated, e.g. either fractionated, depleted or charged, beyond the step of merely lysing the cell to form the lysate. The term whole cell lysate does not, however, include lysates derived from cells which produce recombinant forms of one or more of the proteins required to constitute a ubiquitin-conjugating system for pub-dependent ubiquitination of a target protein.

The term "charged lysate" refers to cell lysates which have been spiked with exogenous, e.g., purified, semi-purified and/or recombinant, forms of one or more components of a pub-dependent ubiquitin-conjugating system, or the target protein thereof. The lysate can be charged after the whole cells have been harvested and lysed, or alternatively, by virtue of the cell from which the lysate is generated expressing a recombinant form of one or more of the conjugating system components.

The term "semi-purified cell extract" or, alternatively, "fractionated lysate", as used herein, refers to a cell lysate which has been treated so as to substantially remove at least one component of the whole cell lysate, or to substantially enrich at least one component of the whole cell lysate. "Substantially remove", as used herein, means to remove at least 10%, more preferably at least 50%, and still more preferably at least 80%, of the component of the whole cell lysate. "Substantially enrich", as used herein, means to enrich by at least 10%, more preferably by at least 30%, and still more preferably at least about 50%, at least one component of the whole cell lysate compared to another component of the whole cell lysate. The component which is removed or enriched can be a component of a ubiquitin-conjugation pathway, e.g., ubiquitin, a target protein, an E1, an E2, an E3-like complex, a cdc25 phosphatase, and the like, or it can be a component which can interfere with a ubiquitin-binding assay, e.g., a protease.

The term "semi-purified cell extract" is also intended to include the lysate from a cell, when the cell has been treated so as to have substantially more, or substantially less, of a given component than a control cell. For example, a cell which has been modified (by, e.g., recombinant DNA techniques) to produce none (or very little) of a component of a ubiquitin-conjugation pathway, will, upon cell lysis, yield a semi-purified cell extract.

The term "component of a ubiquitin-conjugation pathway", as used herein, refers to a component which can participate in the ubiquitination of a target protein either in vivo or in vitro. Exemplary components of a ubiquitin-conjugation pathway include ubiquitin, an E1, an E2, an E3-like complex, a target protein, and the like.

By "semi-purified", with respect to protein preparations, it is meant that the proteins have been previously separated from other cellular or viral proteins. For instance, in contrast to whole cell lysates, the proteins of reconstituted conjugation system, together with the target protein, can be present in the mixture to at least 50% purity relative to all other proteins in the mixture, more preferably are present at at least 75% purity, and even more preferably are present at 90–95% purity.

The term "purified protein", with respect to components of the ubiquitination pathway, refers to a preparation of a protein or proteins which are preferably isolated from, or otherwise substantially free of, other proteins normally associated with the protein(s) in a cell or cell lysate. The term "substantially free of other cellular proteins" (also refered to herein as "contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to the component proteins preparations used to generate the reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either protein in its native state (e.g. as a part of a cell), or as part of a cell lysate, or that have been separated into components (e.g., in an acrylamide gel) but not obtained either as pure (e.g. lacking contaminating proteins) substances or solutions. The term isolated as used herein also refers to a component protein that is substantially free of cellular material or culture medium when produced by recombinant DNA techniques, or chemical precursors or other chemicals when chemically synthesized.

As described below, one aspect of the invention pertains to isolated nucleic acid having a nucleotide sequence encoding a pub protein, and/or equivalents of such nucleic acids. The term nucleic acid as used herein is intended to include fragments and equivalents. The term equivalent is understood to include nucleotide sequences encoding functionally equivalent pub proteins or functionally equivalent polypeptides which, for example, retain the ability to bind to a mitotic activating tyrosine phosphatase. Equivalent nucleotide sequences will include sequences that differ by one or more nucleotide substitutions, additions or deletions, such as allelic variants; and will, therefore, include sequences that differ from the nucleotide sequence of the gene encoding h-pub1 shown in SEQ ID No: 1 or the gene encoding s-pub1 shown in SEQ ID No: 3 or the h-pub2 sequence shown in SEQ ID No. 5, due to the degeneracy of the genetic code. Equivalents will also include nucleotide sequences that hybridize under stringent conditions (i.e., equivalent to about 20–27° C. below the melting temperature ($T_m$) of the DNA duplex formed in about 1M salt) to the nucleotide sequence of pub gene represented in SEQ ID No: 1, SEQ ID No: 3 or SEQ ID No. 5. In one embodiment, equivalents will further include nucleic acid sequences derived from and evolutionarily related to, a nucleotide sequences shown in SEQ ID No: 1, SEQ ID No: 3 or SEQ ID No. 5.

Moreover, it will be generally appreciated that, under certain circumstances, it may be advantageous to provide homologs of the subject pub proteins, which homologs function in a limited capacity as one of either an agonists (mimetic) or an antagonist in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of a pub proteins's biological activities. For instance, antagonistic homologs can be generated which interfere with the ability of the wild-type ("authentic") pub1 protein to associate with cdc25 phosphatase, but which do not substantially interfere with the formation of complexes between pub1 and other cellular proteins, such as may be involved in other regulatory mechanisms of the cell.

Polypeptides referred to herein as pub polypeptides preferably have an amino acid sequence corresponding to all or a portion of the pub1 amino acid sequence shown in SEQ ID No. 2 or in SEQ ID No.4, or the pub2 amino acid sequence shown in SEQ ID No. 6, or are homologous with one of these proteins, such as other human paralogs, or mammalian orthologs. In general, the biological activity of a pub polypeptide will be characterized as including the ability to transfer an ubiquitin molecule form the relevant ubiquitin conjugating enzyme (UBC) to a lysine residue of its target through a pub ubiquitin thioester intermediate; and an ability to translocate to specific phospholipid membranes in the presence of calcium. The above notwithstanding, the biological activity of a pub polypeptide may be characterized by one or more of the following attributes: an ability to regulate the cell-cycle of an eukaryotic cell, especially a mammalian cell (e.g., of a human cell), or a yeast cell such as a Schizosaccharomyces cell; an ability to modulate proliferation/cell growth of a eukaryotic cell; an ability to modulate entry of a mammalian or yeast cell into M phase; an ability to ubiquitinate a cell-cycle regulator, e.g. a mitotic activating tyrosine phosphatase, e.g. cdc25. Such activities may be manifested by the ability to control the steady state level of cdc25 phosphatase, and thus to control the degree of dephosphorylation of a cyclin dependent kinase. The pub polypeptides of the present invention may also function to modulate differentiation of cells/tissue. The subject polypeptides of this invention may also be capable of modulating cell growth or proliferation by influencing the action of other cellular proteins. A pub polypeptide can be a specific agonist of the function of the wild-type form of the protein, or can be a specific antagonist, such as a catalytically inactive mutant. Other biological activities of the subject pub proteins are described herein, or will be reasonably apparent to those skilled in the art in light of the present disclosure.

In one embodiment, the nucleic acid of the invention encodes a polypeptide which is an agonist or antagonist of the naturally occurring h-pub1 protein and comprises an amino acid sequence identical or homologous to the amino acid sequence represented in SEQ ID No. 2. Preferred nucleic acids encode a polypeptide at least 60% homologous, more preferably 70% homologous and most preferably 80% homologous with an amino acid sequence shown in SEQ ID No. 2. Nucleic acids which encode polypeptides having an activity of a p19 protein and having at least about 90%, more preferably at least about 95%, and most preferably at least about 98–99% homology with a sequence shown in SEQ ID No. 2 are also within the scope of the invention. Preferably, the nucleic acid is a cDNA molecule comprising at least a portion of the nucleotide sequence encoding an h-pub1 protein shown in SEQ ID No. 2. A preferred portion of the cDNA molecule designated by SEQ ID No. 1 includes the coding region of the molecule.

In one embodiment, the nucleic acid of the invention encodes a polypeptide which is an agonist or antagonist of the naturally occurring h-pub2 protein and comprises an amino acid sequence identical or homologous to the amino acid sequence represented in SEQ ID No. 6. Preferred nucleic acids encode a polypeptide at least 60% homologous, more preferably 70% homologous and most preferably 80% homologous with an amino acid sequence shown in SEQ ID No. 6. Nucleic acids which encode polypeptides having an activity of a p19 protein and having at least about 90%, more preferably at least about 95%, and most preferably at least about 98–99% homology with a sequence shown in SEQ ID No. 6 are also within the scope of the invention. Preferably, the nucleic acid is a cDNA molecule comprising at least a portion of the nucleotide sequence encoding an h-pub2 protein shown in SEQ ID No. 6. A preferred portion of the cDNA molecule designated by SEQ ID No. 5 includes the coding region of the molecule.

In another embodiment, the nucleic acid of the invention encodes a polypeptide which is an agonist or antagonist of the naturally occurring s-pub1 protein and comprises an amino acid sequence identical or homologous to the amino acid sequence represented in SEQ ID No. 4. Preferred nucleic acids encode a polypeptide at least 60% homologous, more preferably 70% homologous and most preferably 80% homologous with an amino acid sequence shown in SEQ ID No. 4. Nucleic acids which encode polypeptides having an activity of an s-pub1 protein and having at least about 90%, more preferably at least about 95%, and most preferably at least about 98–99% homology with a sequence shown in SEQ ID No. 4 are also within the scope of the invention. Preferably, the nucleic acid is a cDNA molecule comprising at least a portion of the nucleotide sequence encoding an s-pub1 protein shown in SEQ ID No. 4. A preferred portion of the cDNA molecule shown in SEQ ID No. 3 includes the coding region of the molecule.

Isolated nucleic acids which differ from the nucleotide sequences shown in SEQ ID No: 1, SEQ ID No: 3 or SEQ ID No. 5 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject pub proteins will exist among mammalian cells. One skilled in the art will appreciate that these variations in one or more nucleotides (up to about 3–4% of the nucleotides) of the nucleic acids encoding a particular pub protein may exist among individuals of a given species due to natural allelic variation. Any and all such nucleotide variations and resulting amino acid polymorphisms are within the scope of this invention.

Fragments of the nucleic acid encoding a biologically active portion of the subject pub proteins are also within the scope of the invention. As used herein, a fragment of the nucleic acid encoding an active portion of a pub protein refers to a nucleotide sequence having fewer nucleotides than the nucleotide sequence encoding the full length amino acid sequence of, for example, the pub protein represented in SEQ ID Nos: 2, 4 or 6, and which encodes a polypeptide which retains at least a portion of the biological activity of the full-length protein as defined herein, or alternatively, which is functional as an antagonist of the biological activity of the full-length protein. For example, such fragments include, as appropriate to the full-length protein from which they are derived, a polypeptide containing a CaLB domain and capable of associating with a phospholipid membrane in a calcium dependent manner, an ATP binding motif, and/or a catalytically active domain, e.g., a hect domain.

Nucleic acids within the scope of the invention may also contain linker sequences, modified restriction endonuclease sites and other sequences useful for molecular cloning, expression or purification of such recombinant polypeptides.

As indicated by the examples set out below, a nucleic acid encoding a pub polypeptide may be obtained from mRNA or genomic DNA present in any of a number of mammalian cells in accordance with protocols described herein, as well as those generally known to those skilled in the art. A cDNA encoding a pub polypeptide, for example, can be obtained by isolating total mRNA from a cell, e.g. a mammalian cell, e.g. a human cell. Double stranded cDNAs can then be prepared from the total mRNA, and subsequently inserted into a suitable plasmid or bacteriophage vector using any one of a number of known techniques. A gene encoding a pub protein can also be cloned using established polymerase chain reaction techniques in accordance with the nucleotide sequence information provided by the invention.

Another aspect of the invention relates to the use of the isolated nucleic acid in "antisense" therapy. As used herein, antisense therapy refers to administration or in situ generation of oligonucleotide probes or their derivatives which specifically hybridize (e.g. binds) under cellular conditions with the cellular mRNA and/or genomic DNA encoding one of the subject pub proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, antisense therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a pub protein. Alternatively, the antisense construct is an oligonucleotide probe which is generated ex vivo and which, when introduced into the cell causes inhibition of expression by hybridizing with the mRNA and/or genomic sequences encoding a pub protein. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al., (1988) *Biotechniques* 6:958–976; and Stein et al., (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of modes of administration, including systemic and topical or localized administration. Techniques and formulations generally may be found in *Remmington's Pharmaceutical Sciences,* Meade Publishing Co., Easton, Pa. For systemic administration, injection is preferred, including intramuscular, intravenous, intraperitoneal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind.

In another aspect of the invention, the subject nucleic acid is provided in an expression vector comprising a nucleotide sequence encoding a subject pub polypeptide and operably linked to at least one regulatory sequence. Operably linked is intended to mean that the nucleotide sequence is linked to a regulatory sequence in a manner which allows expression of the nucleotide sequence. Regulatory sequences are art-recognized and are selected to direct expression of the polypeptide having an activity of a pub protein. Accordingly, the term regulatory sequence includes promoters, enhancers and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding the pub proteins of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda , the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

As will be apparent, the subject gene constructs can be used to cause expression of the subject pub polypeptides in cells propagated in culture, e.g. to produce proteins or polypeptides, including fusion proteins or polypeptides, for purification.

In addition, recombinant expression of the subject pub polypeptides in cultured cells can be useful for controlling differentiation states of cells in vitro, for instance, by controlling the steady state level of activation of cdc25 and thus, the activation of a CDK, e.g., cdc2. To illustrate, in vitro neuronal culture systems have proved to be fundamental and indispensable tools for the study of neural development, as well as the identification of neurotrophic factors. Once a neuronal cell has become terminally-differentiated, it typically will not change to another terminally differentiated cell-type. However, neuronal cells can nevertheless sometimes lose their differentiated state. This is commonly observed when they are grown in culture from adult tissue, and when they form a blastema during regeneration. By preventing the activation of an M-phase CDK, certain of the pub homologs (presumably agonist forms) can prevent mitotic progression and hence provide a means for ensuring an adequately restrictive environment in order to maintain neuronal cells at various stages of differentiation, and can be employed, for instance, in cell cultures designed to test the specific activities of trophic factors. Other tissue culture systems which require maintenance of differentiation will be readily apparent to those skilled in the art. In this respect, each of the agonist and antagonist of pub activation can be used for ex vivo tissue generation, as for example, to enhance the generation of prosthetic tissue devices for implantation.

To further illustrate, hyper-proliferative cells can be created by antagonizing the activity of the wild-type pub protein, such as by expression of antagonistic homologs, e.g. dominant negative mutants, antisense constructs, or treatment with agents able to disrupt binding of a pub protein with, for example, a cdc25 phosphatase. Pub antagonists provides a method of transforming mammalian cells to be used as in vivo systems to characterize mitotic inhibitors. Conversely, a hypo-proliferative cell can be created by potentiating the activity of the wild type pub protein by expression of agonist homologs or treatment with agents that enhance the binding of pub to cdc25, and thus reduce the level of cdc25 present in a cell.

Moreover, antagonizing the activity of the wild-type pub proteins, such as by expression of antagonistic homologs, antisense constructs, or treatment with agents able to disrupt binding of pub proteins with a cdc25 protein, can be utilized in diagnostic assays to determine if a cell's growth is no longer dependent on the regulatory function of cdc25 and pub proteins, e.g. in determining the phenotype of a transformed cell. To illustrate, a sample of cells from the tissue can be obtained from a patient and dispersed in appropriate cell culture media, a portion of the cells in the sample can be caused to express a recombinant pub protein, e.g. by transfection with an expression vector, and subsequent growth of the cells assessed. The ability of cells to proliferate despite expression of an agonistic pub protein is indicative of a lack of dependence on cell regulatory pathways which include the pub protein, e.g. a cdc25/cdk-dependent pathway(s). Depending on the nature of the tissue of interest, the sample can be in the form of cells isolated from, for example, a blood sample, an exfoliated cell sample, a fine needle aspirant sample, or a biopsied tissue sample. Where the initial sample is a solid mass, the tissue sample can be minced or otherwise dispersed so that cells can be cultured, as is known in the art. Such knowledge can have both prognostic and therapeutic benefits.

Thus, another aspect of the present invention concerns recombinant pub proteins which have at least one biological activity of a naturally occurring pub protein, or which are naturally occurring mutants thereof. The term "recombinant protein" refers to a protein of the present invention which is produced by recombinant DNA techniques, wherein generally DNA encoding the pub protein is inserted into a suitable expression vector which is in turn used to transform a host cell to produce the heterologous protein. Moreover, the phrase "derived from", with respect to a recombinant gene encoding the recombinant pub protein, is meant to include within the meaning of "recombinant protein" those proteins having an amino acid sequence of a native pub protein, or an amino acid sequence similar thereto which is generated by mutations including substitutions and deletions of a naturally occurring pub protein. To illustrate, recombinant proteins preferred by the present invention, in addition to native pub proteins, are those recombinantly produced proteins which are at least 60% homologous, more preferably 70% homologous and most preferably 80% homologous with an amino acid sequence shown in SEQ ID No. 2, SEQ ID No. 4 or SEQ ID No. 6. Polypeptides having an activity of a pub protein, such as the ability to transfer an ubiquitin molecule form the relevant ubiquitin conjugating enzyme (UBC) or E2 to a lysine residue of its target through a pub ubiquitin thioester intermediate, and having at least about 90%, more preferably at least about 95%, and most preferably at least about 98–99% homology with a sequence shown in SEQ ID No. 2, SEQ ID No. 4 or SEQ ID No. 6 are also within the scope of the invention. Thus, the present invention pertains to recombinant pub proteins which are encoded by genes derived from an eukaryotic cell and which have amino acid sequences evolutionarily related to a pub protein represented by one of SEQ ID No. 2, SEQ ID No. 4 or SEQ ID No. 6, wherein "evolutionarily related to", refers to pub proteins having amino acid sequences which have arisen naturally (e.g. by allelic variance or by differential splicing), as well as mutational variants of pub proteins which are derived, for example, by combinatorial mutagenesis.

This invention also pertains to a host cell transfected with a recombinant pub gene in order to express a polypeptide having an activity of a pub protein. The host cell may be any prokaryotic or eukaryotic cell. For example, a pub protein of the present invention may be expressed in bacterial cells such as *E. coli*, insect cells (baculovirus), yeast, or mammalian cells. Other suitable host cells are known to those skilled in the art.

Accordingly, the present invention further pertains to methods of producing the subject pub proteins. For example, a host cell transfected with an expression vector encoding a pub polypeptide can be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated. A cell culture includes host cells, media and other byproducts. Suitable media for cell culture are well known in the art. The polypeptide can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the pub protein. In a preferred embodiment, the pub protein is a fusion protein containing a domain which facilitates its purification, such as a pub-GST fusion protein.

Thus, a nucleotide sequence derived from the cloning of the pub proteins described in the present invention, encoding all or a selected portion of the protein, can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known cell-cycle regulatory proteins, e.g. p53, cyclins, RB, p16, ubc4, E6-AP, and the like. Similar procedures, or modifications thereof, can be employed to prepare recombinant pub proteins, or portions thereof, by microbial means or tissue-culture technology in accord with the subject invention.

The recombinant pub protein can be produced by ligating the cloned gene, or a portion thereof, into a vector suitable for expression in either prokaryotic cells, eukaryotic cells, or both. Expression vehicles for production of a recombinant pub protein include plasmids and other vectors. For instance, suitable vectors for the expression of pub include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al., (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant pub protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a carboxy terminal fragment of the full-length pub proteins is desired, i.e. a truncation mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., (1987) *J. Bacteriol.* 169:751–757) and *Salmonella typhimurium* and its in vitro activity has been demonstrated on recombinant proteins (Miller et al., (1987) *Proc. Natl. Acad. Sci. USA* 84:2718–1722). Therefore, removal of an N-terminal methionine, if desired, can be achieved either in vivo by expressing such recombinant polypeptides in a host which produces MAP (e.g., *E. coli* or CM89 or *S. cerevisiae*), or in vitro by use of purified MAP (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of the pub protein. For example, the VP6 capsid protein of rotavirus can be used as an immunologic carrier protein for portions of polypeptide, either in the monomeric form or in the form of a viral particle. The nucleic acid sequences corresponding to the portion of the pub protein to which antibodies are to be raised can be incorporated into a fusion gene construct which includes coding sequences for a late vaccinia virus structural protein to produce a set of recombinant viruses expressing fusion proteins comprising a portion of the protein as part of the virion. The Hepatitis B surface antigen can also be utilized in this role as well. Similarly, chimeric constructs coding for fusion proteins containing a portion of a pub protein and the poliovirus capsid protein can be created to enhance immunogenicity (see, for example, EP Publication No. 0259149; and Evans et al., (1989) *Nature* 339:385; Huang et al., (1988) *J. Virol.* 62:3855; and Schlienger et al., (1992) *J. Virol.* 66:2).

The Multiple Antigen Peptide system for peptide-based immunization can be utilized, wherein a desired portion of a pub protein is obtained directly from organo-chemical synthesis of the peptide onto an oligomeric branching lysine core (see, for example, Posnett et al., (1988) *JBC* 263:1719 and Nardelli et al., (1992) *J. Immunol.* 148:914). Antigenic determinants of the pub protein can also be expressed and presented by bacterial cells.

In addition to utilizing fusion proteins to enhance immunogenicity, it is widely appreciated that fusion proteins can also facilitate the expression of proteins. For example, the pub protein of the present invention can be generated as a glutathione-S-transferase (GST) fusion proteins. Such GST fusion proteins can be used to simply purification of the pub protein, such as through the use of glutathione-derivatized matrices (see, for example, *Current Protocols in Molecular Biology*, eds. Ausubel et al., (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a $Ni^{2+}$ metal resin. The purification leader sequence can then be subsequently removed by treatment with enterokinase to provide the purified pub protein (e.g., see Hochuli et al., (1987) *J. Chromatography* 411:177; and Janknecht et al., *Proc. Natl. Acad. Sci. USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

The present invention also makes available isolated and/or purified forms of the subject pub polypeptides, which are isolated from, or otherwise substantially free of other intracellular proteins, especially cell-cycle regulatory proteins, e.g. cdc25 phosphatase or E2 enzymes, which might normally be associated with the pub protein. The term "substantially free of other cellular proteins" (also referred to herein as "contaminating proteins") is defined as encompassing, for example, pub preparations comprising less than 20% (by dry weight) contaminating protein, and preferably comprises less than 5% contaminating protein. Functional forms of the pub polypeptide can be prepared, for the first time, as purified preparations by using a cloned gene as described herein. By "purified", it is meant, when referring to a polypeptide, that the indicated molecule is present in the substantial absence of other biological macromolecules, such as other proteins (particularly other cell-cycle proteins such as cdc25 phosphatase, as well as other contaminating proteins). The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

The subject polypeptides can also be provided in pharmaceutically acceptable carriers for formulated for a variety of modes of administration, including systemic and topical or localized administration. Techniques and formulations generally may be found in *Remmington's Pharmaceutical Sciences*, Meade Publishing Co., Easton, Pa. In an exemplary embodiment, the pub polypeptide is provided for transmucosal or transdermal delivery. For such administration, penetrants appropriate to the barrier to be permeated are used in the formulation with the polypeptide. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

Another aspect of the invention relates to polypeptides derived from the full-length pub protein. Isolated peptidyl portions of the subject pub protein can be obtained by screening polypeptides recombinantly produced from the corresponding fragment of the nucleic acid encoding such polypeptides. In addition, fragments can be chemically synthesized using techniques known in the art such as conventional Merrifield solid phase f-Moc or t-Boc chemistry. For example, pub protein can be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of, for example, cdc25 degradation, such as by microinjection assays. In an illustrative embodiment, peptidyl portions of pub protein can tested for cdc25-binding activity, as well as inhibitory ability, by expression as, for example, thioredoxin fusion proteins, each of which contains a discrete fragment of the pub protein (see, for example, U.S. Pat. Nos. 5,270,181 and 5,292,646; and PCT publication WO94/02502).

It is also possible to modify the structure of the subject pub proteins for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of the pub polypeptides described in more detail herein. Such modified polypeptides can be produced, for instance, by amino acid substitution, deletion, or addition.

For instance, it is reasonable to expect, for example, that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide= asparagine, glutamine; and (6) sulfur-containing=cysteine and methionine, (see, for example, *Biochemistry*, 2nd ed., Ed. by L. Stryer, W. H. Freeman and Co., 1981). Whether a change in the amino acid sequence of a polypeptide results in a functional homolog can be readily determined by assessing the ability of the variant polypeptide to produce a response in cells in a fashion similar to the wild-type protein. For instance, such variant forms of pub can be assessed for their ability to bind to a cdc25 phosphatase of the present invention or other cellular protein. Polypeptides in which more than one replacement has taken place can readily be tested in the same manner.

This invention further contemplates a method of generating sets of combinatorial mutants of the subject pub proteins, as well as truncation mutants, and is especially useful for identifying potential variant sequences (e.g. homologs) that are functional in binding to a regulatory protein, especially cdc25 phosphatase. The purpose of screening such combinatorial libraries is to generate, for example, pub homologs which can act as either agonists or antagonist, or alternatively, which possess novel activities all together. To illustrate, homologs can be engineered by the present method to provide more efficient binding to cdc25 phosphatase, yet have a significantly reduced binding affinity for other cell-cycle regulatory proteins relative to the naturally-occurring form of the protein. Thus, combinatorially-derived homologs can be generated which have a selective potency relative to a naturally occurring pub protein. Such proteins, when expressed from recombinant DNA constructs, can be used in gene therapy protocols.

Likewise, mutagenesis can give rise to homologs which have intracellular half-lives dramatically different than the corresponding wild-type protein. For example, the altered protein can be rendered either more stable or less stable to proteolytic degradation or other cellular process which result in destruction of, or otherwise inactivation of the pub protein. Such homologs, and the genes which encode them, can be utilized to alter the envelope of pub expression by modulating the half-life of the protein. For instance, a short half-life can give rise to more transient biological effects and, when part of an inducible expression system, can allow tighter control of recombinant pub protein levels within the cell. As above, such proteins, and particularly their recombinant nucleic acid constructs, can be used in gene therapy protocols.

In similar fashion, pub homologs can be generated by the present combinatorial approach to act as antagonists, in that they are able to interfere with the ability of the corresponding wild-type protein to regulate cell proliferation.

In a representative embodiment of this method, the amino acid sequences for a population of pub protein homologs are aligned, preferably to promote the highest homology possible. Such a population of variants can include, for example, homologs from one or more species, or homologs from the same species but which differ due to mutation. Amino acids which appear at each position of the aligned sequences are selected to create a degenerate set of combinatorial sequences. In a preferred embodiment, the combinatorial library is produced by way of a degenerate library of genes encoding a library of polypeptides which each include at least a portion of potential pub protein sequences. For instance, a mixture of synthetic oligonucleotides can be enzymatically ligated into gene sequences such that the degenerate set of potential pub nucleotide sequences are expressible as individual polypeptides, or alternatively, as a set of larger fusion proteins (e.g. for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential pub sequences. The synthesis of degenerate oligonucleotides is well known in the art (see for example, Narang, S A (1983) *Tetrahedron* 39:3; Itakura et al., (1981) *Recombinant DNA, Proc.* 3rd Cleveland Sympos. Macromolecules, ed. A G Walton, Amsterdam: Elsevier pp273–289; Itakura et al., (1984) *Annu. Rev. Biochem.* 53:323; Itakura et al., (1984) *Science* 198:1056; Ike et al., (1983) *Nucleic Acid Res.* 11:477. Such techniques have been employed in the directed evolution of other proteins (see, for example, Scott et al., (1990) *Science* 249:386–390; Roberts et al., (1992) *Proc. Natl. Acad. Sci. USA* 89:2429–2433; Devlin et al., (1990) *Science* 249: 404–406; Cwirla et al., (1990) *Proc. Natl. Acad. Sci. USA* 87: 6378–6382; as well as U.S. Pat. Nos. 5,223,409, 5,198,346, and 5,096,815).

Alternatively, other forms of mutagenesis can be utilized to generate a combinatorial library. For example, pub homologs (both agonist and antagonist forms) can be generated and isolated from a library by screening using, for example, alanine scanning mutagenesis and the like (Ruf et al., (1994) *Biochemistry* 33:1565–1572; Wang et al., (1994) *J. Biol. Chem.* 269:3095–3099; Balint et al., (1993) *Gene* 137:109–118; Grodberg et al., (1993) *Eur. J. Biochem.* 218:597–601; Nagashima et al., (1993) *J. Biol. Chem.* 268:2888–2892; Lowman et al., (1991) *Biochemistry* 30:10832–10838; and Cunningham et al., (1989) *Science* 244:1081–1085), by linker scanning mutagenesis (Gustin et al., (1993) *Virology* 193:653–660; Brown et al., (1992) *Mol. Cell Biol.* 12:2644–2652; McKnight et al., (1982) *Science* 232:316); by saturation mutagenesis (Meyers et al., (1986) *Science* 232:613); by PCR mutagenesis (Leung et al., (1989) *Method Cell Mol Biol* 1:11–19); or by random mutagenesis (Miller et al., (1992) A Short Course in Bacterial Genetics, CSHL Press, Cold Spring Harbor, N.Y.; and Greener et al., (1994) *Strategies in Mol Biol* 7:32–34). Linker scanning matagenesis, particularly in a combinatorial setting, is on attractive method for identifying truncated (bioactive) forms of the pub proteins.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of pub homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In an illustrative embodiment of a screening assay, candidate pub combinatorial gene products, are displayed on the surface of a cell, and the ability of particular cells or viral particles to bind the cdc25 polypeptide, or other binding partners of pub via this gene product is detected in a "panning assay". For instance, the pub gene library can be cloned into the gene for a surface membrane protein of a bacterial cell (Ladner et al., WO 88/06630; Fuchs et al., (1991) *Bio/Technology* 9:1370–1371; and Goward et al., (1992) *TIBS* 18:136–140), and the resulting fusion protein detected by panning, e.g. using a fluorescently labeled molecule which binds the pub protein, e.g. FITC-cdc25, to score for potentially functional homologs. Cells can be visually inspected and separated under a fluorescence microscope, or, where the morphology of the cell permits, separated by a fluorescence-activated cell sorter. While the preceding description is directed to embodiments exploiting the interaction between pub and a cdc25 polypeptide, it will be understood that similar embodiments can be generated using, for example, a pub polypeptide displayed on the surface of a cell and examining the ability of those pub-expressing cells to bind other binding partners of pub.

In similar fashion, the gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and fl are most often used in phage display libraries, as either of the phage gIII or gVIII coat proteins can be used to generate fusion proteins without disrupting the ultimate packaging of the viral particle (Ladner et al., PCT publication WO 90/02909; Garrard et al., PCT publication WO 92/09690; Marks et al., (1992) *J. Biol. Chem.* 267:16007–16010; Griffiths et al., (1993) *EMBO J.* 12:725–734; Clackson et al., (1991) *Nature* 352:624–628; and Barbas et al., (1992) *Proc. Natl. Acad. Sci. USA* 89:4457–4461).

In an illustrative embodiment, the recombinant phage antibody system (RPAS, Pharmacia Catalog number 27-9400-01) can be easily modified for use in expressing and screening pub combinatorial libraries of the present invention. For instance, the pCANTAB 5 phagemid of the RPAS kit contains the gene which encodes the phage gIII coat protein. The pub combinatorial gene library can be cloned into the phagemid adjacent to the gIII signal sequence such that it will be expressed as a gIII fusion protein. After ligation, the phagemid is used to transform competent *E. coli* TG1 cells. Transformed cells are subsequently infected with M13KO7 helper phage to rescue the phagemid and its candidate pub gene insert. The resulting recombinant phage contain phagemid DNA encoding a specific candidate pub protein, and display one or more copies of the corresponding fusion coat protein. The phage-displayed candidate proteins which are capable of, for example, binding cdc25, are selected or enriched by panning. For instance, the phage library can be panned on glutathione immobilized cdc25-GST fusion proteins, and unbound phage washed away from the cells. The bound phage is then isolated, and if the recombinant phage express at least one copy of the wild type gIII coat protein, they will retain their ability to infect *E. coli*. Thus, successive rounds of reinfection of *E. coli*, and panning will greatly enrich for pub homologs which can then be screened for further biological activities in order to differentiate agonists and antagonists.

Consequently, the invention also provides for reduction of the subject pub proteins to generate mimetics, e.g. peptide or non-peptide agents, which are able to mimic binding of the authentic protein to another cellular partner. Such mutagenic techniques as described above, as well as the thioredoxin system, are also particularly useful for mapping the determinants of a pub protein which participate in protein-protein interactions involved in, for example, binding of the subject proteins to each other. To illustrate, the critical residues of a pub protein which are involved in molecular recognition of cdc25 can be determined and used to generate pub-derived peptidomimetics which bind to cdc25, and by inhibiting pub binding, act to prevent activation of the kinase. By employing, for example, scanning mutagenesis to map the amino acid residues of pub which are involved in binding cdc25, peptidomimetic compounds can be generated which mimic those residues in binding to the kinase. For instance, non-hydrolyzable peptide analogs of such residues can be generated using benzodiazepine (e.g., see Freidinger et al., in *Peptides: Chemistry and Biology,* G. R. Marshall ed., ESCOM Publisher: Leiden, Netherlands, 1988), azepine (e.g., see Huffman et al., in *Peptides: Chemistry and Biology,* G. R. Marshall ed., ESCOM Publisher: Leiden, Netherlands, 1988), substituted gama lactam rings (Garvey et al., in *Peptides: Chemistry and Biology,* G. R. Marshall ed., ESCOM Publisher: Leiden, Netherlands, 1988), keto-methylene pseudopeptides (Ewenson et al., (1986) *J. Med. Chem.* 29:295; and Ewenson et al., in *Peptides: Structure and Function* (Proceedings of the 9th American Peptide Symposium) Pierce Chemical Co. Rockland, Ill., 1985), β-turn dipeptide cores (Nagai et al., (1985) *Tetrahedron Lett* 26:647; and Sato et al., (1986) *J Chem Soc Perkin Trans* 1:1231), and β-aminoalcohols (Gordon et al., (1985) *Biochem Biophys Res Commun* 126:419; and Dann et al., (1986) *Biochem Biophys Res Commun* 134:71).

Another aspect of the invention pertains to an antibody specifically reactive with a pub protein. For example, by using peptides based on the sequence of the subject human or yeast pub protein, anti-pub1 or anit-pub2 antisera or anti-pub1 or anti-pub2 monoclonal antibodies can be made using standard methods. A mammal such as a mouse, a hamster or rabbit can be immunized with an immunogenic form of the peptide (e.g., an antigenic fragment which is capable of eliciting an antibody response). Techniques for conferring immunogenicity on a protein or peptide include conjugation to carriers or other techniques well known in the art. For instance, a peptidyl portion of the protein represented by SEQ ID No. 2, SEQ ID No. 4 or SEQ ID No. 6 can be administered in the presence of adjuvant. The progress of immunization can be monitored by detection of antibody titers in plasma or serum. Standard ELISA or other immunoassays can be used with the immunogen as antigen to assess the levels of antibodies.

Following immunization, anti-pub antisera can be obtained and, if desired, polyclonal anti-pub antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature,* 256: 495–497). as the human B cell hybridoma technique (Kozbar et al., (1983) *Immunology Today,* 4: 72), and the EBV-hybridoma technique to produce human monoclonal antibodies (Cole et al., (1985) *Monoclonal Antibodies and Cancer Therapy,* Alan R. Liss, Inc. pp. 77–96). Hybridoma cells can be screened immunochemically for production of antibodies specifically reactive with the pub proteins and the monoclonal antibodies isolated.

The term antibody as used herein is intended to include fragments thereof which are also specifically reactive with an eukaryotic, e.g., mammalian pub protein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules, as well as single chain (scFv) antibodies.

Both monoclonal and polyclonal antibodies (Ab) directed against the subject pub protein, and antibody fragments such as Fab' and F(ab')$_2$, can be used to selectively block the action of individual pub proteins and allow the study of the cell-cycle or cell proliferation.

Another application of anti-pub antibodies is in the immunological screening of cDNA libraries constructed in expression vectors, such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a pub protein, such as proteins antigenically related to the h-pub1 protein of SEQ ID No. 2 or s-pub1 of SEQ ID No. 4 or the h-pub2 protein of SEQ ID No. 6, can then be detected with antibodies, as, for example, reacting nitrocellulose filters lifted from infected plates with an anti-pub antibody. Phage, scored by this assay, can then be isolated from the infected plate. Thus, pub homologs can be detected and cloned from other sources.

Antibodies which are specifically immunoreactive with a pub protein of the present invention can also be used in immunohistochemical staining of tissue samples in order to evaluate the abundance and pattern of expression of the protein. Anti-pub antibodies can be used diagnostically in immuno-precipitation and immuno-blotting to detect and evaluate levels of one or more pub proteins in tissue or cells isolated from a bodily fluid as part of a clinical testing procedure. Diagnostic assays using anti-pub antibodies, can include, for example, immunoassays designed to aid in early diagnosis of a neoplastic or hyperplastic disorder, e.g. the presence of cancerous cells in the sample, e.g. to detect cells in which alterations in expression levels of pub gene has occurred relative to normal cells.

In addition, nucleotide probes can be generated from the cloned sequence of the subject pub proteins which allow for histological screening of intact tissue and tissue samples for the presence of a pub protein encoding nucleic acids. Similar to the diagnostic uses of anti-pub protein antibodies, the use of probes directed to pub protein encoding mRNAs, or to genomic pub gene sequences, can be used for both predictive and therapeutic evaluation of allelic mutations which might be manifest in, for example, neoplastic or hyperplastic disorders (e.g. unwanted cell growth) or unwanted differentiation events.

Used in conjunction with anti-pub protein antibody immunoassays, the nucleotide probes can help facilitate the determination of the molecular basis for a developmental disorder which may involve some abnormality associated with expression (or lack thereof) of a pub protein. For instance, variation in pub protein synthesis can be differentiated from a mutation in the coding sequence.

Accordingly, the present method provides a method for determining if a subject is at risk for a disorder characterized by aberrant cell proliferation and/or differentiation. In preferred embodiments, method can be generally characterized as comprising detecting, in a sample of cells from the subject, the presence or absence of a genetic lesion characterized by at least one of (i) an alteration affecting the integrity of a gene encoding a pub protein, such as h-pub1 or h-pub2; or (ii) the mis-expression of the pub gene. To illustrate, such genetic lesions can be detected by ascertaining the existence of at least one of (i) a deletion of one or more nucleotides from a pub gene, (ii) an addition of one or more nucleotides to a pub gene, (iii) a substitution of one or more nucleotides of a pub gene, (iv) a gross chromosomal rearrangement of a pub gene, (v) a gross alteration in the level of a messenger RNA transcript of a pub gene, (vii) aberrant modification of a pub gene, such as of the methylation pattern of the genomic DNA, (vii) the presence of a non-wild type splicing pattern of a messenger RNA transcript of a pub gene, (viii) a non-wild type level of a pub protein, and (ix) inappropriate post-translational modification of a pub protein. As set out below, the present invention provides a large number of assay techniques for detecting lesions in a pub gene, and importantly, provides the ability to discern between different molecular causes underlying pub dependent aberrant cell growth, proliferation and/or differentiation.

Diagnostic assays are also similarly available for detecting s-pub1 genes, or homologs from other fungus, in order to detect mycotic infections.

In an exemplary embodiment, there is provided a nucleic acid composition comprising a (purified) oligonucleotide probe including a region of nucleotide sequence which is capable of hybridizing to a sense or antisense sequence of a pub gene, such as represented by any of SEQ ID Nos: 1, 3 or 5, or naturally occurring mutants thereof, or 5' or 3' flanking sequences or intronic sequences naturally associated with the subject pub genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., (1988) *Science* 241:1077–1080; and Nakazawa et al., (1944) *Proc. Natl. Acad. Sci. USA* 91:360–364), the later of which can be particularly useful for detecting point mutations in the pub gene. In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a pub gene under conditions such that hybridization and amplification of the pub gene (if present) occurs, and (iv) detecting the presence or absence of an amplification product, or detecting the size of the amplification product and comparing the length to a control sample.

In still another embodiment, the level of a pub protein can be detected by immunoassay. For instance, the cells of a biopsy sample can be lysed, and the level of a pub protein present in the cell can be quantitated by standard immunoassay techniques. In yet another exemplary embodiment, aberrant methylation patterns of a pub gene can be detected by digesting genomic DNA from a patient sample with one or more restriction endonucleases that are sensitive to methylation and for which recognition sites exist in the pub gene (including in the flanking and intronic sequences). See, for example, Buiting et al., (1994) *Human Mol Genet* 3:893–895. Digested DNA is separated by gel electrophoresis, and hybridized with probes derived from, for example, genomic or cDNA sequences. The methylation status of the pub gene can be determined by comparison of the restriction pattern generated from the sample DNA with that for a standard of known methylation.

Furthermore, the subject gene constructs described above can be utilized in diagnostic assays to determine if a cell's growth is no longer dependent on the regulatory function of a pub protein, e.g. in determining the phenotype of a transformed cell. To illustrate, a sample of cells from the tissue can be obtained from a patient and dispersed in appropriate cell culture media, a portion of the cells in the sample can be caused to express a recombinant pub protein, e.g. by transfection with an h-pub1, h-pub2 or s-pub1 expression vector, and subsequent growth of the cells assessed. The ability of cells to proliferate despite expression of the pub protein is indicative of a lack of dependence on cell regulatory pathways which include the pub protein. Depending on the nature of the tissue of interest, the sample can be in the form of cells isolated from, for example, a blood sample, an exfoliated cell sample, a fine needle aspirant sample, or a biopsied tissue sample. Where the initial sample is a solid mass, the tissue sample can be minced or otherwise dispersed so that cells can be cultured, as is known in the art. Such knowledge can have both prognostic and therapeutic benefits.

In yet another embodiment, a diagnostic assay is provided which detects the ability of a pub gene product, e.g., isolated from a biopsied cell, to bind to other cellular proteins. For instance, it will be desirable to detect h-pub1 mutants which bind with higher binding affinity a cdc25 phosphatase. Such mutants may arise, for example, from fine mutations, e.g., point mutants, which may be impractical to detect by the diagnostic DNA sequencing techniques or by the immunoassays described above. The present invention accordingly further contemplates diagnostic screening assays which generally comprise cloning one or more pub genes from the sample cells, and expressing the cloned genes under conditions which permit detection of an interaction between that recombinant gene product and a target protein, e.g., a cdc25.

As will be apparent from the description of the various drug screening assays set forth below, a wide variety of techniques can be used to determine the ability of a pub protein to bind to other cellular components, e.g., a cdc25 phosphatase such as cdc25A, cdc25B or cdc25C. These techniques can be used to detect mutations in a pub gene which give rise to mutant proteins with a higher or lower binding affinity for a cdc25 relative to the wild-type pub gene product. Conversely, by switching which of the cdc25 and pub protein is the "bait" and which is derived from the patient sample, the subject assay can also be used to detect cdc25 mutants which have a higher or lower binding affinity for a pub protein relative to a wild-type form of that cdc25.

In an exemplary embodiment, cdc25 (e.g. wild-type) can be provided as an immobilized protein (a "bait" or "target"), such as by use of GST fusion proteins and glutathione-treated microtitre plates. A pub gene (a "sample" gene) is amplified from cells of a patient sample, e.g., by PCR, cloned into an expression vector, and transformed into an appropriate host cell. The recombinantly produced pub protein is then contacted with the immobilized cdc25, e.g., as a lysate or a semi-purified preparation (see infra), the complex washed, and the amount of cdc25/pub complex determined and compared to a level of wild-type complex formed in a control. Detection can be by, for instance, an immunoassay using antibodies against the wild-type form of the pub protein, or by virtue of a label provided by cloning the sample pub gene into a vector which provides the protein as a fusion protein including a detectable tag. For example, a myc epitope can provided as part of a fusion protein with the sample pub gene. Such fusion proteins can, in addition to providing a detectable label, also permit purification of the sample pub protein from the lysate prior to application to the immobilized.

In yet another embodiment of the subject screening assay, the two hybrid assay can be used to detect mutations in either a pub gene or cdc25 gene which alter complex formation between those two proteins (see, for example, U.S. Pat. No. 5,283,317; PCT publication WO94/10300; Zervos et al., (1993) *Cell* 72:223–232; Madura et al., (1993) *J Biol Chem* 268:12046–12054; Bartel et al., (1993) *Biotechniques* 14:920–924; and Iwabuchi et al., (1993) *Oncogene* 8:1693–1696). Accordingly, the present invention provides a convenient method for detecting mutants of pub genes encoding proteins which are unable to physically interact with a cdc25 "bait" protein, which method relies on detecting the reconstitution of a transcriptional activator in a pub/cdc25-dependent fashion.

Still another aspect of the invention features transgenic non-human animals which express a heterologous pub gene of the present invention, or which have had one or more genomic pub gene(s) disrupted in at least one of the tissue or cell-types of the animal. For instance, transgenic mice that are disrupted at their pub gene locus can be generated.

In another aspect, the invention features an animal model for developmental diseases, which has a pub allele which is mis-expressed. For example, a mouse can be bred which has a pub allele deleted, or in which all or part of one or more pub exons are deleted. Such a mouse model can then be used to study disorders arising from mis-expression of the pub gene.

Accordingly, the present invention concerns transgenic animals which are comprised of cells (of that animal) which contain a transgene of the present invention and which preferably (though optionally) express an exogenous pub protein in one or more cells in the animal. The pub transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of the subject protein can be essential for many forms of lineage analysis and can additionally provide a means to assess the effects of, for example, modulation of cdc25 protein levels, and thus activation of a CDK, e.g., cdc2 which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of the subject pub polypeptides. For example, excision of a target sequence which interferes with the expression of a recombinant pub gene can be designed to activate expression of that gene. This interference with expression of the protein can result from a variety of mechanisms, such as spatial separation of the pub gene from the promoter element or an internal stop codon. Moreover, the transgene can be made wherein the coding sequence of the gene is flanked recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al., (1992) *Proc. Natl. Acad. Sci. USA* 89:6232–6236; Orban et al., (1992) *Proc. Natl. Acad. Sci. USA* 89:6861–6865) or the FLP recombinase system of *Saccharomyces cerevisiae* (O'Gorman et al., (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al., (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of the pub gene can be regulated via regulation of recombinase expression.

Use of the cre/loxP recombinase system to regulate expression of a recombinant pub protein requires the construction of a transgenic animal containing transgenes encoding both the Cre recombinase and the subject protein. Animals containing both the Cre recombinase and the recombinant pub genes can be provided through the construction of "double" transgenic animals. A convenient method for providing such animals is to mate two transgenic animals each containing a transgene, e.g., the pub gene and recombinase gene.

One advantage derived from initially constructing transgenic animals containing a pub transgene in a recombinase-mediated expressible format derives from the likelihood that the subject protein may be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues. Thus, the creation of a founder population in which, for example, an antagonistic pub transgene is silent will allow the study of progeny from that founder in which disruption of cell-cycle regulation in a particular tissue or at developmental stages would result in, for example, a lethal phenotype.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080. Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, the pub transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al., (1985) *Proc. Natl. Acad. Sci. USA* 82:4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *Proc. Natl. Acad. Sci. USA* 73:1260–1264). Efficient infection of the blastomeres is obtained by enzymatic treatment to remove the zona pellucida (*Manipulating the Mouse Embryo,* Hogan eds. (Cold Spring Harbor Laboratory Press, Cold Spring Harbor, 1986). The viral vector system used to introduce the transgene is typically a replication-defective retrovirus carrying the transgene (Jahner et al., (1985) *Proc. Natl. Acad. Sci. USA* 82:6927–6931; Van der Putten et al., (1985) *Proc. Natl. Acad. Sci. USA* 82:6148–6152). Transfection is easily and efficiently obtained by culturing the blastomeres on a monolayer of virus-producing cells (Van der Putten, supra; Stewart et al., (1987) *EMBO J.* 6:383–388). Alternatively, infection can be performed at a later stage. Virus or virus-producing cells can be injected into the blastocoele (Jahner et al., (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al., (1982) supra).

A third type of target cell for transgene introduction is the embryonal stem cell (ES). ES cells are obtained from pre-implantation embryos cultured in vitro and fused with embryos (Evans et al., (1981) *Nature* 292:154–156; Bradley et al., (1984) *Nature* 309:255–258; Gossler et al., (1986) *Proc. Natl. Acad. Sci. USA* 83: 9065–9069; and Robertson et al., (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

Methods of making knock-out or disruption transgenic animals are also generally known. See, for example, *Manipulating the Mouse Embryo,* (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a pub gene can be controlled as above.

Yet another aspect of the invention pertains to methods of treating proliferative and/or differentiative disorders which arise from cells which, despite aberrant growth control, still require a pub-dependent cdc25 activation for cell growth. There are a wide variety of pathological cell proliferative conditions for which the pub gene constructs, pub mimetics and pub antagonists, of the present invention can provide therapeutic benefits, with the general strategy being the inhibition of anomalous cell proliferation. For instance, the gene constructs of the present invention can be used as a part of a gene therapy protocol, such as to reconstitute the function of an h-pub1 or h-pub2 proteins, e.g. in a cell in which the protein is misexpressed or in which signal transduction pathways upstream of a pub protein are dysfunctional, or to inhibit the function of the wild-type protein, e.g. by delivery of a dominant negative mutant.

To illustrate, cell types which exhibit pathological or abnormal growth presumably dependent at least in part on a function (or dysfunction) of a pub protein include various cancers and leukemias, psoriasis, bone diseases, fibroproliferative disorders such as involving connective tissues, atherosclerosis and other smooth muscle proliferative disorders, as well as chronic inflammation. In addition to proliferative disorders, the treatment of differentiative disorders which result from either de-differentiation of tissue due to aberrant reentry into mitosis, or unwanted differentiation due to a failure of a cdc25 phosphatase to appropriately activate certain CDK complexes.

It will also be apparent that, by transient use of gene therapy constructs of the subject pub proteins (e.g. agonist and antagonist forms) or antisense nucleic acids, in vivo reformation of tissue can be accomplished, e.g. in the development and maintenance of organs. By controlling the proliferative and differentiative potential for different cells, the subject gene constructs can be used to reform injured tissue, or to improve grafting and morphology of transplanted tissue. For instance, pub agonists and antagonists can be employed therapeutically to regulate organs after physical, chemical or pathological insult. For example, gene therapy can be utilized in liver repair subsequent to a partial hepatectomy, or to promote regeneration of lung tissue in the treatment of emphysema.

In one aspect of the invention, expression constructs of the subject pub proteins may be administered in any biologically effective carrier. e.g. any formulation or composition capable of effectively transfecting cells in vivo with a recombinant pub gene. Approaches include insertion of the subject gene in viral vectors including recombinant retroviruses, adenovirus, adeno-associated virus. and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid encoding one of the subject proteins into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding a pub polypeptide, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology,* Ausubel, F. M. et al., (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre. ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis et al., (1985) *Science* 230:1395–1398; Danos and Mulligan, (1988) *Proc. Natl. Acad. Sci. USA* 85:6460–6464; Wilson et al., (1988) *Proc. Natl. Acad. Sci. USA* 85:3014–3018; Armentano et al., (1990) *Proc. Natl. Acad. Sci. USA* 87:6141–6145; Huber et al., (1991) *Proc. Natl. Acad. Sci. USA* 88:8039–8043; Ferry et al., (1991) *Proc. Natl. Acad. Sci. USA* 88:8377–8381; Chowdhury et al., (1991) *Science* 254:1802–1805; van Beusechem et al., (1992) *Proc. Natl. Acad. Sci. USA* 89:7640–7644; Kay et al., (1992) *Human Gene Therapy* 3:641–647; Dai et al., (1992) *Proc. Natl. Acad. Sci. USA* 89:10892–10895; Hwu et al., (1993) *J. Immunol.* 150:4104–4115; U.S. Pat. Nos. 4,868,116; 4,980,286; PCT Application WO 89/07136; PCT Application WO 89/02468; PCT Application WO 89/05345; and PCT Application WO 92/07573).

In choosing retroviral vectors as a gene delivery system for the subject pub genes, it is important to note that a prerequisite for the successful infection of target cells by most retroviruses, and therefore of stable introduction of the recombinant pub gene, is that the target cells must be dividing. In general, this requirement will not be a hindrance to use of retroviral vectors to deliver agonistic pub gene constructs. In fact, such limitation on infection can be beneficial in circumstances wherein the tissue (e.g. nontransformed cells) surrounding the target cells does not undergo extensive cell division and is therefore refractory to infection with retroviral vectors.

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) *Proc. Natl. Acad. Sci. USA* 86:9079–9083; Julan et al., (1992) *J. Gen Virol* 73:3251–3255; and Goud et al., (1983) *Virology* 163:251–254); or coupling cell surface ligands to the viral env proteins (Neda et al., (1991) *J. Biol. Chem.* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue- or cell-specific transcriptional regulatory sequences which control expression of the pub gene of the retroviral vector.

Another viral gene delivery system useful in the present invention utilizes adenovirus-derived vectors. The genome of an adenovirus can be manipulated such that it encodes a gene product of interest, but is inactivate in terms of its ability to replicate in a normal lytic viral life cycle (see, for example, Berkner et al., (1988) *BioTechniques* 6:616; Rosenfeld et al., (1991) *Science* 252:431–434; and Rosenfeld et al., (1992) *Cell* 68:143–155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) *Proc. Natl. Acad. Sci. USA* 89:6482–6486), hepatocytes (Herz and Gerard, (1993) *Proc. Natl. Acad. Sci. USA* 90:2812–2816) and muscle cells (Quantin et al., (1992) *Proc. Natl. Acad. Sci. USA* 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al., (1979) *Cell* 16:683; Berkner et al., supra; and Graham et al., in *Methods in Molecular Biology*, E. J. Murray, Ed. (Humana, Clifton, N.J., 1991) vol. 7. pp. 109–127). Expression of the inserted pub gene can be under control of, for example, the E1A promoter, the major late promoter (MLP) and associated leader sequences, the E3 promoter, or exogenously added promoter sequences.

Yet another viral vector system useful for delivery of the subject pub genes is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., *Curr. Topics in Micro. and Immunol.* (1992) 158:97–129). It is also one of the few viruses that may integrate its DNA into non-dividing cells, and exhibits a high frequency of stable integration (see for example Flotte et al., (1992) *Am. J. Respir. Cell. Mol. Biol.* 7:349–356; Samulski et al., (1989) *J. Virol.* 63:3822–3828; and McLaughlin et al., (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al., (1985) *Mol. Cell. Biol.* 5:3251–3260 can be used to introduce DNA into cells. A variety of nucleic acids have been introduced into different cell types using AAV vectors (see for example Hermonat et al., (1984) *Proc. Natl. Acad. Sci. USA* 81:6466–6470; Tratschin et al., (1985) *Mol. Cell. Biol.* 4:2072–2081; Wondisford et al., (1988) *Mol. Endocrinol.* 2:32–39; Tratschin et al., (1984) *J. Virol.* 51:611–619; and Flotte et al., (1993) *J. Biol. Chem.* 268:3781–3790).

Other viral vector systems that may have application in gene therapy have been derived from herpes virus, vaccinia virus, and several RNA viruses. In particular, herpes virus vectors may provide a unique strategy for persistence of the recombinant pub gene in cells of the central nervous system and ocular tissue (Pepose et al., (1994) *Invest Ophihalmol Vis Sci* 35:2662–2666)

In addition to viral transfer methods, such as those illustrated above, non-viral methods can also be employed to cause expression of a pub protein in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject pub gene by the targeted cell. Exemplary gene delivery systems of this type include liposomal derived systems, poly-lysine conjugates, and artificial viral envelopes.

In a representative embodiment, a gene encoding a pub polypeptide can be entrapped in liposomes bearing positive charges on their surface (e.g., lipofectins) and (optionally) which are tagged with antibodies against cell surface antigens of the target tissue (Mizuno et al., (1992) *No Shinkei Geka* 20:547–551; PCT publication WO91/06309; Japanese patent application 1047381; and European patent publication EP-A-43075). For example, lipofection of neuroglioma cells can be carried out using liposomes tagged with monoclonal antibodies against glioma-associated antigen (Mizuno et al., (1992) *Neurol. Med. Chir.* 32:873–876).

In yet another illustrative embodiment, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, the subject pub gene construct can be used to transfect hepatocytic cells in vivo using a soluble polynucleotide carrier comprising an asialoglycoprotein conjugated to a polycation, e.g. poly-lysine (see U.S. Pat. No. 5,166,320). It will also be appreciated that effective delivery of the subject nucleic acid constructs via—mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al., (1993) *Science* 260–926; Wagner et al., (1992) *Proc. Natl. Acad. Sci. USA* 89:7934; and Christiano et al., (1993) *Proc. Natl. Acad. Sci. USA* 90:2122).

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the construct in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al., (1994) *Proc. Natl. Acad. Sci. USA* 91: 3054–3057).

Moreover, as set out above, the present invention also provides assays for identifying drugs which are either agonists or antagonists of the normal cellular function of pub proteins, or of the role of pub proteins in the pathogenesis of normal or abnormal cellular proliferation and/or differentiation and disorders related thereto, as mediated by, for example, binding of pub to a target protein, e.g., a mitotic activating tyrosine phosphatase, cdc25. In one embodiment, the assay evaluates the ability of a compound to modulate binding and/or ubiquitinylation of a cdc25 protein or other complexes of cell-cycle regulatory proteins by a pub protein of the present invention. While the following description is directed generally to embodiments exploiting the interaction between pub1 and cdc25, it will be understood that similar embodiments can be generated using, for example, a pub2 protein and cdc25, or either a pub1 or pub2 protein and other cell-cycle regulatory proteins.

A variety of assay formats will suffice and, in light of the present disclosure, those not expressly described herein will nevertheless be comprehended by one of ordinary skill in the art. Agents to be tested for their ability to act as pub inhibitors can be produced, for example, by bacteria, yeast or other organisms (e.g. natural products), produced chemically (e.g. small molecules, including peptidomimetics), or produced recombinantly. In a preferred embodiment, the test agent is a small organic molecule, e.g., other than a peptide, oligonucleotide, or analog thereof, having a molecular weight of less than about 2,000 daltons.

Assays which approximate the ubiquitination of target regulatory proteins in eukaryotic cells, particularly mammalian cells, can be generated in many different forms, and include assays based on cell-free systems, e.g. purified proteins or cell lysates, as well as cell-based assays which utilize intact cells. Assays as described herein can be used in conjunction with the subject E3-like complexes to generate a ubiquitin-conjugating system for detecting agents able to modulate particular pub-dependent ubiquitination of cellular or viral regulatory proteins. Such modulators can be used, for example, in the treatment of proliferative and/or differentiative disorders, to modulate apoptosis, and in the treatment of viral infections.

In many drug screening programs which test libraries of compounds and natural extracts, high throughput assays are desirable in order to maximize the number of compounds surveyed in a given period of time. Assays of the present invention which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target. Accordingly, potential modifiers, e.g., activators or inhibitors of pub-dependent ubiquitination of a target protein can be detected in a cell-free assay generated by consitution of a functional ubiquitin conjugating system in a cell lysate, such as generated by charging a ubiquitin-depleted reticulocyte lysate (Hershko et al., (1983) *J Biol Chem* 258:8206–8214) with one or more of a ubiquitin-conjugating enzyme, an E1 enzyme, an E3-like complex comprising pub1, ubiquitin, and/or a substrate for pub1-dependent ubiquitination, such as a cdc25 phosphatase. In an alternate format, the assay can be derived as a reconstituted protein mixture which, as described below, offers a number of benefits over lysate-based assays.

In an illustrative embodiment of the present assay, the ubiquitin-conjugating system comprises a reconstituted protein mixture of at least semi-purified proteins, and even more preferably of purified proteins. The reconstituted protein mixture is derived from preparations of the regulatory protein and ubiquitin under conditions which drive the conjugation of the two molecules. For instance, the mixture can include a ubiquitin-activating enzyme (E1), a ubiquitin-conjugating enzyme (E2), an E3-like complex comprising pub1, and a nucleotide triphosphate (e.g. ATP). Alternatively, the E1 enzyme, the ubiquitin, and the nucleotide triphosphate can be substituted in the system with a pre-activated ubiquitin in the form of an E1:Ub conjugate. Likewise, a pre-activated ubiquitin can instead comprise an E2:Ub conjugate.

In preferred embodiments, the purified protein mixture substantially lacks any proteolytic activity which would degrade the target protein and/or components of the ubiquitin conjugating system. For instance, the reconstituted system can be generated to have less than 10% of the proteolytic activity associated with a typical reticulocyte lysate, and preferably no more than 5%, and most preferably less than 2%. Alternatively, the mixture can be generated to include, either from the onset of ubiquitination or from some point after ubiquitin conjugation of the regulatory protein, a ubiquitin-dependent proteolytic activity, such as a purified proteosome complex, that is present in the mixture at measured amounts.

In general, the use of reconstituted protein mixtures will be preferred among cell-free embodiments of the subject assay because they allow more careful control of the reaction conditions in the ubiquitin-conjugating system. Moreover, the system can be derived to favor discovery of modifiers, e.g., activators or inhibitors of particular steps of the ubiquitination process, especially the pub1-dependent steps. For instance, as set out above, a reconstituted protein assay can be generated which does not facilitate degradation of the ubiquitinated protein, and which utilizes a precharged E2:Ub conjugate. The level of ubiquitin-conjugated protein, which is dependent on an E3-like complex can easily be measured directly in such as system, both in the presence and absence of a candidate agent, thereby enhancing the ability to detect a modifier of the pub1-dependent step. Alternatively, the Ub-conjugating system can be allowed to develop a steady state level of regulatory protein:Ub conjugates in the absence of a proteolytic activity, but then shifted to a degradative system by addition of purified Ub-dependent proteases. Such degradative systems would be amenable to identifying proteosome inhibitors.

Moreover, in the subject method, ubiquitin conjugating systems derived from purified proteins hold a number of significant advantages over cell lysate or wheat germ extract based assays (collectively referred to hereinafter as "lysates"), especially "whole" lysates. Unlike the reconstituted protein system, the synthesis and destruction of the target protein cannot be readily controlled for in lysate-based assays. Without knowledge of particular kinetic parameters for Ub-independant and Ub-dependent degradation of the target protein in the lysate, discerning between the two pathways can be extremely difficult. Measuring these parameters, if at all possible, is further made tedious by the fact that cell lysates tend to be inconsistent from batch to batch, with potentially significant variation between preparations. Evaluation of a potential inhibitor using a lysate system is also complicated in those circumstances where the lysate is charged with mRNA encoding the target protein, as such lysates may continue to synthesize the protein during the assay, and will do so at unpredictable rates.

Accordingly, knowledge of the concentration of each component of the ubiquitin conjugation pathway can be required for each lysate batch, along with the degradative kinetic data, in order to determine the necessary time course and calculate the sensitivity of experiments performed from one lysate preparation to the next.

Furthermore, the lysate system can be unsatisfactory where the target protein itself has a relatively short half-life, especially if due to degradative processes other than the ubiquitin-mediated pathway to which an inhibitor is sought. However, as described, this effect can be mitigated by the use of protease inhibitors such as PMSF or TPCK to inhibit proteolysis of the target protein, though broad-spectrum inhibitors will knock out both ubiquitin-dependent and independent proteolysis.

Moreover, many of the disadvantages of whole cell lysates described above can be overcome by the use of semi-purified cell extracts and/or lysates that have been charged with one or more components of a ubiquitin-conjugation pathway. For example, by selective removal of cell lysate components which interfere with ubiquitination assays, an assay may be feasible in a cell extract even without further purification. Such an approach makes possible rapid and inexpensive development of assay systems suitable for use with ubiquitination assays.

Thus, in another aspect of the subject invention, the ubiquitin-conjugating system comprises a semi-purified cell extract. For instance, as described in the examples below, semi-purified cell extracts can be produced by treatment of cell lysates by a variety of techniques. For example, chromatographic methods and the like can be used to partially purify at least one component of the cell lysate. Likewise, semi-purified cell lysates may be prepared by treatment of a cell lysate to selectively remove a component of the lysate, for example, by immunoprecipation. Many other methods for the preparation of semi-purified cell extracts by the selective removal or enrichment of components of a cell lysate will be evident to the skilled artisan.

In yet another embodiment of the subject assay, a cell lysate can be charged with certain of the components of a pub1-dependent ubiquitination system. For example, in addition to inhibitors or potentiators of ubiquitination, a semi-purified cell extract can be charged with the relevant UBC, pub1, cdc25 phosphatase and the like. Likewise, lysates can be generated from cells recombinantly manipulated to produce, for example, a labeled component to the assay, such as a myc-labeled ubiquitin or a GST-cdc25 fusion protein.

Ubiquitination of the target regulatory protein via an in vitro ubiquitin-conjugating system, in the presence and absence of a candidate inhibitor, can be accomplished in any vessel suitable for containing the reactants. Examples include microtitre plates, test tubes, and micro-centrifuge tubes. In certain embodiments of the present assay, the in vitro assay system is generated to lack the ability to degrade the ubiquitinated target protein. In such an embodiments, a wide range of detection means can be practiced to score for the presence of the ubiquitinated protein.

In one embodiment of the present assay, the products of a non-degradative ubiquitin-conjugating system are separated by gel electrophoresis, and the level of ubiquitinated target protein assessed, using standard electrophoresis protocols, e.g., by detecting an increase in molecular weight of the target protein that corresponds to the addition of one or more ubiquitin chains. For example, one or both of the target protein and ubiquitin can be labeled with a radioisotope such as $^{35}S$, $^{14}C$, or $^{3}H$, and the isotopically labeled protein bands quantified by autoradiographic techniques. Standardization of the assay samples can be accomplished, for instance, by adding known quantities of labeled proteins which are not themselves subject to ubiquitination or degradation under the conditions which the assay is performed. Similarly, other means of detecting electrophoretically separated proteins can be employed to quantify the level of ubiquitination of the regulatory protein, including immunoblot analysis using antibodies specific for either the regulatory protein or ubiquitin, or derivatives thereof. As described below, the antibody can be replaced with another molecule able to bind one of either the regulatory protein or ubiquitin. By way of illustration, one embodiment of the present assay comprises the use of biotinylated ubiquitin in the conjugating system. The biotin label is detected in a gel during a subsequent detection step by contacting the electrophoretic products (or a blot thereof) with a streptavidin-conjugated label, such as a streptavidin linked fluorochrome or enzyme, which can be readily detected by conventional techniques. Moreover, where a reconstituted protein mixture is used (rather than a lysate) as the conjugating system, it may be possible to simply detect the regulatory protein and ubiquitin conjugates in the gel by standard staining protocols, including coomassie blue and silver staining.

In another embodiment, an immunoassay or similar binding assay, is used to detect and quantify the level of ubiquitinated regulatory protein produced in the ubiquitin-conjugating system. Many different immunoassay techniques are amenable for such use and can be employed to detect and quantitate the regulatory protein:Ub conjugates. For example, the wells of a microtitre plate (or other suitable solid phase) can be coated with an antibody which specifically binds one of either the regulatory protein or ubiquitin. After incubation of the ubiquitin-conjugated system with and without the candidate agent, the products are contacted with the matrix bound antibody, unbound material removed by washing, and ubiquitin conjugates of the regulatory protein specifically detected. To illustrate, if an antibody which binds the regulatory protein is used to sequester the protein on the matrix, then a detectable anti-ubiquitin antibody can be used to score for the presence of ubiquitinated regulatory protein on the matrix.

However, it will be clear to those skilled in the art that the use of antibodies in these binding assays is merely illustrative of binding molecules in general, and that the antibodies are readily substituted in the assay with any suitable molecule that can specifically detect one of either the regulatory protein or the ubiquitin. As described below, a biotin-derivative of ubiquitin can be used, and streptavidin (or avidin) employed to bind the biotinylated ubiquitin. In an illustrative embodiment, wells of a microtitre plate are coated with streptavidin and contacted with the developed ubiquitin-conjugating system under conditions wherein the biotinylated ubiquitin binds to and is sequestered in the wells. Unbound material is washed from the wells, and the level of regulatory protein (bound to the matrix via a conjugated ubiquitin moiety) is detected in each well. Alternatively, the microtitre plate wells can be coated with an antibody (or other binding molecule) which binds and sequesters the regulatory protein on the solid support, and detection of ubiquitinated conjugates of the matrix-bound regulatory protein are subsequently carried out using a detectable streptavidin derivative, such as an alkaline phosphatase/streptavidin complex.

In similar fashion, epitope-tagged ubiquitin, such as myc-ub (see Ellison et al. (1991) *J. Biol. Chem.* 266:21150–21157; ubiquitin which includes a 10-residue sequence encoding a protein of c-myc) can be used in conjunction with antibodies to the epitope tag. A major advantage of using such an epitope-tagged ubiquitin approach for detecting Ub:protein conjugates is the ability of an N-terminal tag sequences to inhibit ubiquitin-mediated proteolysis of the conjugated regulatory protein.

Other ubiquitin derivatives include detectable labels which do not interfere greatly with the conjugation of ubiquitin to the regulatory protein. Such detectable labels can include fluorescently-labeled (e.g. FITC) or enzymatically-labeled ubiquitin fusion proteins. These derivatives can be produced by chemical cross-linking, or, where the label is a protein, by generation of a fusion protein. Several labeled ubiquitin derivatives are commercially available.

Likewise, other binding molecules can be employed in place of the antibodies that bind the regulatory protein. For example, the regulatory protein can be generated as a glutathione-S-transferase (GST) fusion protein. As a practical matter, such GST fusion protein can enable easy purification of the regulatory protein in the preparation of components of the ubiquitin-conjugating system (see, for example, *Current Protocols in Molecular Biology*, eds. Ausubel et al. (NY: John Wiley & Sons, 1991); Smith et al. (1988) *Gene* 67:31; and Kaelin et al. (1992) *Cell* 70:351) Moreover, glutathione derivatized matrices (e.g. glutathione-sepharose or glutathione-coated microtitre plates) can be used to sequester free and ubiquitinated forms of the regulatory protein from the ubiguitin-conjugating system, and the level of ubiquitin immobilized can be measured as described. Likewise, where the matrix is generated to bind ubiquitin, the level of sequestered GST-regulatory protein can be detected using agents which bind to the GST moiety (such as anti-GST antibodies), or, alternatively, using agents which are enzymatically acted upon by GST to produce detectable products (e.g. 1-chloro-2,4-dinitrobenzene; Habig et al. (1974) *J Biol Chem* 249:7130). Similarly, other fusion proteins involving the regulatory protein and an enzymatic activity are contemplated by the present method. For example, fusion proteins containing β-galactosidase or luciferase, to name but a few, can be employed as labels to determine the amount of regulatory protein sequestered on a matrix by virtue of a conjugated ubiquitin chain.

Moreover, such enzymatic fusion proteins can be used to detect and quantitate ubiquitinated regulatory protein in a heterogeneous assay, e.g., one which does not require separation of the components of the conjugating system. For example, ubiquitin conjugating systems can be generated to have a ubiquitin-dependent protease which degrades the regulatory protein. The enzymatic activity of undegraded fusion protein provides a detectable signal, in the presence of substrate, for effectively measuring the level of the regulatory protein ubiquitination. Similarly, in a non-degradative conjugating system, ubiquitination of the regulatory protein portion of the fusion protein can allosterically influence the enzymatic activity associated with the fusion the protein and thereby provides a means for monitoring the level of ubiquitin conjugation.

In binding assay-type detection steps such as set out above, the choice of which of either the regulatory protein or ubiquitin should be specifically sequestered on the matrix will depend on a number of factors, including the relative abundance of both components in the conjugating system. For instance, where the reaction conditions of the ubiquitin conjugating system provide ubiquitin at a concentration far in excess of the level of the regulatory protein, (e.g., one order of magnitude or greater) sequestering the ubiquitin and detecting the amount of regulatory protein bound with the ubiquitin can provide less dynamic range to the detection step of the present method than the converse embodiment of sequestering the regulatory protein and detecting ubiquitin conjugates from the total regulatory protein bound to the matrix. That is, where ubiquitin is provided in great excess relative to the regulatory protein, the percentage of ubiquitin conjugated regulatory protein in the total ubiquitin bound to the matrix can be small enough that any diminishment in ubiquitination caused by a modifier can be made difficult to detect by the fact that, for example, the statistical error of the system (e.g. the noise) can be a significant portion of the measured change in concentration of bound regulatory protein. Furthermore, it is clear that manipulating the reaction conditions and reactant concentrations in the ubiquitin-conjugating system can be carried out to provide, at the detection step, greater sensitivity by ensuring that a strong ubiquitinated protein signal exists in the absence of any modifier.

In still further embodiments of the present invention, the ubiquitin-conjugating system is generated in whole cells, taking advantage of cell culture techniques to support the subject assay. For example, as described below, the ubiquitin-conjugating system (including the target protein and detection means) can be constituted in a eukaryotic cell culture system, including mammalian and yeast cells. Advantages to generating the subject assay in an intact cell include the ability to detect inhibitors which are functional in an environment more closely approximating that which therapeutic use of the inhibitor would require, including the ability of the agent to gain, entry into the cell. Furthermore, certain of the in vivo embodiments of the assay, such as examples given below, are amenable to high through-put analysis of candidate agents.

The components of the ubiquitin-conjugating system, including the regulatory protein, can be endogenous to the cell selected to support the assay. Alternatively, some or all of the components can be derived from exogenous sources. For instance, a recombinantly produced E2 enzyme, such as UBC3, UBC4, UBC5 and/or UBC9, or recombinantly produced components of an E3-like complex comprising pub1, can be expressed in the cell by recombinant techniques (such as through the use of an expression vector), as well as by microinjecting the proteins themselves or mRNA encoding the protein.

In any case, the cell is ultimately manipulated after incubation with a candidate inhibitor in order to facilitate detection of ubiquitination or ubiquitin-mediated degradation of the regulatory protein. As described above for assays performed in reconstituted protein mixtures or lysates, the effectiveness of a candidate inhibitor can be assessed by measuring direct characteristics of the regulatory protein, such as shifts in molecular weight by electrophoretic means or detection in a binding assay. For these embodiments, the cell will typically be lysed at the end of incubation with the candidate agent, and the lysate manipulated in a detection step in much the same manner as might be the reconstituted protein mixture or lysate.

Indirect measurement of ubiquitination of the target protein can also be accomplished by detecting a biological activity associated with the regulatory protein that is either attenuated by ubiquitin-conjugation or destroyed along with the regulatory protein by ubiquitin-dependent proteolytic processes. As set out above, the use of fusion proteins comprising the regulatory protein and an enzymatic activity are representative embodiments of the subject assay in which the detection means relies on indirect measurement of ubiquitination of the regulatory protein by quantitating an associated enzymatic activity.

Where the regulatory protein has a relatively short half-life due to ubiquitin-dependent or independent degradation in the cell, preferred embodiments of the assay either do not require cell lysis, or, alternatively, generate a longer lived detection signal that is independent of the regulatory protein's fate after lysis of the cell. With respect to the latter embodiment, the detection means can comprise, for example, a reporter gene construct which includes a positive transcriptional regulatory element that binds and is responsive to the regulatory protein. For instance, where the regulatory protein does not itself posses DNA-binding ability, it can be arranged as part of an interaction trap assay designed for detecting modifiers, e.g., activators or inhibitors, of the pub1-dependent destruction of the protein (see, for example, U.S. Pat. No. 5,283,317; PCT publication WO94/10300; Zervos et al., (1993) *Cell* 72:223–232; Madura et al., (1993) *J Biol Chem* 268:12046–12054; Bartel et al., (1993) *Biotechniques* 14:920–924; and Iwabuchi et al., (1993) *Oncogene* 8:1693–1696). In an illustrative embodiment, *Saccharomyces cerevisiae* YPB2 cells are transformed simultaneously with a plasmid encoding a GAL4db-pub1 (where pub is a catalytically inactive) fusion and with a plasmid encoding the GAL4ad domain fused to human cdc25 phosphatase. Moreover, the strain is transformed such that the GAL4-responsive promoter drives expression of a phenotypic marker. For example, the ability to grow in the absence of histidine depends on the expression of the HIS3 gene if it is under control of a GAL4-responsive promoter and, therefore, indicates that a functional GAL4 activator has been reconstituted through the interaction of the h-pub1 and the human cdc25 fusion proteins.

Thus, for example, agents able to inhibit the ubiquitination of the cdc25 fusion protein will result in yeast cells able to growth in the absence of histidine, as the GAL4db-pub1 and GAL4ad-cdc25 fusion proteins will be able to interact and cause expression of the HIS3 gene. Alternatively, the agents which do not effect the ubiquitination of the cdc25 fusion protein will result in cells unable to grow in the absence of histidine as the GAL4ad-cdc25 fusion protein will be degraded or otherwise prevented from interacting with the GAL4db-pub1 protein.

The present invention also makes available *S. pombe* strains which contain a null pub mutation. As described herein, these strains can be complemented using human genes, and thus "humanized" yeast strains can be created for in vivo drug screen, e.g., which comprise a human pub homolog and (optionally) a human cdc25 phosphatase. The strain can be further manipulated to be "humanized" with respect to other biochemical steps in the pub1-mediated ubiquitination of the cdc25 fusion protein. For example, conditional inactivation of the relevant yeast UBC enzyme with concomitant expression of the human UBC homolog, or alternatively, replacement of other yeast genes involved in ubiquitination with their human homologs, provides a humanized system whereby the cdc25 protein can be ubiquitinated by a pub1-dependent mechanism which approximates the pub1-dependent ubiquitination that occurs in vertebrate cells.

Furthermore, drug screening assays can be generated which do not measure ubiquitination per se, but rather detect inhibitory agents on the basis of their ability to interfere with binding of one of the proteins involved in the pub1-dependent ubiquitin conjugation pathway. In an exemplary binding assay, the compound of interest is contacted with a mixture generated from an isolated and purified E2 protein and an E3-like complex comprising the pub protein. Alternatively, pub and cdc25 are combined in the presence and absence of test agents so as to provide a competitive binding assay which detects agents able to compete with, or potentiate, the cdc25 binding to pub1. Detection and quantification of complexes between the pub and cdc25 provides a means for determining the compound's efficacy at inhibiting (or potentiating) complex formation between the pub and other components of the pub1-dependent ubiquitin pathway. The efficacy of the compound can be assessed by generating dose response curves from data obtained using various concentrations of the test compound. Moreover, a control assay can also be performed to provide a baseline for comparison. In the control assay, isolated and purified cdc25 is added to a composition containing the pub protein, and the formation of complexes is quantitated in the absence of the test compound.

Complex formation between cdc25 protein or other regulatory protein and pub may be detected by a variety of techniques, many of which are effectively described above. For instance, modulation in the formation of complexes can be quantitated using, for example, detectably labeled proteins (e.g. radiolabelled, fluorescently labelled, or enzymatically labelled), by immunoassay, or by chromatographic detection.

Typically, it will be desirable to immobilize either the regulatory protein, e.g., cdc25 or a component of the E3-like complex, such as the pub protein, to facilitate separation of complexes from uncomplexed forms of one of the proteins, as well as to accommodate automation of the assay. In an illustrative embodiment, a fusion protein can be provided which adds a domain that permits the protein to be bound to an insoluble matrix. For example, GST/cdc25 fusion proteins can be adsorbed onto glutathione sepharose beads (Sigma Chemical, St. Louis, Mo.) or glutathione derivatized microtitre plates, which are then combined with the pub protein, e.g. containing $^{35}$S-labeled proteins, and the test compound and incubated under conditions conducive to complex formation. Following incubation, the beads are washed to remove any unbound pub1, and the matrix bead-bound radiolabel determined directly (e.g. beads placed in scintilant), or in the supernatant after the complexes are dissociated, e.g. when microtitre plaste is used. Alternatively, after washing away unbound protein, the complexes can be dissociated from the matrix, separated by SDS-PAGE gel, and the level of, for example, pub protein found in the matrix-bound fraction quantitated from the gel using standard electrophoretic techniques.

EXEMPLIFICATION

The invention now being generally described, it will be more readily understood by reference to the following examples which are included merely for purposes of illustration of certain aspects and embodiments of the present invention, and are not intended to limit the invention.

I. Cloning of *Schizosaccharomyces pombe* Pub1

In a screen that was originally designed to identify novel *S. pombe* tyrosine kinases, a *S. pombe* cDNA expression library cloned in λZAP2 was screened with an antiphosphotyrosine monoclonal antibody (Lindberg et al., (1988) *Oncogene* 3:629–633; Lindberg and Pasquale, (1991) *Meth. Enzymol.* 200:557–564; Druker et al., (1989) *New Eng. J. Med.* 321:1383–1391). Two hundred and fifty thousand phage plaques were examined and two positives obtained, each containing a different cDNA. Pub1 was one of the two genes identified by this screen. The original isolate encoded a fusion protein between the first 24 amino acids of beta-galactosidase and the last 739 amino acids of pub1. Sequence analysis of this open reading frame revealed a putative ATP binding site (GxGxxG) with a valine residue located 6 and a lysine residue located 25 amino acids downstream of this site (see SEQ ID No. 4). Aside from this potential match to subdomains 1 and 2, pub1 contained no other significant homology to the 12 subdomain consensus sequence of the kinase catalytic domain (Hanks et. al., (1988) *Science* 241:42–52; Hanks and Quinn, (1991) *Meth. Enzymol.* 200:38–62). In addition, we were unable to detect any tyrosine kinase activity associated with pub 1 in vitro. Peptide and polyglutyr tyrosine kinase assays of lysates prepared from cells expressing the original, βgal-pub I fusion protein were negative (Braun et al., (1984) *J. Biol. Chem.* 259:2051–2054; Casnelli, (1991) *Meth. Enzymol.* 200: Racker, (1991) *Meth. Enzymol.* 200:107–111, Wong and Goldberg, (1983) *J. Biol. Chem.* 258:1022–1.025). Similarily, peptide, polyglutyr and autophosphorylation assays of a purified GST-pub1 fusion protein which fused the originally isolated pub1 fragment to the C terminus of glutathione-S-transferase were negative. Finally, these same assays performed with a purified full length pub1 fused to the C terminus of maltose binding protein were also negative. We therefore suspect that the appearance of tyrosine phosphorylated proteins upon expression of pub1 in *E. coli* was indirect.

To obtain a full length pub1 cDNA, the *S. pombe* cDNA library was reprobed with the originally isolated pub1 fragment. A 2,847 bp cDNA was isolated. A single 2.9 kb pub1 message was detected by Northern blot Qf logarithmically growing wild type cells (972) indicating that we had isolated a cDNA at or close to full length.

To physically map the pub1 gene we probed a collection of contiguous cosmid clones spanning the *S. pombe* genome with pub1 cDNA (Mizukami et al., (1993) *Cell* 73:121–132). Three overlapping cosmids, 323, 437 and 1187 hybridized to our probe indicating that pub1 is on the right arm of chromosome 1 near the centromere. Two nearby adjacent Not1 sites and cut7 are the closest distal markers to the gene.

II. Pub1 is Shares Some Homology to the Putative E6-AP Catalytic Domain

Sequence analysis of the 2.8 kb pub1 cDNA revealed a 766 amino acid open reading frame. In vitro transcription and translation of this cDNA resulted in the formation of a 85 kD translation product, consistent with the size of the predicted ORF. A blast search of genbank revealed three proteins of unknown function which share homology with pub1: the *S. cerevisiae* protein RSP5 (71% identical), the human protein D42055 (47% identical) and the mouse protein NEDD4 (40% identical) (Kumar et. al., (1992) *Biochem. Biophys. Res. Comm.* 185:1155–1161; Huibregtse et al., (1995) 92:2563–2567). The human protein ubiquitin ligase E6-AP is 32% identical to pub1 and the most similar protein of known function in the database. The protein ubiquitin ligase activity of E6-AP requires the formation of an thioester intermediate between cys 833 of E6-AP and the C terminus of ubiquitin (Scheffner et al. (1995) *Nature* 373:81–83). The site of E6AP thiol ubiquitination and the region surrounding this residue are conserved in pub1. The sequence similarity between these two proteins is concentrated in the C terminal third of each. Pub1 lacks the sequence required for E6 binding and has only slight similarity to the region of E6AP shown to be required for pS3 binding by deletioll analysis (Huibregtse et al. (1993b) *Mol. Cell. Biol.* 13:4918–4927). The nine proteins identified by a blast search of genbank to be most similar to pub1 have the same conserved C terminal domain in common with E6AP. These proteins come from several eucaryotic sources and may define an E6AP like family of protein ubiquitin ligases (Scheffner et. al., (1995) supra).

There is a class of proteins which alternate between freely soluble and membrane bound forms in a $Ca^{+2}$ dependent fashion. Such proteins translocate to specific phospholipid membranes in the presence of micromolar amounts of calcium. A peptide containing the sequence necessary and sufficient for the $Ca^{+2}$ dependent phospholipid membrane binding was identified in a cytosolic phospholipase A2 (Clark et al., (1991) *Cell* 65:1043–1051). This peptide contained a sequence motif (CaLB domain) conserved in several proteins which translocate to the plasma membrane in a $Ca^{+2}$ dependent fashion including PKC and GAP (Clark et al., (1991) supra). Pub1 contains a motif which is highly homologous to the CaLB consensus sequence. A full length MBP-pub1 fusion protein damatically increases its affinity for hydrophobic column matricies in a $Ca^{+2}$ dependent fashion suggesting that this motif is functional in vitro.

III. Genetic Interactions with Wee1 and cdc25

A pub 1 null allele was constructed by replacing a 948bp Sal I-Nsi I fragment of the pub 1 ORF with the ura4 gene. This construct effectively disrupts about two thirds of the pub I ORF including the putative protein ubiquitin ligase domain. A linear fragment containing the disrupted pub1 gene was introduced into the diploid strain SP826 (Table 1). Stable Ura+ transformants were recovered by screening for failure to grow in the presence of 5-fluoroorotic acid (FOA) and Southern blot analysis confirmed that most of those carried one copy of the publ disruption allele (pub1::ura4) and one copy of the wild type gene. Upon sporulation at 30° C. the diploid heterozygous for the publ disruption produced four viable spores indicating that publ is not essential for vegetative growth. Southern blot analysis of the Ura+ haploid cells confirmed that they carried only the disrupted publ gene.

TABLE 1

List of *S. pombe* Strains

| Strain | Genotype |
|---|---|
| 972 | $h^{-S}$ |
| SP 6 | $h^{-S}$ leu 1-32 |
| SP 546 | $h^{+N}$ wee1-50 |
| SP 628 | $h^{+N}$ cdc25-22 leu1-32 |
| SP826 | $h^{+N}/h^{+N}$ ade6-210/ade6-216 leu1-32/leu1-32 ura4-D18/ura4-D18 |
| SP 974 | $h^{+N}$ cdc2-3w cdc25-22 ura4-D18 |
| SP 1062 | $h^{-S}$ cdc25-22ΔART8-25.4 leu1-32 ura4- |
| SP 1207 | $h^{-S}$ pub1::ura4 ura4-D18 |
| SP I 208 | $h^{+N}$ pub1::ura4 leu1-32 ura4-D 18 |
| SP 1209 | $h^{-S}$ pub1::ura4 wee1-50 ura4-D18 |
| SP 1210 | $h^{-S}$ pub1::ura4 cdc25-22 ura4-D18 |
| SP 1211 | $h^{-S}$ pub1::ura4 wee1-50 cdc25-22 ura4-D18 |
| SP 1212 | $h^{-S}$ mts2 cdc25(HA)$_3$ leu1-32 |
| SP 1213 | $h^{-S}$ mts2 pub1::ura4 cdc25(HA)$_3$ leu1-32 ura4-D18 |

Strain SP 1062 was constructed by stably transforming SP 586 h-S cdc25-22, leu1-32, ura4- with pART8-25.4 which carries cdc25 under the strong constituitive ADH promoter control.
StrainCFX 109-2Rh+Ncdc25(HA)3 leu1-32, ura4-D18 used to construct strains SP 1212 and SP 1213.
The cdc25 allele cdc25(HA)$_3$ has a triple tandem hemagglutinin epitope inserted in frame at the Cla1 site of cdc25. The resulting construct was integrated into the *S. pombe* genome at the cdc25-22 site. This allele rescues cdc25-22 at restrictive temperature.
The mts2 allele used to construct strains SP 1212 and SP 1213.

The dephosphorylation of cdc2 on tyrosine 15 is a rate limiting step for the transition of *S. pombe* cells from G2 into mitosis (Gould and Nurse, (1989) *Nature* 342:39–45). The tyrosine phosphorylation state of cdc2 is determined by a balance between the activities of the mitotic inhibitory tyrosine kinases wee1 and mik1 and the mitotic activating tyrosine phosphatases cdc25 and pyp3 (Russell and Nurse, (1986) *Cell* 45:145–153; Russell and Nurse, (1987) *Cell* 49:559–567; Lundgren et al., (1991) *Cell* 64:1111–1122; Dunphy and Kumagai, (1991) *Cell* 67:189–196; Gautier et al., (1991) *Cell* 67:197–211; Millar et al., (1992) *EMBO J.* 11:4933–4941). Cdc25 and wee1 are the predominant activities (Lundgren et. al., (1991) supra; Millar et al., (1992) supra). To test for a genetic interaction between pub1 and either cdc25 or wee1, we constructed the strains outlined in Table 2. This table also contains a summary of the phenotypes observed for each strain. Wee1-50 is a temperature sensitive recessive loss of function allele of the nonessential gene wee1 (Nurse, (1975) *Nature* 256:547–551; Nurse and Thuriaux, (1980) *Genetics* 96:627–637). At restrictive temperature (37° C.) cells bearing a wee1-50 allele undergo mitosis at a cell size significantly smaller than wild type. Loss of wee1 function in a pub1 disruption background is lethal. The apparent fragmentation of chromosomes, formation of anucleate cells and occasional septation through the nucleus observed in the double mutant (SP 1209) at restrictive temperature are thought to be the result of premature mitosis (Russell and Nurse, (1987) supra; Lundgren et al., (1991) supra). A similar mitotic lethality with wee1-50 has been observed in several cases: in the absence of mik1; in the presence of the dominant activated cdc2 allele cdc2-3w; in the presence of G2/M checkpoint mutants and in cells overproducing cdc25 (Lundgren et al., (1991) supra; Russell and Nurse, (1986) supra; Russell and Nurse, (1987) supra; Al-Khodairy and Carr, (1992) *EMBO J.* 11:1343–1350; Rowley et al., (1992) *EMBO J.* 1335–1342; Enoch et al., (1992) *Gene & Dev.* 6:2035–2046; Walworth et al., (1993) *Nature* 363:369–371).

TABLE 2

Genetic Interactions

A.
| Relevant Genotype | 20° C. | 25° C. | 30° C. | 37° C. |
| --- | --- | --- | --- | --- |
| pub1::ura4 | + | + | + | + |
| wee1-50 | + | + | + | + |
| pub1::ura4, wee1-50 | + | + | + | −(l.m.) |
| cdc25-22 | + | + | + | −(cdc⁻) |
| pub1::ura4, cdc25-22 | − | + | + | −(cdc⁻) |
| pub1::ura4, wee1-50, cdc25-22 | − | + | + | + |

B.
| Relevant Genotype | +thiamin | −thiamin |
| --- | --- | --- |
| pub1 + + pREP41 | + | + |
| pub1 + + pREP41wee1 | + | −(cdc⁻) |
| pub1 + + pREP41mik1 | + | −(cdc⁻) |
| pub1::ura4 + pREP41 | + | + |
| pub1::ura4 + pREP41wee1 | + | + |
| pub1::ura4 + pREP41mik1 | + | + |
| pub1::ura4 + pREP1 | + | + |
| pub1::ura4 + pREP1wee1 | + | −(cdc⁻) |
| pub1::ura4 + pREP1mik1 | + | −(cdc⁻) | l.m. = lethal mitosis
cdc⁻ = cell cycle arrest with single nuclei and elongated cells. These cells arrest at the G2/M boundary with a 2N DNA content.

To determine if the pub1::ura4 wee1-50 synthetic lethality requires cdc25 function we constructed a pub1::ura4 wee1-50 cdc25-22 triple mutant (SP 1211). Cdc25-22 is a temperature sensitive, recessive, loss of function allele of cdc25. Cdc25 is an essential gene whose loss results in cell-cycle arrest at the G2/M boundary with tyrosine phosphorylated cdc2 and characteristically elongated cells (Russell and Nurse, (1986) supra; Gould and Nurse, (1989) supra; Lundgren et al., (1991) supra). Loss of cdc25 function however can be rescued by the simultaneous loss of the antagonistic wee1 function (Fantes, (1979) *Nature* 279:428–430). Thus, a wee1-50 cdc25–22 double mutant is viable at the restrictive temperature of both single mutants. The pub1::ura4 wee1-50 cdc25-22 triple mutant is also viable at restrictive temperature indicating that the mitotic lethality of the pub1::ura4 wee1-50 double mutant requires cdc25 function. This is not true of the mik1::ura4 wee1-50 cdc25-22 triple mutant which undergoes lethal premature mitosis at restrictive temperature (Lundgren et al., (1991) supra). The viability of the pub1::ura4 wee1-50 cdc25-22 triple mutant at restrictive temperature suggests that the lethal premature entry into mitosis by pub1::ura4 wee1-50 is not the result of pub1::ura4 dependent inhibition of mik1. The difference between the phenotypes of the two triple mutants can be understood as a simple case of epistasis. If a cell prematurely enters mitosis because it has lost both wee1 and mik1 function and thus cannot tyrosine phosphorylate cdc2, a dramatic reduction in the ability to tyrosine dephosphorylate cdc2 will not rescue the cell. If, on the other hand, the tyrosine phosphatase activity of both cdc25 and pyp3 are simply overwhelming the ability of mik1 to phosphorylate cdc2, loss of cdc25 function could potentially rescue the cell. The lethal mitotic phenotype of the pub1::ura4 wee1-50 double mutant and viability of the pub1::ura4 wee1-50 cdc25-22 triple mutant suggests that the loss of pub1 function activates either cdc25 or pyp3 or both.

IV. Pub1 Disruption Increases Tolerance of Wee1 and Mik1 Overproduction

If disruption of pub 1 activates cdc25 or pyp3, the disruption should act antagonistically to both wee1 and mik1. To test this, we overproduced wee1 and mik1 in both pub1+ (SP6) and pub1::ura4 (SP 1208) cells. pREP41 is a *S. pombe* expression vector with a inducible nmt promoter (Maudrell, (1993) *Gene* 123:127–130). Expression from the nmt promoter is induced by starvation for thiamin. In the pREP41 plasmid the nmt promoter has been mutated to reduce the level of induction about 10 fold below that of the wild type nmt promoter. Wee1 and mik1 expressed from pREP41 plasmids will arrest the cell-cycle of wild type *S. pombe* at the G2/M boundary. pREP41 plasmids containing either wee1, mik1 or no insert were introduced into either a pub1+ (SP6) or a pub1− (SP 1208) strains and grown in the presence of thiamin. Transformants were then tested for their ability to form colonies in the absence of thiamin. A summary of the results can be seen in Table 2. Pub1+ cells expressing either wee1 or mik1 from a pREP41 vector failed to form colonies in the absence of thiamin. The cells arrest at the G2/M boundary with a classic cdc-elongated cell phenotype. In contrast, pub1− cells expressing wee1 or mik1 from a pREP41 vector could readily form colonies in the absence of thiamin. Loss of pub1 does no affect the level of eiither wee1 or mik1 expression in these strains as determined by Western blot analysis. Nor, does loss of pub render *S. pombe* fully insensitive to overproduction of either wee1 or mik1. Pub1− cells expressing either wee1 or mik1 from the pREP41 vector, divided at a cell size noticeably longer than vector controls. Furthermore, when either wee1 or mik1 is expressed at higher levels using a wild type nmt promoter in a pREPI vector, pub1− cells cannot form colonies in the absence of thiamin (Maudrell, (1993) supra). These cells have the same terminal phenotype exhibited by pub1+ cells at lower levels of wee1 and mik1 expression. Thus, loss of pub1 acts antagonistically to both wee1 and mik1 increasing the amount of these kinases required to arrest the cell-cycle.

V. The pub1::ura4,cdc25-22 double mutant is cold sensitive

To further investigate the possibility of a genetic interaction between pub1 and cdc25, we constructed a pub1::ura4 cdc25-22 double mutant (SP 1210). At the restrictive temperature of cdc25-22, this double mutant arrests at the G2/M boundary with the same terminal phenotype of a cdc25-22 single mutant (SP628)—elongated cells with a 2N DNA content. Overexpression of pyp3 will rescue a cdc25-22 mutant at restrictive temperature (Millar et al., (1992) *EMBO J*. 11:4944–4941). If the pub1 disruption is activating pyp3, it is insufficient for such a rescue. The cdc25-22 mutation can also be rescued by loss of wee1 function. Thus, if pub1::ura4 is inhibiting wee1, it is also insufficient to rescue the loss of cdc25 function.

While either the pub1::ura4 or the cdc25-22 single mutants grow well at reduced temperature. the pub1::ura4 cdc25-22 double mutant is a cold sensitive synthetic lethal, unable to grow at 20° C. Interestingly, the terminal phenotype of this double mutant is not the cdc-elongated cell phenotype caused by loss of cdc25 function nor the wee phenotype resulting from a significant increase in the level of active cdc25.

VI. Pub1 Disruption Elevates Cdc25

To determine if cdc25 is overexpressed in a pub1 disruption background we examined the levels of cdc25 mRNA and protein in both wild type (972) and pub1::ura (SP 1207) strains. Asynchronous cultures of both strains were grown to mid log at 30° C. in YEA. Aliquotes were removed from each culture for both Northern and Western blot analysis. Loss of pub does not effect the steady state level of cdc25 message. To determine the level of cdc25 protein in these strains, lysates were prepared from mid log cultures grown at 30° C. in YEA and subjected to Western blot analysis. Lysates prepared in an identical fashion from two additional cultures, a cdc25 disruption (SP974) and a cdc25 overproducer (SP1062) were used as controls for antibody specificity. (Cdc2-3w rescues loss of cdc25 function in *S. pombe* (Russell and Nurse, (1987) supra).) The level of cdc25 in asynchronously growing pub1::ura4 cells is about 4 fold higher than wild type. The disruption of pub1 post transcriptionally increases the level of cdc25 protein in vivo. Thus, pub1 could either be inhibiting cdc25 translation or enhancing its degradation.

VII. Cdc25 is Ubiquitinated in a Pub1 Dependent Fashion

The sequence similarity between pub1 and the protein ubiqitin ligase E6-AP raised the possibility that cdc25 may be ubiquitinated in *S. pombe* and that pub1 may be involved. Mts2 is a temperature sensitive mutant in the S4 subunit of the 26S proteosome in *S. pombe* (Gordon et al., (1993) *Nature* 366:355–357). The 26S proteosome is responsible for the degradation of protein ubiquitin conjugates and these conjugates accumulate in a mts2 mutant at restrictive temperature (Finley and Chau, (1991) *Annu. Rev. Cell Biol.* 7:25–69; Gordon et al., (1993) supra). To determine if mts2 mutants accumulate ubiquitinated cdc25 in a pub1 dependent fashion we constructed the strains SP 1212 ($h^{-S}$ mts2 cdc25(HA)$_3$ leu1-32) and SP 1213 ($h^{-S}$ pub1::ura4 mts2 cdc25(HA)$_3$ura4D18 leu1-32). These strains have either wild type pub1 (SP 1212) or the pub1 disruption (SP 1213) present in an mts2 mutant background. To ensure the specificity of the immunological detection of cdc25, both strains have the wild type cdc25 gene replaced by a cdc25 gene tagged with a triple tandem copy of the hemagglutinin epitope (HA). Cultures of both SP 1212 and SP 1213 were grown to early log phase in YEA at 25° C. Both cultures were then shifted to restrictive temperature and aliquotes removed at the times indicated. Lysates prepared from these time points were analyzed by Western blot using the 12CA5 anti HA monoclonal antibody to detect cdc25. At both permissive and restrictive temperatures, mts2 mutants accumulate a ladder of higher molecular weight species of cdc25. Incubation at restrictive temperature appears to slightly increase the abundance of high molecular weight cdc25 species, but otherwise have little effect. In contrast, in a pub1 disruption background no accumulation of higher molecular weight species of cdc25 is observed. If the exposure is extended for a prolonged period of time however, a faint ladder of cdc25 higher molecular weight species can be seen in a pub1 disruption background. We estimate that disruption of pub1 reduces the accumulation of cdc25 higher molecular weight species at least 10 fold. No immunological crossreactivity was detected in congenic control strains lacking hemagglutinin epitope tagged cdc25.

To determine if the higher molecular weight cdc25 species accumulated in an mts2 mutant were the result of ubiquitination, we analyzed cdc25 immunoprecipitates by Western blot for the presence of ubiquitin. Mid log cultures of both SP 1212 and SP 1213 were incubated at restrictive temperature for 3 hours and lysates prepared. Cdc25 was immunoprecipitated from each lysate. The immunoprecipitate from each strain was divided into two aliquotes, one analyzed by Western blot for the presence of cdc25 and the other for the presence of ubiquitin. At restrictive temperature mts2 mutants accumulate a ladder of higher molecular weight cdc25 species in a pub1 dependent fashion. These higher molecular weight forms of cdc25 crossreact with an anti ubiquitin antibody indicating that they are ubiquitinated forms of cdc25. The antigenicity of the cdc25 ubiquitin conjugates differs for anti HA and anti ubiquitin antibodies. The anti ubiquitin antibody preferentially recognizes the higher molecular weight forms of ubiquitinated cdc25. This is consistent with multiple ubiquitination—as the molecular weight of the species increases there are more ubiquitin molecules per molecule of cdc25. Both the higher molecular weight forms of cdc25 and the anti-ubiquitin crossreactive species are absent in a pub1 deletion background indicating that the predominant mechanism for ubiquitination of cdc25 requires pub1.

VIII. Pub1 is Thiol Ubiquitinated in vivo

If pub1 is functioning as an E6-AP like protein ubiquitin ligase, it should transfer ubiquitin from an E2 molecule to its target through a pub1 thiol ubiquitinated intermediate (Scheffner et al., (1993) *Cell* 75:495–505; Scheffner et al., (1995) *Nature* 373:81–83). We designed a simple experiment to trap this putative intermediate in vivo. If the synthesis of new target molecules is blocked, the ubiquitin degradation system may degrade all accessible target molecules. In the absence of target molecules, the components of the ubiquitin cycle which employ ubiquitin thioester intermediates may accumulate in their ubiquitin charged intermediate form. The thiol ubiquitinated intermediate of interest could then be isolated by simple immunoprecipitation. The formation of new target molecules can be prevented by inhibition of translation with cycloheximide (Novak and Mitchison, (1987) *J. Cell Sci.* 87:323–325). Since ubiquitin is recycled, blocking translation should not deplete the cellular stores of ubiquitin (Finley and Chau, (1991) supra).

Pub1 tagged on the C-terminus with a single hemagglutinin epitope was cloned into the Nde1-BamHI sites of a pREP1 forming pREP1pub1HA. This vector was introduced into apub1 deletion strain (SP 1208) in the presence of thiamin. Untagged pub1 cloned into the same sites of pREP1 (pREP1pub1) and introduced into the same parental strain was used as a control. Overexpression of pub1 from a pREP1 vector is lethal. The growth rate of SP 1208 containing either tagged or untagged pub1 in a pREP 1 vector is unaffected for 12 hours after shifting the cell to minus thiamin media. Cells bearing either plasmid arrest 18 hours after induction. SP 1208 containing either pREP1pub1 or pREP1pub1HA was grown in minimal liquid media in the presence of thiamin and then shifted to minus thiamin media for 10 hours. At this point cycloheximide was added to the cultures and aliquotes removed at the indicated times. The concentration of cycloheximide used was sufficient to reduce translation over 95% within 30 minutes (Novak and Mitchison, (1987) supra). Cell lysates were prepared from each time point in the presence of 1% LDS to prevent degradation and in the absence of any reducing agent to prevent displacement of the thioester bound ubiquitin. Gel samples from each time point were prepared in both the presence and absence of β mercaptoethanol. Samples prepared in the presence of β mercaptoethanol were subjected to electrophoresis in a standard Laemmeli gel at room temperature. Samples prepared in the absence of β mercaptoethanol were subjected to electrophoresis on a modified Laemmeli gel at 4° C. Western blots of both gels were performed using the anti HA monoclonal antibody 12CA5 to detect pub1. There is a time dependent accumulation of two slower migrating form of pub1 in cycloheximide treated SP 1208+pREP1pub1 14A cells in the absence of reducing agent. In the presence of reducing agents, both species are absent. The decrease in mobility exhibited by pub1-a could be accounted for by the addition of a single molecule of ubiquitin. Pub1-b migrates at the rate predicted for a molecule of approximately twice the molecular weight of pub1. Such a species could be the product of disulfide bond formation between two pub1 molecules or between pub1 and a protein of approximately the same molecular weight. In the absence of a hemagglutinin tag, no pub1 was detected.

If thiol ubiquitinated pub1 accumulates in cyclolleximide treated cells it should be possible to co-immunoprecipitate these two proteins in the absence of reducing agents. Logarithmically growing cultures of both SP 1208+pREP1pub1 and SP 1208+pREP1pub1HA were shifted to minus thiamine media for 10 hours to induce pub1 expression. Cycloheximide was then added. Lysates were prepared in the absence of reducing agents from both cultures immediately before and one hour after the addition of cycloheximide. The cells were lysed under strongly denaturing conditions (1% LDS) to disassociate non-covalent protein interactions and inhibit both isopeptidases and general proteolytic degradation activity (Haas et al., (1985) *J. Biol. Chem.* 260:4694–4703; Viersta et al., (1985) *J. Biol. Chem.* 260:12015–12021). Pub1 was immunoprecipitated from these lysates with the 12CA5 monoclonal antibody and the immunoprecipitates were divided into two aliquotes. One aliquote was incubated for 1 hour at 4° C. in RIPA buffer containing 20 mM DTT and then washed twice with the sarne buffer. The other aliquote was treated identically with RIPA buffer lacking DTT. Both DTT treated and untreated immunoprecipitates were analyzed by Western blot for the presence of pub and ubiquitin. One hour after treating the cells with cycloheximide, ubiquitin co-immunoprecipitates with pub1. Pub1 and ubiquitin are both absent from the cycloheximide treated untagged pub control, indicating that the co-immunoprecipitation of ubiquitin with pub1 is specific. The association between these two proteins is both DTT sensitive and dependent upon cycloheximide treatment of the cells. The amino acid sequence of ubiquitin encoded by the UBI3 genes of *S. cerevisiae* and *S. pombe* are identical, both lack cysteine residues (Ozkaynak et al., (1987) *EMBO J.* 6:1429–1439; D. Conklin and D. Beach, unpublished results). Unless *S. pombe* contains another isoform of ubiquitin with a cysteine residue, these two proteins cannot be linked by a disulfide bond. In addition, the association of ubiquitin with pub1 was sensitive to 0.1 M NaOH and refractile to 1M formic acid as are thioesters in general (Scheffner et al., 1995). Thus, the association of ubiquitin with pub is refractile to both 1% SDS and 1M formic acid, sensitive to both DTT and 0.1 M NaOH and coincident with the appearance of pub1-a, an approximately 5–10 kD DTT sensitive higher molecular weight form of pub1. These observations suggest the presence of a thioester bond between pub1 and ubiquitin in vivo.

IX. Cloning of Human Pub Homologs

Human homologs of the fisson yeast pub1 gene were isolated by in order to investigate the role of ubiquitination in the regulation of cdc25 in mammalian cells. The fission yeast pub1 sequence was used to search DNA sequence databases to identify human sequences to be used as probes for the isolation of cDNA clones corresponding to s-pub1. The PCR primer probes 5'-GAAATGTTGAATCCATACTAT and 5'-CCATATGCATTATGTTCAACACAG were used to amplify the h-pub1 sequence from a human keratinocyte cDNA library. Likewise, the PCR primers 5'-GACTTTAGTCATCCAGTGGAG and 5'-CAAAACCAAGAGCATTTCCCACGG were used to amplify the h-pub2 sequence from that same library. Altogether, five new human protein ubiquitin ligases, h-pub1-5, were isolated.

Two of the clones, h-pub1 and h-pub2 have been completely sequenced. These two genes were observed to have high homology to the yeast pub1 gene. Overall, the h-pub1 and h-pub2 proteins are 39% and 32% identical, respectively, to the amino acid sequence of the s-pub1.

In addition, we have observed in preliminary experiments that both h-pub1 and h-pub2 can become thiol-ubiquitinated in vitro.

X. Complementation of S-pub1 Disruptants with Human H-pub1 Protein

The biological activity of the h-pub1 gene was analyzed in a yeast complementation assay. Fission yeast strains in which pub1 and wee1 are simultaneously inactivated (pub1::ura wee1-50, described above) undergo pre-mature entry into mitosis. This is manifested by initiation of nuclear division at a small cell size, and is a lethal event. The human pub1 gene was expressed under control of the fission yeast nmt1 promoter and transformed into this double mutant strain. These transformants (pub1::ura wee1-50 h-pub1) were then grown under selective conditions at either permissive (25° C.) or non-permissive (36° C.) conditions. The h-pub1 protein was found to complement the loss of the fission yeast gene and to restore the cell size at mitosis to that of a wild-type cell. This suggests that h-pub1 is a biologically acitive, functional homolog of yeast pub1.

EXPERIMENTAL PROCEDURES

Strains and Media

All *S. pombe* strains were derived from the wild type strains originally described by Leupold (1970). All strains used in this study are listed in Table 1. *S. pombe* was grown in standard YE, YEA and PM media (Beach et at., (1985) *Nature* 300:706–709) containing additional leucine as described at 150 μg/ml. Media referred to as thiamine (+) was supplemented with 20 μM thiamine. Standard *S. pombe* genetic procedures were followed (Glutz et al., (1974) *Handbook of Genetics* 1, R. C. King ed. New York Plenum Press pp 395–446).

Cloning Sequencing and Mapping Pub1

An *S. pombe* cDNA library cloned into the Notl site of λZAP2 was immunologically screened with the anti-phosphotyrosine monoclonal antibody (UBI) (Lindberg et al., (1988) supra; Lindberg and Pasquale, (1991) supra; Druker et al., (1989) *New Eng. J. Med.* 321:1383–1391). Two hundred and fifty thousand plaques were screened and two putative positive clones were identified which were capable of generating anti-phosphotyrosine crossreactive polypeptides upon induction in *E. coli* as determined by Western blot analysis. Pub1 was one of these genes. The originally isolated pub1 insert was used to rescreen the λZAP2 *S. pombe* cDNA library by hybridization to obtain a full length cDNA.

A series of unidirectional deletions of both the original pub1 isolate and full length pub1 cDNA were constructed in either pBluescript SK- or pBluescript KS- (Henikoff, (1987) *Meth. Enzymol.* 155:156–165). Both strands of the cDNA clones were sequenced with a semiautomatic DNA sequencer (ABI 373A DNA sequencer). The pedicted amino acid sequence was generated by an Intelligenetics program translation of the cDNA sequence. A blast search of Genbank was then performed to identify proteins with similar sequences.

To physically map the pub1 gene we probed a collection of contiguous cosmid clones spanning the *S. pombe* genome with the 2.8 kb pub1 cDNA (Mizukami et al., (1993) *Cell* 73:121–132). Three overlapping cosmids, 323, 437 and 1187 hybridized to our probe indicating that pub1 is on the right arm of chromosome 1 near the centromere.

Gene Disruption

A 948 bp Sal1-Nsi1 fragment of the pub1 cDNA was replaced with the 1.8 kb ura4 gene. The resulting 3.7 kb disrupted cDNA isolated as a Not1 fragment was introduced the diploid strain SP826. Seventeen of the one hundred Ura+ transformants screened were unable to form single colonies in the presence of FOA indicating that the Ura+ phenotype was stable and consequently that the disrupted gene had been integrated. Seven of the ten Ura+ strains analyzed by Southern blot analysis carried both one copy of the pub 1, disruption and one copy of the wild type gene. Colonies from one of these strains were screened by iodine staining for the ability to sporulate—a consequence of conversion of the mat locus from h+N/h+N to h90/h+N. Tetrads from this diploid were disected and found produce four viable progeny.

Southern and Northern Analysis

Genomic *S. pombe* DNA was isolated from strains 972 and SP 1207, digested with EcoR1 and Southern blot analysis performed (Moreno et al., (1991) *Meth. Enzymol.* 194:795–823; Sambrook et al., (1989) *Molecular Cloning: A Laboratory Manual*, second ed.). The 2.1 kb Eco R1 fragment from the pub1 cDNA was used as a probe.

Total *S. pombe* RNA was isolated according to Caligari (personal communication). Ten milliliter cultures of both 972 and SP 1207 were grown to mid log in YEA at 30° C. and harvested. The cells were washed once with water and resuspended in a lysis buffer composed of 100 μl TLSE (10 mM TrisHCl pH 7.5, 500 mM LiCl, 1 mM EDTA, 1% lithium lauryl sulfate) containing 1.7 mg/ml Heparin. One hundred microliters of phenol were added and the cells were lysed by vortexing for five minutes in the presence of glass beads. Four hundred microliters of both TSLE and phenol were then added and the mixture was vortexed once again briefly. The aqueous phase was then extracted twice with phenol and once with phenol/chloroform/isoamyl alcohol. The RNA was the precipitated with 2.5 volumes of ethanol. A second ethanol precipitation was then performed to reduce salt levels. Northern blot analysis was performed (Sambrook, et al., (1989) supra). Full length pub1, cdc25 and ura4 $^{32}$P labeled by random priming were used as probes as indicated in the text.

Epitope Tagging Pub1

The pub1 cDNA was used as a template for a PCR reaction which introduced an Nde1 site at the initiating methionine and a Spe1 site immediately before the translational stop of the pub1. The Nde1/Spe1 pub1 fragment was then cloned into the Nde1/Spe1 sites of the bacterial expression vector pETSC/HA.1 which contains a single hemagglutinin epitope bounded by an Spe1 site on the 5 prime end and a stop codon followed by a BamH1 site on the 3 prime end. The resulting construct fused the C terminus of pub1 to the 11 amino acid peptide TSYPYDVPDYA containing a single hemagglutinin epitope preceeded by the amino acids TS. The N terminal Nde1/BamH1 fragment of this epitope tagged pub1 was cloned into the Nde1/BamH1 sites of the *S. pombe* expression vector pREP1 and the C terminal BamH1 fragment was then cloned into the BamH1 site of the resulting construct. The final construct pREP1pub1.HA consists of the pub1 ORF with a C terminal 11 ammo acid extension containing the HA epitope cloned into the Nde1/BamH1 sites of pREP1.

Immunoprecipitation and Immunoblotting of Cdc25

*S. pombe* extracts for immunoblotting of cdc25 were prepared as previously described (Ducommun et al., (1990) supra). Cell pellets were resuspended in twice their volume of buffer I (50 mM Tris-HCl pH=8, 8 M urea, 1 mM EGTA, 5 mM EDTA, 0.1 mM PMSF, 1 μg/ml leupeptin, 10 μg/ml soybean trypsin inhibitor, 1 μg/ml aprotitin and 10 μg/ml TPCK (tosyl phenylalanine chloromethyl ketone). The cells were lysed by vortexing in the presence of glass beads and the soluble proteins were recovered by centifugation. Samples were immediately removed and boiled for 3 minutes in Laemmili sample buffer. The protein concentration of the lysate was then determined by Bradford dye binding assay using γ globulin as a standard (Bradford, (1976) *Anal. Biochem.* 72:248–254). The proteins were separated electrophoretically on an 8% Laemmli gel and transfered to nitrocellulose (Schleicher and Schuel,0.45, um) with a Millipore semi-dry transfer apparatus (Laemmli, (1970) *Nature* 277:680–685). All manipulations of the cdc25 blots were performed at room temperature. The blots were blocked with TBST (10 mM Tris-HCl pH 7.5, 150 mM NaCl, 0.05% Tween 20) containing 3% non fat dry milk and 10 mM sodium azide overnight.

The blot containing untagged cdc25 was then incubated in the blocking buffer containing a 1:500 dilution of an affinity purified anti-cdc25 polyclonal antibody B 1 for four hours (Ducornmun et al., (1990) supra). After 5 ten minute washes in TBST, the blot was incubated for 30 minutes in 16 ng/ml peroxidase conjugated Affi Pure goat anti rabbit IgG Fc fragment specific (Jackson Immunoresearch) in TBST containing 3% milk. After four 10 minute washes in TBST followed by one ten minute wash in TBS (10 mM tris-HCl pH 7.5, 150 mM NaCl), cdc25 was detected by ECL (Amersham).

Blots containing hemagglutinin tagged cdc25 were incubated for 2 hours in the blocking buffer containing 100 ng/ml 12CA5 anti-HA monoclonal antibody (Boehringer and Mannheim). After 5 ten minute washes in TBST, the blots were incubated for 1 hour in 100 ng/ml peroxidase conjugated Affi Pure goat anti mouse IgG Fc fragment specific (Jackson Immunoresearch) in TBST containing 3% milk. After four ten minute washes in TBST followed by one wash in TBS, cdc25 was detected by ECL (Amersham).

To immunoprecipitate cdc25 we modified the previously described protocol (Ducommum et al., (1990) supra). Cell pellets were resuspended in 4 volumes of ice cold buffer 2 (25 mM Tris-HCI pH 8.0, 60 mM β-glycerol phosphate, 15 mM para-nitrophenylphosphate, 0.1 mM orthovanadate and 0.1% Triton X 100) containing the same protease inhibitors as in buffer I. The cells were lysed by vortexing in the presence of glass beads at 4° C. and the extracts immediately made 1% SDS and boiled for 3 minutes. The extracts were then diluted 10 fold in RIPA buffer lacking SDS and soluble proteins recovered by centrifugation at 10,000 g for 15 minutes at 4° C. The protein concentration was then determined by Bradford assay (Bradford, (1976) supra). The lysates were preincubated with protein A agarose (Pierce) for 30 minutes and centrifuged at 10,000 g for 10 minutes both at 4° C. Affinity purified B1 anti-cdc25 polyclonal antibody was added to the supernatant and the mixture was incubated overnight at 4° C. on a rotator. Non specific precipitated proteins were removed by centrifugation at 4° C. for 5 minutes at 10,000 g. The supernatant was incubated with protein A agarose for 30 minutes at 4° C. and the immunoprecipitates collected by low speed centrifugation. The immunoprecipitates were then washed five times with RIPA buffer after which the beads were resuspended in Laemmli sample buffer and boiled for 3 minutes. The supernatant was subjected to electrophoresis in an 8% Laemmli gel. Western blot analysis was subsequently performed to test for the presence of both ubiquitinated and hemagglutinin tagged cdc25.

Immunoblot Detection of Ubiquitin

The same protocol was used to detect both free ubiquitin and ubiquitinated cdc25. The ge] of interest was transferred by the semi dry Milliblot-SDE system (Millipore) to a sheet of 0.2 µm nitrocellulose (Schleicher and Schuel) which has been hydrated overnight in distilled water. After the transfer the nitrocellulose is incubated in distilled water at 100° C. for 20 minutes (Swerdlow et al., (1986) *Anal. Biochem.* 156:147–153). All subsequent manipulations were done at room temperature. The blots were then blocked by overnight incubation with 3% BSA in TBST containing 10 mM sodium azide. The blots were incubated for 1 hour in blocking buffer containing an anti ubiquitin polyclonal antibody (Sigma) and subsequently washed five times for 10 minutes in TBST. The blots were then incubated with affinity purified HRP conjugated goat anti rabbit Fc (Jackson Immunoresearch) in TBST containing 3% BSA for 30 minutes. The blots were washed four times for ten minutes in TBST and then once in TBS. Ubiquitin was detected by ECL.

Immunoblotting and Immunoprecipitation of Thioester Ubiquitinated Pub1

Strain SP 1208 bearing either pREP1pub1HA or pREP1pub1 was grown in minimal media lacking thiamin for 10 hours to a density of $10^7$/ml after which cycloheximide was added to a final concentration of 100 µg/ml. Immediately before and 15, 30, 60, and 120 minutes after the addition of cycloheximide 50 ml aliquotes were removed from the culture, the cells harvested by centrifugation, washed once with water and the cell pellets kept in a dry ice/ethanol bath until the end of the time course. The cell pellets were then thawed and resuspended in 3 volumes of cold lysis buffer (50 mM HEPES-NaOH pH 7, 1% lithium lauryl sulfate, 150 mM NaCl, 10 mM iodoacetamide, 5 mM EDTA, 1 mM EGTA, 0.1 mM PMSF, 10,ug/ml leupeptin, 10 µg/ml soybean trypsin inhibitor, 1,ug/ml aprotitin and 10 µg/ml TPCK) (Hershko et al., (1982) *J. Biol. Chem.* 257:13964–13970; Haas et al., (1985) supra; Viestra et al., (1985) supra). The cells were lysed by vortexing in the presence of glass beads and the soluble proteins recovered by centrfugation at 10,000 g for 15 minutes at 4° C. The protein concentration was determined by Bradford assay (Bradford, (1976) supra). Two gel samples of identical protein concentration were prepared from each time point one using standard Laemmli sample buffer and the other a modified Laemmli sample buffer which lacked β-mercaptoethanol and had LDS in place of SDS. The standard Laemmli samples were subjected to electrophoresis in an 8% Laemmli gel at room temperature. The other samples were subjected to electrophoresis at 4° C. in a modified Laemmli gel in which LDS is substituted for SDS (McGrath et al., (1991) *EMBO J.* 10:227–236). Both gels were transferred to nitrocellulose and subjected to Western blot analysis with the 12CA5 anti-HA monoclonal antibody as described above.

To immunoprecipitate thioester ubiquitinated pub1, strain SP 1208 containing pREP1pub1HA or pREP1pub1 was grown in minimal media lacking thiamin at 30° C. for 10 hours to a density of $10^7$/ml. The culture was then made 100 µg/ml cycloheximide and incubated for an additional hour at 30° C. Aliquotes were removed immediately before: and 1 hour after the additon of cycloheximide. The cells were harvested washed once with distilled water and kept in a dry ice/ethanol bath until lysis. Lysates were prepared in buffer 2 as described above. The lysates were diluted ten fold with RIPA buffer containing the same protease inhibitors as buffer 2 and lacking SDS. The soluble proteins were recovered by centrifugation and the protein concentration determined by Bradford assay. The volume of lysates from each sample containing five mg of soluble protein were pre-cleared with protein A agarose (Pierce) and then incubated with 12CA5 anti HA monoclonal antibody for 1 hour at 4° C. on a rotator. The samples were then centrifuged at 4° C. for 10 minutes at 10,000 g to remove precipitated proteins and the supernatants incubated with protein A agarose for 30 minutes at 4° C. on a rotator. The immunoprecipitates were collected by low speed centrifugation and washed 5 times with a modified RIPA buffer containing the same protease inhibitors as buffer 2. The immunoprecipitates were then split into two equal aliquotes. One aliquote was incubated for 1 hour at 4° C. in RIPA buffer containing both protease inhibitors present in buffer I and 20 mM DTT and then washed twice the same buffer. The other aliquote was treated identically with the same buffer lacking DTT. The beads were resuspended in Laemmli sample buffer and boiled for 3 minutes. Samples from both aliquotes were run on both an 8% gel to detect pub1 and an 18% gel to detect free ubiquitin. Pub1 and ubiquitin Westerns were performed as described above.

Miscellaneous

Dapi (4,6 diamidino-2-phenylindole) staining of *S. pombe* cells was done according to (Moreno et. al., (1991) supra).

Pub1 was transcribed and translated in vitro using the TNT T7 coupled reticulocyte lysate system (Promega) in the presence of $^{35}$S Express (NEN).

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid comprising a nucleotide sequence encoding a pub polypeptide or fragment thereof, or a nucleotide sequence complementary thereto, said pub polypeptide including an amino acid sequence at least 80% identical to the amino acid sequence designated by one or more of SEQ ID No. 2 and SEQ ID No. 6, which pub polypeptide or fragment thereof possesses a ubiquitin ligase activity.

2. The nucleic acid of claim 1, wherein said pub polypeptide possesses a calcium binding motif.

3. The nucleic acid of claim 1, wherein said pub polypeptide ubiquitinates cdc25.

4. The nucleic acid of claim 1, wherein said pub polypeptide encoding nucleotide sequence is at least 90% identical to the amino acid sequence designated by SEQ ID No. 2.

5. The nucleic acid of claim 1, wherein said pub polypeptide encoding nucleotide sequence is at least 90% identical to the amino acid sequence designated by SEQ ID No. 6.

6. The nucleic acid of claim 1, wherein said pub polypeptide is a fusion protein.

7. The nucleic acid of claim 1, which nucleic acid hybridizes under stringent conditions to a nucleic acid probe having a sequence represented by at least 60 consecutive nucleotides of SEQ ID No. 1, or a sequence complementary thereto.

8. The nucleic acid of claim 1, wherein said pub polypeptide encoding nucleotide sequence hybridizes under stringent conditions to a nucleic acid probe having a sequence represented by at least 60 consecutive nucleotides of SEQ ID No. 1 or 5, or a sequence complementary thereto.

9. The nucleic acid of claim 1, further comprising a transcriptional regulatory sequence operably linked to said nucleotide sequence so as to render said nucleic acid suitable for use as an expression vector.

10. An expression vector, capable of replicating in at least one of a prokaryotic cell and eukaryotic cell, comprising the nucleic acid of claim 9.

11. A host cell transfected with the expression vector of claim 10 and expressing said recombinant polypeptide.

12. A method of producing a recombinant pub polypeptide comprising culturing the cell of claim 11 in a cell culture medium to express said recombinant polypeptide and isolating said recombinant polypeptide from said cell culture.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2208 base pairs
      (B) TYPE: nucleic acid
      (C) STRANDEDNESS: both
      (D) TOPOLOGY: linear (ii) MOLECULE TYPE: cDNA (ix) FEATURE:
      (A) NAME/KEY: CDS
      (B) LOCATION: 1..2205

(xi) SEQUENCE DESCRIPTION: SEQ ID NO:1:

```
ATG TCT AAC CCC GGA GGC CGG AGG AAC GGG CCC GTC AAG CTG CGC CTG        48
Met Ser Asn Pro Gly Gly Arg Arg Asn Gly Pro Val Lys Leu Arg Leu
 1               5                  10                  15

ACA GGA CTT CCT GAT CCA TTT GCT AAG GTG GTG GTT GAT GGA TCT GGG        96
Thr Gly Leu Pro Asp Pro Phe Ala Lys Val Val Val Asp Gly Ser Gly
             20                  25                  30

CAA TGC CAT TCT ACA GAT ACT GTG AAG AAT ACG CTT GAT CCA AAG TGG       144
Gln Cys His Ser Thr Asp Thr Val Lys Asn Thr Leu Asp Pro Lys Trp
         35                  40                  45

AAT CAG CAT TAT GAC CTG TAT ATT GGA AAG TCT GAT TCA GTT ACG ATC       192
Asn Gln His Tyr Asp Leu Tyr Ile Gly Lys Ser Asp Ser Val Thr Ile
     50                  55                  60

AGT GTA TGG AAT CAC AAG AAG ATC CAT AAG AAA CAA GGT GCT GGA TTT       240
Ser Val Trp Asn His Lys Lys Ile His Lys Lys Gln Gly Ala Gly Phe
 65                  70                  75                  80

CTC GGT TGT GTT CGT CTT CTT TCC AAT GCC ATC AAC CGG CTC AAA GAC       288
Leu Gly Cys Val Arg Leu Leu Ser Asn Ala Ile Asn Arg Leu Lys Asp
                 85                  90                  95

ACT GGT TAT CAG AGG TTG GAT TTA TGC AAA CTC GGG CCA AAT GAC AAT       336
Thr Gly Tyr Gln Arg Leu Asp Leu Cys Lys Leu Gly Pro Asn Asp Asn
            100                 105                 110

GAT ACA GTT AGA GGA CAG ATA GTA GTA AGT CTT CAG TCC AGA GAC CGA       384
Asp Thr Val Arg Gly Gln Ile Val Val Ser Leu Gln Ser Arg Asp Arg
        115                 120                 125

ATA GGC ACA GGA GGA CAA GTT GTG GAC TGC AGT CGT TTA TTT GAT AAC       432
Ile Gly Thr Gly Gly Gln Val Val Asp Cys Ser Arg Leu Phe Asp Asn
    130                 135                 140

GAT TTA CCA GAC GGC TGG GAA GAA AGG AGA ACC GCC TCT GGA AGA ATC       480
Asp Leu Pro Asp Gly Trp Glu Glu Arg Arg Thr Ala Ser Gly Arg Ile
145                 150                 155                 160

CAG TAT CTA AAC CAT ATA ACA AGA ACT ACG CAA TGG GAG CGC CCA ACA       528
Gln Tyr Leu Asn His Ile Thr Arg Thr Thr Gln Trp Glu Arg Pro Thr
                165                 170                 175

CGA CCG GCA TCC GAA TAT TCT AGC CCT GGC AGA CCT CTT AGC TGC TTT       576
Arg Pro Ala Ser Glu Tyr Ser Ser Pro Gly Arg Pro Leu Ser Cys Phe
            180                 185                 190

GTT GAT GAG AAC ACT CCA ATT AGT GGA ACA AAT GGT GCA ACA TGT GGA       624
Val Asp Glu Asn Thr Pro Ile Ser Gly Thr Asn Gly Ala Thr Cys Gly
        195                 200                 205

CAG TCT TCA GAT CCC AGG CTG GCA GAG AGG AGA GTC AGG TCA CAA CGA       672
Gln Ser Ser Asp Pro Arg Leu Ala Glu Arg Arg Val Arg Ser Gln Arg
    210                 215                 220
```

```
CAT AGA AAT TAC ATG AGC AGA ACA CAT TTA CAT ACT CCT CCA GAC CTA        720
His Arg Asn Tyr Met Ser Arg Thr His Leu His Thr Pro Pro Asp Leu
225                 230                 235                 240

CCA GAA GGC TAT GAA CAG AGG ACA ACG CAA CAA GGC CAG GTG TAT TTC        768
Pro Glu Gly Tyr Glu Gln Arg Thr Thr Gln Gln Gly Gln Val Tyr Phe
                245                 250                 255

TTA CAT ACA CAG ACT GGT GTG AGC ACA TGG CAT GAT CCA AGA GTG CCC        816
Leu His Thr Gln Thr Gly Val Ser Thr Trp His Asp Pro Arg Val Pro
            260                 265                 270

AGG GAT CTT AGC AAC ATC AAT TGT GAA GAG CTT GGT CCA TTG CCT CCT        864
Arg Asp Leu Ser Asn Ile Asn Cys Glu Glu Leu Gly Pro Leu Pro Pro
        275                 280                 285

GGA TGG GAG ATC CGT AAT ACG GCA ACA GGC AGA GTT TAT TTC GTT GAC        912
Gly Trp Glu Ile Arg Asn Thr Ala Thr Gly Arg Val Tyr Phe Val Asp
    290                 295                 300

CAT AAC AAC AGA ACA ACA CAA TTT ACA GAT CCT CGG CTG TCT GCT AAC        960
His Asn Asn Arg Thr Thr Gln Phe Thr Asp Pro Arg Leu Ser Ala Asn
305                 310                 315                 320

TTG CAT TTA GTT TTA AAT CGG CAG AAC CAA TTG AAA GAC CAA CAG CAA       1008
Leu His Leu Val Leu Asn Arg Gln Asn Gln Leu Lys Asp Gln Gln Gln
                325                 330                 335

CAG CAA GTG GTA TCG TTA TGT CCT GAT GAC ACA GAA TGC CTG ACA GTC       1056
Gln Gln Val Val Ser Leu Cys Pro Asp Asp Thr Glu Cys Leu Thr Val
            340                 345                 350

CCA AGG TAC AAG CGA GAC CTG GTT CAG AAA CTA AAA ATT TTG CGG CAA       1104
Pro Arg Tyr Lys Arg Asp Leu Val Gln Lys Leu Lys Ile Leu Arg Gln
        355                 360                 365

GAA CTT TCC CAA CAA CAG CCT CAG GCA GGT CAT TGC CGC ATT GAG GTT       1152
Glu Leu Ser Gln Gln Gln Pro Gln Ala Gly His Cys Arg Ile Glu Val
    370                 375                 380

TCC AGG GAA GAG ATT TTT GAG GAA TCA TAT CGA CAG GTC ATG AAA ATG       1200
Ser Arg Glu Glu Ile Phe Glu Glu Ser Tyr Arg Gln Val Met Lys Met
385                 390                 395                 400

AGA CCA AAA GAT CTC TGG AAG CGA TTA ATG ATA AAA TTT CGT GGA GAA       1248
Arg Pro Lys Asp Leu Trp Lys Arg Leu Met Ile Lys Phe Arg Gly Glu
                405                 410                 415

GAA GGC CTT GAC TAT GGA GGC GTT GCC AGG GAA TGG TTG TAT CTC TTG       1296
Glu Gly Leu Asp Tyr Gly Gly Val Ala Arg Glu Trp Leu Tyr Leu Leu
            420                 425                 430

TCA CAT GAA ATG TTG AAT CCA TAC TAT GGC CTC TTC CAG TAT TCA AGA       1344
Ser His Glu Met Leu Asn Pro Tyr Tyr Gly Leu Phe Gln Tyr Ser Arg
        435                 440                 445

GAT GAT ATT TAT ACA TTG CAG ATC AAT CCT GAT TCT GCA GTT AAT CCG       1392
Asp Asp Ile Tyr Thr Leu Gln Ile Asn Pro Asp Ser Ala Val Asn Pro
    450                 455                 460

GAA CAT TTA TCC TAT TTC CAC TTT GTT GGA CGA ATA ATG GGA ATG GCT       1440
Glu His Leu Ser Tyr Phe His Phe Val Gly Arg Ile Met Gly Met Ala
465                 470                 475                 480

GTG TTT CAT GGA CAT TAT ATT GAT GGT GGT TTC ACA TTG CCT TTT TAT       1488
Val Phe His Gly His Tyr Ile Asp Gly Gly Phe Thr Leu Pro Phe Tyr
                485                 490                 495

AAG CAA TTG CTT GGG AAG TCA ATT ACC TTG GAT GAC ATG GAG TTA GTA       1536
Lys Gln Leu Leu Gly Lys Ser Ile Thr Leu Asp Asp Met Glu Leu Val
            500                 505                 510

GAT CCG GAT CTT CAC AAC AGT TTA GTG TGG ATA CTT GAG AAT GAT ATT       1584
Asp Pro Asp Leu His Asn Ser Leu Val Trp Ile Leu Glu Asn Asp Ile
        515                 520                 525

ACA GGT GTT TTG GAC CAT ACC TTC TGT GTT GAA CAT AAT GCA TAT GGT       1632
Thr Gly Val Leu Asp His Thr Phe Cys Val Glu His Asn Ala Tyr Gly
```

```
              530                 535                 540
GAA ATT ATT CAG CAT GAA CTT AAA CCA AAT GGC AAA AGT ATC CCT GTT      1680
Glu Ile Ile Gln His Glu Leu Lys Pro Asn Gly Lys Ser Ile Pro Val
545                     550                 555                 560

AAT GAA GAA AAT AAA AAA GAA TAT GTC AGG CTC TAT GTG AAC TGG AGA      1728
Asn Glu Glu Asn Lys Lys Glu Tyr Val Arg Leu Tyr Val Asn Trp Arg
                    565                 570                 575

TTT TTA CGG GGC ATT GAG GCT CAA TTC TTG GCT CTG CAG AAA GGA TTT      1776
Phe Leu Arg Gly Ile Glu Ala Gln Phe Leu Ala Leu Gln Lys Gly Phe
                580                 585                 590

AAT GAA GTA ATT CCA CAA CAT CTG CTG AAG ACA TTT GAT GAG AAG GAG      1824
Asn Glu Val Ile Pro Gln His Leu Leu Lys Thr Phe Asp Glu Lys Glu
            595                 600                 605

TTA GAG CTC ATT ATT TGT GGA CTT GGA AAG ATA GAT GTT AAT GAC TGG      1872
Leu Glu Leu Ile Ile Cys Gly Leu Gly Lys Ile Asp Val Asn Asp Trp
610                 615                 620

AAG GTA AAC ACC CGG TTA AAA CAC TGT ACA CCA GAC AGC AAC ATT GTC      1920
Lys Val Asn Thr Arg Leu Lys His Cys Thr Pro Asp Ser Asn Ile Val
625                 630                 635                 640

AAA TGG TTC TGG AAA GCT GTG GAG TTT TTT GAT GAA GAG CGA CGA GCA      1968
Lys Trp Phe Trp Lys Ala Val Glu Phe Phe Asp Glu Glu Arg Arg Ala
                    645                 650                 655

AGA TTG CTT CAG TTT GTG ACA GGA TCC TCT CGA GTG CCT CTG CAG GGC      2016
Arg Leu Leu Gln Phe Val Thr Gly Ser Ser Arg Val Pro Leu Gln Gly
                660                 665                 670

TTC AAA GCA TTG CAA GGT GCT GCA GGC CCG AGA CTC TTT ACC ATA CAC      2064
Phe Lys Ala Leu Gln Gly Ala Ala Gly Pro Arg Leu Phe Thr Ile His
            675                 680                 685

CAG ATT GAT GCC TGC ACT AAC AAC CTG CCG AAA GCC CAC ACT TGC TTC      2112
Gln Ile Asp Ala Cys Thr Asn Asn Leu Pro Lys Ala His Thr Cys Phe
690                 695                 700

AAT CGA ATA GAC ATT CCA CCC TAT GAA AGC TAT GAA AAG CTA TAT GAA      2160
Asn Arg Ile Asp Ile Pro Pro Tyr Glu Ser Tyr Glu Lys Leu Tyr Glu
705                 710                 715                 720

AAG CTG CTA ACA GCC ATT GAA GAA ACA TGT GGA TTT GCT GTG GAA          2205
Lys Leu Leu Thr Ala Ile Glu Glu Thr Cys Gly Phe Ala Val Glu
                    725                 730                 735

TGA                                                                  2208
```

(2) INFORMATION FOR SEQ ID NO:2:

(i) SEQUENCE CHARACTERISTICS:
        (A) LENGTH: 735 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Asn Pro Gly Gly Arg Arg Asn Gly Pro Val Lys Leu Arg Leu
1               5                   10                  15

Thr Gly Leu Pro Asp Pro Phe Ala Lys Val Val Asp Gly Ser Gly
            20                  25                  30

Gln Cys His Ser Thr Asp Thr Val Lys Asn Thr Leu Asp Pro Lys Trp
        35                  40                  45

Asn Gln His Tyr Asp Leu Tyr Ile Gly Lys Ser Asp Ser Val Thr Ile
    50                  55                  60

Ser Val Trp Asn His Lys Lys Ile His Lys Gln Gly Ala Gly Phe
65                  70                  75                  80
```

-continued

```
Leu Gly Cys Val Arg Leu Leu Ser Asn Ala Ile Asn Arg Leu Lys Asp
                 85                  90                  95
Thr Gly Tyr Gln Arg Leu Asp Leu Cys Lys Leu Gly Pro Asn Asp Asn
            100                 105                 110
Asp Thr Val Arg Gly Gln Ile Val Ser Leu Gln Ser Arg Asp Arg
            115                 120                 125
Ile Gly Thr Gly Gly Gln Val Val Asp Cys Ser Arg Leu Phe Asp Asn
    130                 135                 140
Asp Leu Pro Asp Gly Trp Glu Glu Arg Thr Ala Ser Gly Arg Ile
145                 150                 155                 160
Gln Tyr Leu Asn His Ile Thr Arg Thr Thr Gln Trp Glu Arg Pro Thr
                165                 170                 175
Arg Pro Ala Ser Glu Tyr Ser Ser Pro Gly Arg Pro Leu Ser Cys Phe
            180                 185                 190
Val Asp Glu Asn Thr Pro Ile Ser Gly Thr Asn Gly Ala Thr Cys Gly
            195                 200                 205
Gln Ser Ser Asp Pro Arg Leu Ala Glu Arg Arg Val Arg Ser Gln Arg
    210                 215                 220
His Arg Asn Tyr Met Ser Arg Thr His Leu His Thr Pro Pro Asp Leu
225                 230                 235                 240
Pro Glu Gly Tyr Glu Gln Arg Thr Thr Gln Gln Gly Gln Val Tyr Phe
                245                 250                 255
Leu His Thr Gln Thr Gly Val Ser Thr Trp His Asp Pro Arg Val Pro
            260                 265                 270
Arg Asp Leu Ser Asn Ile Asn Cys Glu Glu Leu Gly Pro Leu Pro Pro
            275                 280                 285
Gly Trp Glu Ile Arg Asn Thr Ala Thr Gly Arg Val Tyr Phe Val Asp
    290                 295                 300
His Asn Asn Arg Thr Thr Gln Phe Thr Asp Pro Arg Leu Ser Ala Asn
305                 310                 315                 320
Leu His Leu Val Leu Asn Arg Gln Asn Gln Leu Lys Asp Gln Gln Gln
                325                 330                 335
Gln Gln Val Val Ser Leu Cys Pro Asp Asp Thr Glu Cys Leu Thr Val
            340                 345                 350
Pro Arg Tyr Lys Arg Asp Leu Val Gln Lys Leu Lys Ile Leu Arg Gln
            355                 360                 365
Glu Leu Ser Gln Gln Gln Pro Gln Ala Gly His Cys Arg Ile Glu Val
    370                 375                 380
Ser Arg Glu Glu Ile Phe Glu Glu Ser Tyr Arg Gln Val Met Lys Met
385                 390                 395                 400
Arg Pro Lys Asp Leu Trp Lys Arg Leu Met Ile Lys Phe Arg Gly Glu
                405                 410                 415
Glu Gly Leu Asp Tyr Gly Gly Val Ala Arg Glu Trp Leu Tyr Leu Leu
            420                 425                 430
Ser His Glu Met Leu Asn Pro Tyr Tyr Gly Leu Phe Gln Tyr Ser Arg
            435                 440                 445
Asp Asp Ile Tyr Thr Leu Gln Ile Asn Pro Asp Ser Ala Val Asn Pro
    450                 455                 460
Glu His Leu Ser Tyr Phe His Phe Val Gly Arg Ile Met Gly Met Ala
465                 470                 475                 480
Val Phe His Gly His Tyr Ile Asp Gly Gly Phe Thr Leu Pro Phe Tyr
                485                 490                 495
Lys Gln Leu Leu Gly Lys Ser Ile Thr Leu Asp Asp Met Glu Leu Val
```

```
                    500               505               510
Asp Pro Asp Leu His Asn Ser Leu Val Trp Ile Leu Glu Asn Asp Ile
        515               520               525

Thr Gly Val Leu Asp His Thr Phe Cys Val Glu His Asn Ala Tyr Gly
        530               535               540

Glu Ile Ile Gln His Glu Leu Lys Pro Asn Gly Lys Ser Ile Pro Val
545               550               555               560

Asn Glu Glu Asn Lys Lys Glu Tyr Val Arg Leu Tyr Val Asn Trp Arg
                565               570               575

Phe Leu Arg Gly Ile Glu Ala Gln Phe Leu Ala Leu Gln Lys Gly Phe
        580               585               590

Asn Glu Val Ile Pro Gln His Leu Leu Lys Thr Phe Asp Glu Lys Glu
        595               600               605

Leu Glu Leu Ile Ile Cys Gly Leu Gly Lys Ile Asp Val Asn Asp Trp
610               615               620

Lys Val Asn Thr Arg Leu Lys His Cys Thr Pro Asp Ser Asn Ile Val
625               630               635               640

Lys Trp Phe Trp Lys Ala Val Glu Phe Asp Glu Glu Arg Arg Ala
                645               650               655

Arg Leu Leu Gln Phe Val Thr Gly Ser Ser Arg Val Pro Leu Gln Gly
        660               665               670

Phe Lys Ala Leu Gln Gly Ala Ala Gly Pro Arg Leu Phe Thr Ile His
        675               680               685

Gln Ile Asp Ala Cys Thr Asn Asn Leu Pro Lys Ala His Thr Cys Phe
        690               695               700

Asn Arg Ile Asp Ile Pro Pro Tyr Glu Ser Tyr Glu Lys Leu Tyr Glu
705               710               715               720

Lys Leu Leu Thr Ala Ile Glu Glu Thr Cys Gly Phe Ala Val Glu
                725               730               735

(2) INFORMATION FOR SEQ ID NO:3:

(i) SEQUENCE CHARACTERISTICS:
        (A) LENGTH: 2848 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 238..2535

(xi) SEQUENCE DESCRIPTION: SEQ ID NO:3:

AACGACGGAT TCAAAATTG TGCGCTGAAA GACGAATTTG ATTAAGGATT CCTTTTGTAG    60

TTCTTTTTTA TTTATTCGTT CCCGAAAAAA GCGTTTTTGT ATCAAATAGA AAGGATAAAA   120

CGGCCTTAAT TGAAAGTTTT TTTTGCAAGC ACAAATACTT GACTTTCTTT GGGAAATTGG   180

CTTTTTTTTA TTATCCAAAA GCAACGCTGG TTTGAAATTT TACCATCTTT TCCCCCT      237

ATG TCA AAC TCA GCT CAA TCT CGT CGA ATT CGA GTA ACA ATT GTT GCT    285
Met Ser Asn Ser Ala Gln Ser Arg Arg Ile Arg Val Thr Ile Val Ala
 1               5                  10                  15

GCT GAT GGC CTT TAC AAA CGA GAT GTG TTT CGT TTT CCT GAC CCG TTT    333
Ala Asp Gly Leu Tyr Lys Arg Asp Val Phe Arg Phe Pro Asp Pro Phe
                20                  25                  30

GCG GTA CTA ACA GTG GAT GGT GAG CAA ACA CAT ACC ACA ACT GCT ATC    381
Ala Val Leu Thr Val Asp Gly Glu Gln Thr His Thr Thr Thr Ala Ile
```

-continued

```
                35                     40                       45
AAA AAG ACG TTA AAC CCT TAT TGG AAT GAG ACT TTT GAA GTT AAT GTT     429
Lys Lys Thr Leu Asn Pro Tyr Trp Asn Glu Thr Phe Glu Val Asn Val
         50                      55                      60

ACA GAT AAT AGC ACC ATT GCG ATT CAG GTG TTC GAT CAG AAA AAA TTT     477
Thr Asp Asn Ser Thr Ile Ala Ile Gln Val Phe Asp Gln Lys Lys Phe
 65                      70                      75              80

AAG AAA AAA GGC CAA GGC TTT CTA GGA GTG ATA AAT CTT CGT GTT GGA     525
Lys Lys Lys Gly Gln Gly Phe Leu Gly Val Ile Asn Leu Arg Val Gly
                     85                      90                      95

GAT GTG CTC GAT CTC GCC ATT GGA GGT GAT GAA ATG TTG ACC CGC GAT     573
Asp Val Leu Asp Leu Ala Ile Gly Gly Asp Glu Met Leu Thr Arg Asp
                100                     105                     110

TTG AAA AAG TCA AAT GAG AAT ACA GTA GTT CAT GGC AAG ATA ATC ATA     621
Leu Lys Lys Ser Asn Glu Asn Thr Val Val His Gly Lys Ile Ile Ile
            115                     120                     125

AAC TTA TCA ACG ACT GCG CAG TCA ACC TTA CAG GTT CCA TCC AGT GCA     669
Asn Leu Ser Thr Thr Ala Gln Ser Thr Leu Gln Val Pro Ser Ser Ala
        130                     135                     140

GCA TCA GGT GCA CGT ACC CAA CGT ACT AGC ATT ACC AAT GAC CCG CAA     717
Ala Ser Gly Ala Arg Thr Gln Arg Thr Ser Ile Thr Asn Asp Pro Gln
145                     150                     155                     160

AGC TCA AAA AGT AGC AGT GTG TCT CGT AAC CCT GCT TCC TCT CGT GCT     765
Ser Ser Lys Ser Ser Ser Val Ser Arg Asn Pro Ala Ser Ser Arg Ala
                    165                     170                     175

GGT TCA CCT ACC CGC GAC AAC GCA CCT GCT GCT TCC CCT GCT AGT TCA     813
Gly Ser Pro Thr Arg Asp Asn Ala Pro Ala Ala Ser Pro Ala Ser Ser
                180                     185                     190

GAA CCT CGC ACA TTT AGT TCA TTT GAA GAT CAA TAT GGG CGC CTT CCT     861
Glu Pro Arg Thr Phe Ser Ser Phe Glu Asp Gln Tyr Gly Arg Leu Pro
            195                     200                     205

CCT GGA TGG GAA AGA CGT ACC GAT AAT CTT GGC CGA ACT TAT TAT GTA     909
Pro Gly Trp Glu Arg Arg Thr Asp Asn Leu Gly Arg Thr Tyr Tyr Val
        210                     215                     220

GAT CAT AAT ACA AGA AGC ACA ACG TGG ATT CGC CCC AAC CTA AGT TCT     957
Asp His Asn Thr Arg Ser Thr Thr Trp Ile Arg Pro Asn Leu Ser Ser
225                     230                     235                     240

GTT GCC GGA GCA GCC GCA GCC GAA TTG CAT AGT AGT GCA TCG TCT GCG    1005
Val Ala Gly Ala Ala Ala Ala Glu Leu His Ser Ser Ala Ser Ser Ala
                    245                     250                     255

AAT GTT ACC GAA GGT GTT CAA CCT TCC TCT AGC AAT GCA GCT CGT CGT    1053
Asn Val Thr Glu Gly Val Gln Pro Ser Ser Ser Asn Ala Ala Arg Arg
                260                     265                     270

ACA GAA GCT AGT GTT TTG ACC TCT AAC GCT ACT ACT GCT GGT TCA GGA    1101
Thr Glu Ala Ser Val Leu Thr Ser Asn Ala Thr Thr Ala Gly Ser Gly
            275                     280                     285

GAG CTT CCA CCG GGA TGG GAG CAA AGG TAT ACA CCA GAG GGT CGA CCC    1149
Glu Leu Pro Pro Gly Trp Glu Gln Arg Tyr Thr Pro Glu Gly Arg Pro
        290                     295                     300

TAC TTT GTG GAT CAT AAT ACG CGA ACT ACT ACT TGG GTG GAT CCG CGC    1197
Tyr Phe Val Asp His Asn Thr Arg Thr Thr Thr Trp Val Asp Pro Arg
305                     310                     315                     320

CGT CAA CAG TAC ATT CGT TCC TAT GGC GGT CCT AAT AAT GCT ACT ATT    1245
Arg Gln Gln Tyr Ile Arg Ser Tyr Gly Gly Pro Asn Asn Ala Thr Ile
                    325                     330                     335

CAG CAA CAA CCT GTC TCT CAA CTT GGT CCT TTG CCA AGT GGT TGG GAA    1293
Gln Gln Gln Pro Val Ser Gln Leu Gly Pro Leu Pro Ser Gly Trp Glu
                340                     345                     350

ATG CGT CTT ACC AAT ACT GCT CGT GTA TAT TTT GTT GAT CAC AAT ACC    1341
Met Arg Leu Thr Asn Thr Ala Arg Val Tyr Phe Val Asp His Asn Thr
```

```
Met Arg Leu Thr Asn Thr Ala Arg Val Tyr Phe Val Asp His Asn Thr
    355                 360                 365

AAG ACT ACC ACT TGG GAT GAT CCT CGT TTA CCT TCG TCG TTA GAT CAA          1389
Lys Thr Thr Thr Trp Asp Asp Pro Arg Leu Pro Ser Ser Leu Asp Gln
    370                 375                 380

AAC GTT CCT CAA TAC AAA CGT GAT TTC CGT AGA AAG TTG ATT TAT TTC          1437
Asn Val Pro Gln Tyr Lys Arg Asp Phe Arg Arg Lys Leu Ile Tyr Phe
385                 390                 395                 400

CTT TCG CAA CCA GCT TTG CAT CCT TTG CCA GGG CAG TGC CAC ATT AAA          1485
Leu Ser Gln Pro Ala Leu His Pro Leu Pro Gly Gln Cys His Ile Lys
                405                 410                 415

GTG CGT AGA AAT CAT ATC TTT GAA GAT TCG TAT GCG GAA ATT ATG AGA          1533
Val Arg Arg Asn His Ile Phe Glu Asp Ser Tyr Ala Glu Ile Met Arg
            420                 425                 430

CAA TCT GCA ACC GAT TTG AAA AAA CGT TTG ATG ATT AAG TTT GAT GGT          1581
Gln Ser Ala Thr Asp Leu Lys Lys Arg Leu Met Ile Lys Phe Asp Gly
        435                 440                 445

GAA GAT GGT TTG GAT TAC GGT GGA TTA TCC CGT GAA TAC TTC TTT TTG          1629
Glu Asp Gly Leu Asp Tyr Gly Gly Leu Ser Arg Glu Tyr Phe Phe Leu
    450                 455                 460

TTA TCA CAT GAA ATG TTC AAC CCC TTT TAT TGT TTA TTT GAA TAC TCT          1677
Leu Ser His Glu Met Phe Asn Pro Phe Tyr Cys Leu Phe Glu Tyr Ser
465                 470                 475                 480

TCG GTT GAT AAT TAT ACG CTT CAA ATT AAT CCT CAT TCT GGC ATT AAT          1725
Ser Val Asp Asn Tyr Thr Leu Gln Ile Asn Pro His Ser Gly Ile Asn
                485                 490                 495

CCA GAG CAT TTG AAC TAT TTC AAG TTC ATA GGC CGA GTC ATT GGT CTC          1773
Pro Glu His Leu Asn Tyr Phe Lys Phe Ile Gly Arg Val Ile Gly Leu
            500                 505                 510

GCA ATT TTC CAT CGT CGG TTT GTT GAT GCC TTT TTC GTT GTT TCT TTT          1821
Ala Ile Phe His Arg Arg Phe Val Asp Ala Phe Phe Val Val Ser Phe
        515                 520                 525

TAC AAA ATG ATT TTA CAA AAG AAG GTG ACG TTA CAG GAT ATG GAA AGT          1869
Tyr Lys Met Ile Leu Gln Lys Lys Val Thr Leu Gln Asp Met Glu Ser
    530                 535                 540

ATG GAT GCA GAG TAT TAT CGA AGT TTA GTC TGG ATT TTG GAC AAC GAT          1917
Met Asp Ala Glu Tyr Tyr Arg Ser Leu Val Trp Ile Leu Asp Asn Asp
545                 550                 555                 560

ATA ACC GGT GTT CTT GAT TTG ACC TTT AGT GTC GAA GAC AAT TGT TTT          1965
Ile Thr Gly Val Leu Asp Leu Thr Phe Ser Val Glu Asp Asn Cys Phe
                565                 570                 575

GGC GAG GTT GTT ACG ATT GAT TTG AAG CCG AAT GGT CGA AAC ATT GAA          2013
Gly Glu Val Val Thr Ile Asp Leu Lys Pro Asn Gly Arg Asn Ile Glu
            580                 585                 590

GTT ACA GAA GAG AAT AAA CGC GAA TAT GTT GAT TTG GTG ACT GTA TGG          2061
Val Thr Glu Glu Asn Lys Arg Glu Tyr Val Asp Leu Val Thr Val Trp
        595                 600                 605

ATT CAA AAA CGT ATA GAA GAG CAG TTT AAT GCA TTT CAT GAA GGT TTT          2109
Ile Gln Lys Arg Ile Glu Glu Gln Phe Asn Ala Phe His Glu Gly Phe
    610                 615                 620

AGT GAG CTC ATA CCA CAG GAA CTG ATT AAC GTG TTT GAC GAG AGA GAA          2157
Ser Glu Leu Ile Pro Gln Glu Leu Ile Asn Val Phe Asp Glu Arg Glu
625                 630                 635                 640

TTG GAG TTG TTG ATT GGA GGC ATT TCC GAA ATT GAC ATG GAG GAT TGG          2205
Leu Glu Leu Leu Ile Gly Gly Ile Ser Glu Ile Asp Met Glu Asp Trp
                645                 650                 655

AAG AAG CAT AAG GAT TAT CGT TCA TAC AGT GAA AAT GAC CAG ATT ATT          2253
Lys Lys His Lys Asp Tyr Arg Ser Tyr Ser Glu Asn Asp Gln Ile Ile
            660                 665                 670
```

-continued

| | | | | | | | | | | | | |
|---|---|---|---|---|---|---|---|---|---|---|---|---|
| AAA | TGG | TTT | TGG | GAA | CTT | ATG | GAT | GAA | TGG | AGT | AAT | GAA | AAG | AAA | TCC | 2301 |
| Lys | Trp | Phe | Trp | Glu | Leu | Met | Asp | Glu | Trp | Ser | Asn | Glu | Lys | Lys | Ser | |
| | | | 675 | | | | 680 | | | | | 685 | | | | |

```
AAA TGG TTT TGG GAA CTT ATG GAT GAA TGG AGT AAT GAA AAG AAA TCC    2301
Lys Trp Phe Trp Glu Leu Met Asp Glu Trp Ser Asn Glu Lys Lys Ser
            675             680                 685

AGA CTT TTA CAA TTT ACC ACT GGT ACT AGC CGA ATT CCT GTC AAC GGG    2349
Arg Leu Leu Gln Phe Thr Thr Gly Thr Ser Arg Ile Pro Val Asn Gly
        690                 695                 700

TTC AAA GAT TTG CAA GGA AGT GAT GGC CCC CGT AAG TTT ACT ATT GAA    2397
Phe Lys Asp Leu Gln Gly Ser Asp Gly Pro Arg Lys Phe Thr Ile Glu
705                 710                 715                 720

AAA GCT GGT GAA CCC AAT AAA CTT CCC AAG GCC CAC ACC TGT TTC AAT    2445
Lys Ala Gly Glu Pro Asn Lys Leu Pro Lys Ala His Thr Cys Phe Asn
                725                 730                 735

CGA CTT GAT CTT CCT CCT TAT ACT TCG AAA AAA GAT TTG GAT CAT AAA    2493
Arg Leu Asp Leu Pro Pro Tyr Thr Ser Lys Lys Asp Leu Asp His Lys
            740                 745                 750

TTG TCC ATA GCT GTT GAA GAG ACG ATT GGT TTT GGT CAG GAG            2535
Leu Ser Ile Ala Val Glu Glu Thr Ile Gly Phe Gly Gln Glu
                755                 760                 765
```

| | |
|---|---|
| TAAAATGGAT AGCTAGCTAT TGATTACTTT TGATATTTGA ACTATTGGTG TTTAACAGTG | 2595 |
| AAAAAGAATT TCTGTGTAAA GTTTCCGAAA TTATTTTTTT TTTCTCATTT GAGTGAAAAT | 2655 |
| ACTTGGATCA TCATGTTCTA CCTTTGTGTT CTCTACTACC ATTTTCCTTC TTCTTTTTAT | 2715 |
| ACTTGTTTGC AAACACATTT CCTCTTAATG CTCTTCGCAC AAAACATATA AGTTAATTTA | 2775 |
| CTATTATTAA GTTACGTACT GCATAAGTGA TTTTATATTT ATGAAATTAC CGCCCTTTTT | 2835 |
| CAACATTTTA ATT | 2848 |

(2) INFORMATION FOR SEQ ID NO:4:

(i) SEQUENCE CHARACTERISTICS:
        (A) LENGTH: 766 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Asn Ser Ala Gln Ser Arg Arg Ile Arg Val Thr Ile Val Ala
 1               5                  10                  15

Ala Asp Gly Leu Tyr Lys Arg Asp Val Phe Arg Phe Pro Asp Pro Phe
                20                  25                  30

Ala Val Leu Thr Val Asp Gly Glu Gln Thr His Thr Thr Thr Ala Ile
            35                  40                  45

Lys Lys Thr Leu Asn Pro Tyr Trp Asn Glu Thr Phe Glu Val Asn Val
        50                  55                  60

Thr Asp Asn Ser Thr Ile Ala Ile Gln Val Phe Asp Gln Lys Lys Phe
65                  70                  75                  80

Lys Lys Lys Gly Gln Gly Phe Leu Gly Val Ile Asn Leu Arg Val Gly
                85                  90                  95

Asp Val Leu Asp Leu Ala Ile Gly Gly Asp Glu Met Leu Thr Arg Asp
                100                 105                 110

Leu Lys Lys Ser Asn Glu Asn Thr Val Val His Gly Lys Ile Ile Ile
            115                 120                 125

Asn Leu Ser Thr Thr Ala Gln Ser Thr Leu Gln Val Pro Ser Ser Ala
        130                 135                 140

Ala Ser Gly Ala Arg Thr Gln Arg Thr Ser Ile Thr Asn Asp Pro Gln
145                 150                 155                 160

Ser Ser Lys Ser Ser Ser Val Ser Arg Asn Pro Ala Ser Ser Arg Ala
```

```
                  165                 170                 175
Gly Ser Pro Thr Arg Asp Asn Ala Pro Ala Ala Ser Pro Ala Ser Ser
                180                 185                 190

Glu Pro Arg Thr Phe Ser Ser Phe Glu Asp Gln Tyr Gly Arg Leu Pro
                195                 200                 205

Pro Gly Trp Glu Arg Arg Thr Asp Asn Leu Gly Arg Thr Tyr Tyr Val
                210                 215                 220

Asp His Asn Thr Arg Ser Thr Thr Trp Ile Arg Pro Asn Leu Ser Ser
225                 230                 235                 240

Val Ala Gly Ala Ala Ala Glu Leu His Ser Ser Ala Ser Ser Ala
                245                 250                 255

Asn Val Thr Glu Gly Val Gln Pro Ser Ser Ser Asn Ala Ala Arg Arg
                260                 265                 270

Thr Glu Ala Ser Val Leu Thr Ser Asn Ala Thr Thr Ala Gly Ser Gly
                275                 280                 285

Glu Leu Pro Pro Gly Trp Glu Gln Arg Tyr Thr Pro Glu Gly Arg Pro
                290                 295                 300

Tyr Phe Val Asp His Asn Thr Arg Thr Thr Thr Trp Val Asp Pro Arg
305                 310                 315                 320

Arg Gln Gln Tyr Ile Arg Ser Tyr Gly Gly Pro Asn Asn Ala Thr Ile
                325                 330                 335

Gln Gln Gln Pro Val Ser Gln Leu Gly Pro Leu Pro Ser Gly Trp Glu
                340                 345                 350

Met Arg Leu Thr Asn Thr Ala Arg Val Tyr Phe Val Asp His Asn Thr
                355                 360                 365

Lys Thr Thr Thr Trp Asp Asp Pro Arg Leu Pro Ser Ser Leu Asp Gln
                370                 375                 380

Asn Val Pro Gln Tyr Lys Arg Asp Phe Arg Arg Lys Leu Ile Tyr Phe
385                 390                 395                 400

Leu Ser Gln Pro Ala Leu His Pro Leu Pro Gly Gln Cys His Ile Lys
                405                 410                 415

Val Arg Arg Asn His Ile Phe Glu Asp Ser Tyr Ala Glu Ile Met Arg
                420                 425                 430

Gln Ser Ala Thr Asp Leu Lys Lys Arg Leu Met Ile Lys Phe Asp Gly
                435                 440                 445

Glu Asp Gly Leu Asp Tyr Gly Gly Leu Ser Arg Glu Tyr Phe Phe Leu
450                 455                 460

Leu Ser His Glu Met Phe Asn Pro Phe Tyr Cys Leu Phe Glu Tyr Ser
465                 470                 475                 480

Ser Val Asp Asn Tyr Thr Leu Gln Ile Asn Pro His Ser Gly Ile Asn
                485                 490                 495

Pro Glu His Leu Asn Tyr Phe Lys Phe Ile Gly Arg Val Ile Gly Leu
                500                 505                 510

Ala Ile Phe His Arg Arg Phe Val Asp Ala Phe Phe Val Val Ser Phe
                515                 520                 525

Tyr Lys Met Ile Leu Gln Lys Lys Val Thr Leu Gln Asp Met Glu Ser
                530                 535                 540

Met Asp Ala Glu Tyr Tyr Arg Ser Leu Val Trp Ile Leu Asp Asn Asp
545                 550                 555                 560

Ile Thr Gly Val Leu Asp Leu Thr Phe Ser Val Glu Asp Asn Cys Phe
                565                 570                 575

Gly Glu Val Val Thr Ile Asp Leu Lys Pro Asn Gly Arg Asn Ile Glu
                580                 585                 590
```

-continued

```
Val Thr Glu Glu Asn Lys Arg Glu Tyr Val Asp Leu Val Thr Val Trp
        595                 600                 605

Ile Gln Lys Arg Ile Glu Glu Gln Phe Asn Ala Phe His Gly Phe
        610                 615                 620

Ser Glu Leu Ile Pro Gln Glu Leu Ile Asn Val Phe Asp Glu Arg Glu
625                 630                 635                 640

Leu Glu Leu Leu Ile Gly Gly Ile Ser Glu Ile Asp Met Glu Asp Trp
                645                 650                 655

Lys Lys His Lys Asp Tyr Arg Ser Tyr Ser Glu Asn Asp Gln Ile Ile
                660                 665                 670

Lys Trp Phe Trp Glu Leu Met Asp Glu Trp Ser Asn Glu Lys Lys Ser
        675                 680                 685

Arg Leu Leu Gln Phe Thr Thr Gly Thr Ser Arg Ile Pro Val Asn Gly
        690                 695                 700

Phe Lys Asp Leu Gln Gly Ser Asp Gly Pro Arg Lys Phe Thr Ile Glu
705                 710                 715                 720

Lys Ala Gly Glu Pro Asn Lys Leu Pro Lys Ala His Thr Cys Phe Asn
                725                 730                 735

Arg Leu Asp Leu Pro Pro Tyr Thr Ser Lys Lys Asp Leu Asp His Lys
                740                 745                 750

Leu Ser Ile Ala Val Glu Glu Thr Ile Gly Phe Gly Gln Glu
        755                 760                 765
```

(2) INFORMATION FOR SEQ ID NO:5:

(i) SEQUENCE CHARACTERISTICS:
        (A) LENGTH: 3226 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 400..2901

(xi) SEQUENCE DESCRIPTION: SEQ ID NO:5:

```
CGGTATCAGC AGAGGTGTGT ACGGGCACTG CTTTAAAACT GGGAAGGAGG AAGACGAGGC      60

CAGGGAGCCG GAGGGTCACC AAGGTAGATT TCCAGCAGCG CTAGTCCAGC TGAACACTTT     120

CCAGCCTTGT TTTTCAGCAG CTTTGAGGAA AAGTATAGTG ATCCGTATGT GAAACTTTCA     180

TTGTACGTAG CGGATGAGAA TAGAGAACTT GCTTTGGTCC AGACAAAAAC AATTAAAAAG     240

ACACTGAACC CAAAATGGAA TGAAGAATTT TATTTCAGGG TAAACCCATC TAATCACAGA     300

CTCCTATTTG AAGTATTTGA CGAAAATAGA CTGACACGAG ACGGCTTCCT GGGCCAGGTG     360

GACGTGCCCC TTAGTCACCT TCCGACAGAA GATCCAACC ATG GAG CGA CCC TAT       414
                                            Met Glu Arg Pro Tyr
                                              1               5

ACA TTT AAG GAC TTT CTC CTC AGA CCA AGA AGT CAT AAG TCT CGA GTT      462
Thr Phe Lys Asp Phe Leu Leu Arg Pro Arg Ser His Lys Ser Arg Val
             10                  15                  20

AAG GGA TTT TTG CGA TTG AAA ATG GCC TAT ATG CCA AAA AAT GGA GGT      510
Lys Gly Phe Leu Arg Leu Lys Met Ala Tyr Met Pro Lys Asn Gly Gly
         25                  30                  35

CAA GAT GAA GAA AAC AGT GAC CAG AGG GAT GAC ATG GAG CAT GGA TGG      558
Gln Asp Glu Glu Asn Ser Asp Gln Arg Asp Asp Met Glu His Gly Trp
     40                  45                  50
```

```
GAA GTT GTT GAC TCA AAT GAC TCG GCT TCT CAG CAC CAA GAG GAA CTT       606
Glu Val Val Asp Ser Asn Asp Ser Ala Ser Gln His Gln Glu Glu Leu
    55                  60                  65

CCT CCT CCT CCT CTG CCT CCC GGG TGG GAA GAA AAA GTG GAC AAT TTA       654
Pro Pro Pro Pro Leu Pro Pro Gly Trp Glu Glu Lys Val Asp Asn Leu
70                  75                  80                       85

GGC CGA ACT TAC TAT GTC AAC CAC AAC AAC CGG ACC ACT CAG TGG CAC       702
Gly Arg Thr Tyr Tyr Val Asn His Asn Asn Arg Thr Thr Gln Trp His
                    90                  95                  100

AGA CCA AGC CTG ATG GAC GTG TCC TCG GAG TCG GAC AAT AAC ATC AGA       750
Arg Pro Ser Leu Met Asp Val Ser Ser Glu Ser Asp Asn Asn Ile Arg
                105                 110                 115

CAG ATC AAC CAG GAG GCA GCA CAC CGG CGC TTC CGC TCC CGC AGG CAC       798
Gln Ile Asn Gln Glu Ala Ala His Arg Arg Phe Arg Ser Arg Arg His
            120                 125                 130

ATC AGC GAA GAC TTG GAG CCC GAG CCC TCG GAG GGC GGG GAT GTC CCC       846
Ile Ser Glu Asp Leu Glu Pro Glu Pro Ser Glu Gly Gly Asp Val Pro
        135                 140                 145

GAG CCT TGG GAG ACC ATT TCA GAG GAA GTG AAT ATC GCT GGA GAC TCT       894
Glu Pro Trp Glu Thr Ile Ser Glu Glu Val Asn Ile Ala Gly Asp Ser
150                 155                 160                 165

CTC GGT CTG GCT CTG CCC CCA CCA CCG GTC TCC CCA GGA TCT CGG ACC       942
Leu Gly Leu Ala Leu Pro Pro Pro Pro Val Ser Pro Gly Ser Arg Thr
                170                 175                 180

AGC CCT CAG GAG CTG TCA GAG GAA CTA AGC AGA AGG CTT CAG ATC ACT       990
Ser Pro Gln Glu Leu Ser Glu Glu Leu Ser Arg Arg Leu Gln Ile Thr
            185                 190                 195

CCA GAC TCC AAT GGG GAA CAG TTC AGC TCT TTG ATT CAA AGA GAA CCC      1038
Pro Asp Ser Asn Gly Glu Gln Phe Ser Ser Leu Ile Gln Arg Glu Pro
        200                 205                 210

TCC TCA AGG TTG AGG TCA TGC AGT GTC ACC GAC GCA GTT GCA GAA CAG      1086
Ser Ser Arg Leu Arg Ser Cys Ser Val Thr Asp Ala Val Ala Glu Gln
215                 220                 225

GGC CAT CTA CCA CCG CCA TCA GTG GCC TAT GTA CAT ACC ACG CCG GGT      1134
Gly His Leu Pro Pro Pro Ser Val Ala Tyr Val His Thr Thr Pro Gly
230                 235                 240                 245

CTG CCT TCA GGC TGG GAA GAA AGA AAA GAT GCT AAG GGG CGC ACA TAC      1182
Leu Pro Ser Gly Trp Glu Glu Arg Lys Asp Ala Lys Gly Arg Thr Tyr
                250                 255                 260

TAT GTC AAT CAT AAC AAT CGA ACC ACA ACT TGG ACT CGA CCT ATC ATG      1230
Tyr Val Asn His Asn Asn Arg Thr Thr Thr Trp Thr Arg Pro Ile Met
            265                 270                 275

CAG CTT GCA GAA GAT GGT GCG TCC GGA TCA GCC ACA AAC AGT AAC AAC      1278
Gln Leu Ala Glu Asp Gly Ala Ser Gly Ser Ala Thr Asn Ser Asn Asn
        280                 285                 290

CAT CTA ATC GAG CCT CAG ATC CGC CGG CCT CGT AGC CTC AGC TCG CCA      1326
His Leu Ile Glu Pro Gln Ile Arg Arg Pro Arg Ser Leu Ser Ser Pro
295                 300                 305

ACA GTA ACT TTA TCT GCC CCG CTG GAG GGT GCC AAG GAC TCA CCC GTA      1374
Thr Val Thr Leu Ser Ala Pro Leu Glu Gly Ala Lys Asp Ser Pro Val
310                 315                 320                 325

CGT CGG GCT GTG AAA GAC ACC CTT TCC AAC CCA CAG TCC CCA CAG CCA      1422
Arg Arg Ala Val Lys Asp Thr Leu Ser Asn Pro Gln Ser Pro Gln Pro
                330                 335                 340

TCA CCT TAC AAC TCC CCC AAA CCA CAA CAC AAA GTC ACA CAG AGC TTC      1470
Ser Pro Tyr Asn Ser Pro Lys Pro Gln His Lys Val Thr Gln Ser Phe
            345                 350                 355

TTG CCA CCC GGC TGG GAA ATG AGG ATA GCG CCA AAC GGC CGG CCC TTC      1518
Leu Pro Pro Gly Trp Glu Met Arg Ile Ala Pro Asn Gly Arg Pro Phe
        360                 365                 370
```

```
TTC ATT GAT CAT AAC ACA AAG ACA ACA ACC TGG GAA GAT CCA CGT TTG          1566
Phe Ile Asp His Asn Thr Lys Thr Thr Thr Trp Glu Asp Pro Arg Leu
    375                 380                 385

AAA TTT CCA GTA CAT ATG CGG TCA AAG ACA TCT TTA AAC CCC AAT GAC          1614
Lys Phe Pro Val His Met Arg Ser Lys Thr Ser Leu Asn Pro Asn Asp
390                 395                 400                 405

CTT GGC CCC CTT CCT CCT GGC TGG GAA GAA AGA ATT CAC TTG GAT GGC          1662
Leu Gly Pro Leu Pro Pro Gly Trp Glu Glu Arg Ile His Leu Asp Gly
                410                 415                 420

CGA ACG TTT TAT ATT GAT CAT AAT AGC AAA ATT ACT CAG TGG GAA GAC          1710
Arg Thr Phe Tyr Ile Asp His Asn Ser Lys Ile Thr Gln Trp Glu Asp
            425                 430                 435

CCA AGA CTG CAG AAC CCA GCT ATT ACT GGT CCG GCT GTC CCT TAC TCC          1758
Pro Arg Leu Gln Asn Pro Ala Ile Thr Gly Pro Ala Val Pro Tyr Ser
        440                 445                 450

AGA GAA TTT AAG CAG AAA TAT GAC TAC TTC AGG AAG AAA TTA AAG AAA          1806
Arg Glu Phe Lys Gln Lys Tyr Asp Tyr Phe Arg Lys Lys Leu Lys Lys
    455                 460                 465

CCT GCT GAT ATC CCC AAT AGG TTT GAA ATG AAA CTT CAC AGA AAT AAC          1854
Pro Ala Asp Ile Pro Asn Arg Phe Glu Met Lys Leu His Arg Asn Asn
470                 475                 480                 485

ATA TTT GAA GAG TCC TAT CGG AGA ATT ATG TCC GTG AAA AGA CCA GAT          1902
Ile Phe Glu Glu Ser Tyr Arg Arg Ile Met Ser Val Lys Arg Pro Asp
                490                 495                 500

GTC CTA AAA GCT AGA CTG TGG ATT GAG TTT GAA TCA GAG AAA GGT CTT          1950
Val Leu Lys Ala Arg Leu Trp Ile Glu Phe Glu Ser Glu Lys Gly Leu
            505                 510                 515

GAC TAT GGG GGT GTG GCC AGA GAA TGG TTC TTC TTA CTG TCC AAA GAG          1998
Asp Tyr Gly Gly Val Ala Arg Glu Trp Phe Phe Leu Leu Ser Lys Glu
        520                 525                 530

ATG TTC AAC CCC TAC TAC GGC CTC TTT GAG TAC TCT GCC ACG GAC AAC          2046
Met Phe Asn Pro Tyr Tyr Gly Leu Phe Glu Tyr Ser Ala Thr Asp Asn
    535                 540                 545

TAC ACC CTT CAG ATC AAC CCT AAT TCA GGC CTC TGT AAT GAG GAT CAT          2094
Tyr Thr Leu Gln Ile Asn Pro Asn Ser Gly Leu Cys Asn Glu Asp His
550                 555                 560                 565

TTG TCC TAC TTC ACT TTT ATT GGA AGA GTT GCT GGT CTG GCC GTA TTT          2142
Leu Ser Tyr Phe Thr Phe Ile Gly Arg Val Ala Gly Leu Ala Val Phe
                570                 575                 580

CAT GGG AAG CTC TTA GAT GGT TTC TTC ATT AGA CCA TTT TAC AAG ATG          2190
His Gly Lys Leu Leu Asp Gly Phe Phe Ile Arg Pro Phe Tyr Lys Met
            585                 590                 595

ATG TTG GGA AAG CAG ATA ACC CTG AAT GAC ATG GAA TCT GTG GAT AGT          2238
Met Leu Gly Lys Gln Ile Thr Leu Asn Asp Met Glu Ser Val Asp Ser
        600                 605                 610

GAA TAT TAC AAC TCT TTG AAA TGG ATC CTG GAG AAT GAC CCT ACT GAG          2286
Glu Tyr Tyr Asn Ser Leu Lys Trp Ile Leu Glu Asn Asp Pro Thr Glu
    615                 620                 625

CTG GAC CTC ATG TTC TGC ATA GAC GAA GAA AAC TTT GGA CAG ACA TAT          2334
Leu Asp Leu Met Phe Cys Ile Asp Glu Glu Asn Phe Gly Gln Thr Tyr
630                 635                 640                 645

CAA GTG GAT TTG AAG CCC AAT GGG TCA GAA ATA ATG GTC ACA AAT GAA          2382
Gln Val Asp Leu Lys Pro Asn Gly Ser Glu Ile Met Val Thr Asn Glu
                650                 655                 660

AAC AAA AGG GAA TAT ATC GAC TTA GTC ATC CAG TGG AGA TTT GTG AAC          2430
Asn Lys Arg Glu Tyr Ile Asp Leu Val Ile Gln Trp Arg Phe Val Asn
            665                 670                 675

AGG GTC CAG AAG CAG ATG AAC GCC TTC TTG GAG GGA TTC ACA GAA CTA          2478
Arg Val Gln Lys Gln Met Asn Ala Phe Leu Glu Gly Phe Thr Glu Leu
```

```
                680                  685                       690
CTT CCT ATT GAT TTG ATT AAA ATT TTT GAT GAA AAT GAG CTG GAG TTG        2526
Leu Pro Ile Asp Leu Ile Lys Ile Phe Asp Glu Asn Glu Leu Glu Leu
    695                 700                 705

CTC ATG TGC GGC CTC GGT GAT GTG GAT GTG AAT GAC TGG AGA CAG CAT        2574
Leu Met Cys Gly Leu Gly Asp Val Asp Val Asn Asp Trp Arg Gln His
710                 715                 720                 725

TCT ATT TAC AAG AAC GGC TAC TGC CCA AAC CAC CCC GTC ATT CAG TGG        2622
Ser Ile Tyr Lys Asn Gly Tyr Cys Pro Asn His Pro Val Ile Gln Trp
                730                 735                 740

TTC TGG AAG GCT GTG CTA CTC ATG GAC GCC GAA AAG CGT ATC CGG TTA        2670
Phe Trp Lys Ala Val Leu Leu Met Asp Ala Glu Lys Arg Ile Arg Leu
            745                 750                 755

CTG CAG TTT GTC ACA GGG ACA TCG CGA GTA CCT ATG AAT GGA TTT GCC        2718
Leu Gln Phe Val Thr Gly Thr Ser Arg Val Pro Met Asn Gly Phe Ala
        760                 765                 770

GAA CTT TAT GGT TCC AAT GGT CCT CAG CTG TTT ACA ATA GAG CAA TGG        2766
Glu Leu Tyr Gly Ser Asn Gly Pro Gln Leu Phe Thr Ile Glu Gln Trp
    775                 780                 785

GGC AGT CCT GAG AAA CTC CCC AGA GCT CAC ACA TGC TTT AAT CGC CTT        2814
Gly Ser Pro Glu Lys Leu Pro Arg Ala His Thr Cys Phe Asn Arg Leu
790                 795                 800                 805

GAC TTA CCT CCA TAT GAA ACC TTT GAA GAT TTA CGA GAG AAA CTT CTC        2862
Asp Leu Pro Pro Tyr Glu Thr Phe Glu Asp Leu Arg Glu Lys Leu Leu
                810                 815                 820

ATG GCC GTG GAA AAT GCT CAA GGA TTT GAA GGG GTG GAT TAAGCACCCT        2911
Met Ala Val Glu Asn Ala Gln Gly Phe Glu Gly Val Asp
            825                 830

GTGCCTCGGG GGTGGTTGTT CTTCAAGCAA GTTCTGCTTG CACTTTTGCA TTTGCCTAAC      2971

AGACTTTTGC AGAGGCGATG GCAGAGAGCA GCTGCAGGCA TGGTCCCTGG AGCCGAGCCT      3031

TCACCACGCA CTCGTCCAAG TTCGGATGCG GGAACCTGGT CCCAGCTTGA GTTCCTGCCT      3091

TTCCCACCAC AAATTATCAA CTGGTTGATG TGTACACTAA TTACATTTCA GGAGGACTTA      3151

ATGCTATTTA TGTTGTGCCT CTGCAGCAAA GCCCTTAATA AATATTTTAC ATCCTTAAAA      3211

AAAAAAAAAA AAAAA                                                       3226
```

(2) INFORMATION FOR SEQ ID NO:6:

(i) SEQUENCE CHARACTERISTICS:
        (A) LENGTH: 834 amino acids
        (B) TYPE: amino acid
        (D) TOPOLOGY: linear (ii) MOLECULE TYPE: protein (xi) SEQUENCE DESCRIPTION: SEQ ID NO:6:

```
Met Glu Arg Pro Tyr Thr Phe Lys Asp Phe Leu Leu Arg Pro Arg Ser
1               5                   10                  15

His Lys Ser Arg Val Lys Gly Phe Leu Arg Leu Lys Met Ala Tyr Met
                20                  25                  30

Pro Lys Asn Gly Gly Gln Asp Glu Asn Ser Asp Gln Arg Asp Asp
            35                  40                  45

Met Glu His Gly Trp Glu Val Val Asp Ser Asn Asp Ser Ala Ser Gln
        50                  55                  60

His Gln Glu Glu Leu Pro Pro Pro Leu Pro Pro Gly Trp Glu Glu
    65                  70                  75                  80

Lys Val Asp Asn Leu Gly Arg Thr Tyr Tyr Val Asn His Asn Asn Arg
                85                  90                  95
```

-continued

```
Thr Thr Gln Trp His Arg Pro Ser Leu Met Asp Val Ser Ser Glu Ser
            100                 105                 110

Asp Asn Asn Ile Arg Gln Ile Asn Gln Glu Ala Ala His Arg Arg Phe
            115                 120                 125

Arg Ser Arg Arg His Ile Ser Glu Asp Leu Glu Pro Glu Pro Ser Glu
            130                 135                 140

Gly Gly Asp Val Pro Glu Pro Trp Glu Thr Ile Ser Glu Glu Val Asn
145                 150                 155                 160

Ile Ala Gly Asp Ser Leu Gly Leu Ala Leu Pro Pro Pro Val Ser
                    165                 170                 175

Pro Gly Ser Arg Thr Ser Pro Gln Glu Leu Ser Glu Glu Leu Ser Arg
            180                 185                 190

Arg Leu Gln Ile Thr Pro Asp Ser Asn Gly Glu Gln Phe Ser Ser Leu
            195                 200                 205

Ile Gln Arg Glu Pro Ser Ser Arg Leu Arg Ser Cys Ser Val Thr Asp
            210                 215                 220

Ala Val Ala Glu Gln Gly His Leu Pro Pro Ser Val Ala Tyr Val
225                 230                 235                 240

His Thr Thr Pro Gly Leu Pro Ser Gly Trp Glu Glu Arg Lys Asp Ala
                    245                 250                 255

Lys Gly Arg Thr Tyr Tyr Val Asn His Asn Asn Arg Thr Thr Thr Trp
            260                 265                 270

Thr Arg Pro Ile Met Gln Leu Ala Glu Asp Gly Ala Ser Gly Ser Ala
            275                 280                 285

Thr Asn Ser Asn Asn His Leu Ile Glu Pro Gln Ile Arg Arg Pro Arg
290                 295                 300

Ser Leu Ser Ser Pro Thr Val Thr Leu Ser Ala Pro Leu Glu Gly Ala
305                 310                 315                 320

Lys Asp Ser Pro Val Arg Arg Ala Val Lys Asp Thr Leu Ser Asn Pro
                    325                 330                 335

Gln Ser Pro Gln Pro Ser Pro Tyr Asn Ser Pro Lys Pro Gln His Lys
            340                 345                 350

Val Thr Gln Ser Phe Leu Pro Pro Gly Trp Glu Met Arg Ile Ala Pro
            355                 360                 365

Asn Gly Arg Pro Phe Phe Ile Asp His Asn Thr Lys Thr Thr Thr Trp
370                 375                 380

Glu Asp Pro Arg Leu Lys Phe Pro Val His Met Arg Ser Lys Thr Ser
385                 390                 395                 400

Leu Asn Pro Asn Asp Leu Gly Pro Leu Pro Pro Gly Trp Glu Glu Arg
                    405                 410                 415

Ile His Leu Asp Gly Arg Thr Phe Tyr Ile Asp His Asn Ser Lys Ile
            420                 425                 430

Thr Gln Trp Glu Asp Pro Arg Leu Gln Asn Pro Ala Ile Thr Gly Pro
            435                 440                 445

Ala Val Pro Tyr Ser Arg Glu Phe Lys Gln Lys Tyr Asp Tyr Phe Arg
450                 455                 460

Lys Lys Leu Lys Lys Pro Ala Asp Ile Pro Asn Arg Phe Glu Met Lys
465                 470                 475                 480

Leu His Arg Asn Asn Ile Phe Glu Glu Ser Tyr Arg Arg Ile Met Ser
                    485                 490                 495

Val Lys Arg Pro Asp Val Leu Lys Ala Arg Leu Trp Ile Glu Phe Glu
            500                 505                 510
```

```
Ser Glu Lys Gly Leu Asp Tyr Gly Val Ala Arg Glu Trp Phe Phe
        515                 520                 525

Leu Leu Ser Lys Glu Met Phe Asn Pro Tyr Gly Leu Phe Glu Tyr
        530                 535             540

Ser Ala Thr Asp Asn Tyr Thr Leu Gln Ile Asn Pro Asn Ser Gly Leu
545                 550                 555                 560

Cys Asn Glu Asp His Leu Ser Tyr Phe Thr Phe Ile Gly Arg Val Ala
            565                 570                 575

Gly Leu Ala Val Phe His Gly Lys Leu Leu Asp Gly Phe Phe Ile Arg
            580                 585                 590

Pro Phe Tyr Lys Met Met Leu Gly Lys Gln Ile Thr Leu Asn Asp Met
        595                 600                 605

Glu Ser Val Asp Ser Glu Tyr Tyr Asn Ser Leu Lys Trp Ile Leu Glu
        610                 615                 620

Asn Asp Pro Thr Glu Leu Asp Leu Met Phe Cys Ile Asp Glu Glu Asn
625                 630                 635                 640

Phe Gly Gln Thr Tyr Gln Val Asp Leu Lys Pro Asn Gly Ser Glu Ile
                645                 650                 655

Met Val Thr Asn Glu Asn Lys Arg Glu Tyr Ile Asp Leu Val Ile Gln
            660                 665                 670

Trp Arg Phe Val Asn Arg Val Gln Lys Gln Met Asn Ala Phe Leu Glu
        675                 680                 685

Gly Phe Thr Glu Leu Leu Pro Ile Asp Leu Ile Lys Ile Phe Asp Glu
        690                 695                 700

Asn Glu Leu Glu Leu Leu Met Cys Gly Leu Gly Asp Val Asp Val Asn
705                 710                 715                 720

Asp Trp Arg Gln His Ser Ile Tyr Lys Asn Gly Tyr Cys Pro Asn His
                725                 730                 735

Pro Val Ile Gln Trp Phe Trp Lys Ala Val Leu Leu Met Asp Ala Glu
            740                 745                 750

Lys Arg Ile Arg Leu Leu Gln Phe Val Thr Gly Thr Ser Arg Val Pro
        755                 760                 765

Met Asn Gly Phe Ala Glu Leu Tyr Gly Ser Asn Gly Pro Gln Leu Phe
770                 775                 780

Thr Ile Glu Gln Trp Gly Ser Pro Glu Lys Leu Pro Arg Ala His Thr
785                 790                 795                 800

Cys Phe Asn Arg Leu Asp Leu Pro Pro Tyr Glu Thr Phe Glu Asp Leu
                805                 810                 815

Arg Glu Lys Leu Leu Met Ala Val Glu Asn Ala Gln Gly Phe Glu Gly
            820                 825                 830

Val Asp
```